United States Patent
Jendrisak et al.

(10) Patent No.: US 8,309,335 B2
(45) Date of Patent: Nov. 13, 2012

(54) SELECTIVE 5' LIGATION TAGGING OF RNA

(75) Inventors: Jerome Jendrisak, Madison, WI (US); Ramesh Vaidyanathan, Madison, WI (US); Gary Dahl, Madison, WI (US)

(73) Assignee: Epicentre Technologies Corporation, Madison, WI (US)

( * ) Notice: Subject to any disclaimer, the term of this patent is extended or adjusted under 35 U.S.C. 154(b) by 0 days.

(21) Appl. No.: 13/408,851

(22) Filed: Feb. 29, 2012

(65) Prior Publication Data

US 2012/0156753 A1    Jun. 21, 2012

Related U.S. Application Data

(60) Division of application No. 12/707,243, filed on Feb. 17, 2010, now Pat. No. 8,163,491, which is a continuation-in-part of application No. PCT/US2008/073305, filed on Aug. 15, 2008, said application No. 12/707,243 is a continuation-in-part of application No. PCT/US2009/042723, filed on May 4, 2009.

(60) Provisional application No. 60/956,536, filed on Aug. 17, 2007, provisional application No. 61/050,046, filed on May 2, 2008.

(51) Int. Cl.
  *C12N 9/12* (2006.01)
  *C12N 9/22* (2006.01)
  *C12N 9/16* (2006.01)
(52) U.S. Cl. ........................... 435/194; 435/199
(58) Field of Classification Search .................. None
  See application file for complete search history.

(56) References Cited

U.S. PATENT DOCUMENTS

| | | | |
|---|---|---|---|
| 5,573,913 A | 11/1996 | Rosemeyer et al. | |
| 5,597,713 A | 1/1997 | Kato et al. | |
| 5,849,546 A | 12/1998 | Sousa et al. | |
| 7,303,901 B2 | 12/2007 | Hjorleifsdottir et al. | |
| 7,452,705 B2 | 11/2008 | Kazmierczak et al. | |
| 2004/0029129 A1* | 2/2004 | Wang et al. | 435/6 |
| 2004/0171041 A1 | 9/2004 | Dahl et al. | |
| 2005/0130201 A1 | 6/2005 | Deras et al. | |
| 2007/0072208 A1 | 3/2007 | Drmanac | |
| 2007/0099208 A1 | 5/2007 | Drmanac et al. | |
| 2008/0108804 A1 | 5/2008 | Hayashizaki et al. | |

(Continued)

FOREIGN PATENT DOCUMENTS

WO    0104286    1/2001

(Continued)

OTHER PUBLICATIONS

Banerjee, "5'-terminal cap structure in eucaryotic messenger ribonuclease acids", Microbiol Rev 44(2), 1980, 175-205.

(Continued)

*Primary Examiner* — Samuel Woolwine
*Assistant Examiner* — Suchira Pande
(74) *Attorney, Agent, or Firm* — Lisa de Berg

(57) ABSTRACT

The present invention provides novel compositions, kits and methods employing RNA 5' polyphosphatases, RNA 5' monophosphatases, capping enzymes, decapping enzymes, nucleic acid pyrophosphatases and RNA ligases, as well as other enzymes, for selective 5' ligation tagging of desired classes of RNA molecules that differ with respect to particular chemical moieties on their 5' ends. The 5' tagged RNA molecules can be used for synthesis of tagged first-stand cDNA, double-stranded cDNA, and sense or antisense RNA for a variety of uses.

13 Claims, 4 Drawing Sheets

Examples of Reactions Catalyzed by RNA 5' Polyphosphatase

N = RNA, DNA, NTPs, NDPs, dNTPs, dNDPs

U.S. PATENT DOCUMENTS

| | | |
|---|---|---|
| 2008/0213771 A1 | 9/2008 | Drmanac |
| 2008/0234136 A1 | 9/2008 | Drmanac et al. |
| 2008/0318796 A1 | 12/2008 | Drmanac et al. |
| 2009/0005252 A1 | 1/2009 | Drmanac et al. |
| 2009/0011943 A1 | 1/2009 | Drmanac et al. |

FOREIGN PATENT DOCUMENTS

| | | |
|---|---|---|
| WO | 2007117039 | 10/2007 |
| WO | 2009026148 | 2/2009 |
| WO | 2009135212 | 11/2009 |

OTHER PUBLICATIONS

Butler, et al., "Bacteriophage SP6-specific RNA polymerase. I. Isolation and characterization of the enzyme", J. Biol. Chem 257, 1982, 5772-5778.

Coller, et al., "Eukaryotic mRNA decapping", Ann Rev Biochem 73, 2004, 861-890.

Deana, et al., "The bacterial enzyme RppH triggers messenger RNA degradation by 5' pyrophosphate removal", Nature 451, 2008, 355-358.

Deshpande, et al., "Human PIR1 of the protein-tyrosine phosphatase superfamily has RNA 5'-triphosphatase and diphosphatase activities", J Biol Chem 274, 1999, 16590-16594.

Drummond, et al., NAR 13, 1979, 7574.

Dunckley, et al., "The DCP2 protein is required for mRNA decapping in Saccharomyces cerevisiae and contains a functional MutT motif", EMBO J 18, 1999, 5411-5422.

Dunn, et al., "Different template specificities of phage T3 and T7 RNA polymerases", Natural new Biology 230, 1971, 94-96.

Edmonds, "Polyadenylate polymerases", Methods Enzymol. 181, 1990, 161-180.

Fischer, et al., "Diversity in the signals required for nuclear accumulation of U snRNPs and variety in the pathways of nuclear transport", J. Cell Biol. 113, 1991, 705-715.

Fresco, et al., "Conditional mutants of the yeast mRNA capping enzyme show that the cap enhances, but is not required for, mRNA splicing", RNA 2, 1996, 584-596.

Frias-Lopez, et al., "Microbial community gene expression in ocean surface waters", PNAS 105, 2008, 3805-3810.

Fromont-Racine, et al., "A highly sensitive method for mapping the 5' termini of mRNAs", NAR 21, 1993, 1683-1684.

Gershon, "(a)-tail of two polymerase structures", Nature Structural Biol. 7, 2000, 819-821.

Green, et al., "Human beta-blobin pre-mRNA synthesized in vitro is accurately spliced in Xenopus oocyte nuclei", Cell 32, 1983, 681-694.

Gross, et al., "Characterization of a Baculovirus-Encoded RNA 5'-Triphosphatase", Virology 72, 1998, 7057-7063.

Gumport, et al., "T4 RNA ligase as a nucleic acid synthesis and modification reagent", Gene Amplif Anal 2, 1981, 313-345.

Gunawardana, et al., "Identification of functional domains in Arabidopsis thaliana mRNA decapping enzyme (AtDcp2)", NAR 36, 2008, 203-216.

Hamm, et al., "The trimethylguanosine cap structure of U1 snRNA is a component of a bipartite nuclear targeting signal", Cell 62, 1990, 569-577.

Hausmann, "Bacteriophage T7 genetics", Current Topics in Microbiology and Immunology 75, 1976, 77-110.

Higman, et al., "The mRNA (guanine-7-)methyltransferase domain of the vaccinia virus mRNA capping enzyme. Expression in Eschericia coli and structural and kinetic comparison to the intact capping enzyme", J Biol Chem 269, 1994, 14974-14981.

Higman, et al., "The vaccinia virus mRNA (guanine-N7-)-methyltransferase requires both subunits of the mRNA capping enzyme for activity", J Biol Chem 267, 1992, 16430-16437.

Ho, et al., "Bacteriophage T4 RNA ligase 2 (gp24.1) exemplifies a family of RNA ligases found in all phylogenetic domains", PNAS 99, 2002, 12709-12714.

Iwasaki, et al., "Characterization of Arabidopsis decapping proteins AtDCP1 and AtDCP2, which are essential for post-embryonic development", FEBS Lett 581, 2007, 2455-2459.

Kazmierczak, et al., "The phage N4 virion RNA polymerase catalytic domain is related to single-subunit RNA polymerases", EMBO J., 21, 2002, 5815-5823.

Korsten, et al., "The strategy of infection as a criterion for phylogenetic relationships of non-coli phages morphologically similar to phage T7", Journal of General Virology 43, 1979, 57-73.

Krieg, et al., "Functional messenger RNAs are produced by SP6 in vitro transcription of cloned cDNAs", NAR 12, 1984, 7057.

Kwak, et al., "A family of poly(U) polymerases", RNA 13, 2007, 860-867.

Liu, et al., "Mapping the 5' and 3' ends of Tetrahymena thermophila mRNAs using RNA ligase medated amplifiaction of cDNA ends (RLM-RACE)", Nucleic Acids Research, vol. 21 No. 21, 1993, 4954-4960.

Martin, et al., "Purification of mRNA guanylyltransferase and mRNA (guanine-7-) methyltransferase from vaccinia virions", The Journal of Biological Chemistry 250 (24), 1975, 9322-9329.

Maruyama, et al., "Oligo-capping: a simple method to replace the cap structure of eukaryotic mRNAs with oligoribonucleotides", Gene 137, 1994, 171-174.

Mattaj, "Cap trimethylation of U snRNA is cytoplasmic and dependent on U snFNP protein binding", Cell 46, 1986, 905-911.

Myette, et al., "Domain structure of the vaccinia virus mRNA capping enzyme. Expression in Eschericia coli of the subdomain possessing the RNA 5'-triphosphatase and guanylyltransferase activities and a kinetic comparison to the full-size enzyme", The Journal of Biological Chemistry 271, 1996, 11936.

Padilla, et al., "A Y639F/H784A T7 RNA polymerase double mutant displays superior properties for synthesizing RNAs with non-canonical NTPs", NAR 30, 2002, e138.

Parrish, et al., "Characterization of a second vaccinia virus mRNA-decapping enzyme conserved in poxviruses", Journal of Virology 81, 2007, 12973-12978.

Parrish, et al., "Vaccinia virus D10 protein has mRNA decapping activity, providing a mechanism for control of host and viral gene expression", PNAS 104, 2007, 2139-2144.

Piccirillo, et al., "Functional characterization of the mammalian mRNA decapping enzyme hDcp2", RNA 9, 2003, 1138-1147.

Rinn, et al., "Functional demarcation of active and silent chromatin domains in human HOX loci by noncoding RNAs", Cell 29, 2007, 1311-23.

Romaniuk, et al., "Joining of RNA molecules with RNA ligase", Methods Enzymol 100, 1983, 52-59.

Romaniuk, et al., "The effect of acceptor oligoribonucleotide sequence on the T4 RNA ligase reaction", Eur J Biochem 125, 1982, 639-649.

Ross, "Messenger RNA turnover in eukaryotic cells", Mol. Biol. Med. 5, 1988, 1-14.

Schwer, et al., "Accelerated mRNA decay in conditional mutants of yeast mRNA capping enzyme", NAR 26, 1998, 2050-2057.

Schwer, et al., "Conditional inactivation of mRNA capping enzyme affects yeast pre-mRNA splicing in vivo", RNA 2, 1996, 574-583.

Shuman, "Capping enzyme in eukaryotic mRNA synthesis", Progress in Nucleic Acid Research and Molecular Biology 50, 1995, 101-129.

Shuman, et al., "Purification and characterization of a GTP-pyrophosphate exchange activity from vaccinia virions. Association of the GTP-pyrophosphate exchange activity with vaccinia mRNA guanylyltransferase", The Journal of Biological Chemistry 255, 1980, 11588-11598.

Shuman, "Structure, mechanism, and evolution of the mRNA capping apparatus", Prog Nucleic Acid Res Mol Biol 66, 2001, 1-40.

Sousa, et al., "T7 RNA polymerase", Prog Nucleic Acid Res Mol Biol., 73, 2003, 1-41.

Steiger, et al., "Analysis of recombinant yeast decapping enzyme", RNA 9, 2003, 231-238.

Stevens, A. et al., "5'-exonucliease-2 of Saccharomyces cerevisiae. Purification and features of ribonuclease activity with comparison to 5'-exonuclease-1", The Journal of Biological Chemistry, vol. 270, No. 27, Jul. 7, 1995, 16063-16069.

Suzuki, et al., "Construction and characterization of a full length-enriched and a 5'-end-enriched cDNA library", Gene 200, 1997, 149-156.

Suzuki, et al., "Construction of full-length-enriched cDNA libraries. The oligo-capping method.", Methods in Mol Biol 175, 2001, 143-153.

Takagi, et al., "A protein tyrosine phosphatase-like protein from baculovirus has RNA 5'-triphosphatase and diphosphatase activities", PNAS 95, 1998, 9808-9812.

Towle, et al., "Purification and characterization of bacteriophage gh-l-induced deoxyribonucleic acid-dependent ribonucleic acid polymerase from *Pseudomonas putida*", J. Biol. Chem, 250, 1975, 1723-1733.

Uhlenbeck, et al., "2 T4 RNA Ligase", The Enzymes vol. XV, Boyer ed., Academic Press, New York, 1982, 31-58.

Van Dijk, "Human Dcp2: a catalytically active mRNA decapping enzyme located in specific cytoplasmic structures", EMBO J 21, 2002, 6915-6924.

Van Gelder, et al., "Amplified RNA synthesized from limited quantities of heterogenous cDNA", PNAS 87, 1990, 1663-1667.

Wang, "Phylogeny of mRNA capping enzymes", PNAS 94, 1997, 9573-9578.

Wilusz, et al., "A 64 kd nuclear protein binds to RNA segments that include the AAuAAA polyadenylation motif", Cell 52, 1988, 221.

* cited by examiner

Examples of Reactions Catalyzed by RNA 5' Polyphosphatase

N = RNA, DNA, NTPs, NDPs, dNTPs, dNDPs

FIGURE 2

Activities of Enzymes on RNA Substrates that Have Different 5' End Groups

| RNA SUBSTRATE 5' END GROUP: | ACTIVITY (+ or -) ON AN RNA SUBSTRATE THAT HAS THE INDICATED 5' END GROUP | | | | | | |
|---|---|---|---|---|---|---|---|
| | TAP | Decapping Enzyme | AP | RPP | RMP | XRN | RNA Ligase + Acceptor Oligo |
| 1. 7<sup>me</sup>GpppN........ example: Eukaryotic Capped RNA | + | + | − | − | − | − | − |
| 2. pppN........ examples: Bacterial mRNA and Eukaryotic Organellar Transcripts | + | − | + | + | − | − | − |
| 3. pN........ example: miRNA | − | − | + | − | + | + | + |
| 4. HO-N........ example: degraded RNA | − | − | − | − | − | − | − |

+ signifies that the indicated enzyme modifies the RNA

− signifies that the indicated enzyme does not modify the RNA

FIGURE 3

Reaction with RNA Substrates by the Enzymes Indicated in FIG 2.

| SUBSTRATE | ENZYME | PRODUCTS |
|---|---|---|
| 1. $7^{me}GpppN....$ | TAP | $pN..... + 7^{me}GMP + 2 Pi$ |
| $7^{me}GpppN....$ | Decapping Enz | $pN..... + 7^{me}GMP + 2 Pi$ |
| 2. $pppN....$ | Decapping Enz | $pppN.....$ (no rxn) |
| $pppN....$ | Capping Enz | $7^{me}GpppN....$ |
| $pppN....$ | RPP | $pN..... + 2Pi$ |
| $pppN....$ | TAP | $pN..... + 2Pi$ |
| $pppN....$ | AP | $HON.... + 3Pi$ |
| 3. $pN....$ | RMP | $HON.... + Pi$ |
| $pN....$ | AP | $HON.... + Pi$ |
| $pN....$ | XRN | 5'NMPs |
| $pN....c.$ | RNA ligase + RNA acceptor | acceptor RNA-N...... |

FIGURE 4

DNA and Amino Acid Sequences of *E. coli* RNA 5' Polyphosphatase

SEQ ID NO: 1: DNA Sequence of *E. coli* RNA 5' Polyphosphatase
The DNA sequence for the first 4 amino acids of amino terminus of the ~24-kD
protein and the ~19-kD protein are in italics or underlined, respectively.

*ATGTTAGCTTTT*GCCGCTCTTCGTTGAAGTCAAAAAATATATCATCATT
TTACTGGCGCTCGCTGCAATTGCCGGACTGGGTACTCATGCCGCCTGGA
GT<u>AGCAATGGTTTG</u>CCACGTATCGACAATAAAACACTGGCCAGACTGGC
ACAGCAGCACCCGGTTGTCGTTTTGTTTCGTCATGCTGAACGTTGCGAC
CGTTCAACCAATCAATGCTTGTCAGATAAAACAGGTATTACGGTTAAAGG
TACCCAGGATGCCCGTGAACTGGGCAACGCTTTTAGTGCTGATATCCCT
GATTTCGATCTTTATTCCAGTAATACCGTCCGGACCATTCAGTCGGCTAC
CTGGTTTTCAGCGGGTAAAAAATTGACGGTAGATAAACGACTTCTTCAGT
GCGGTAATGAGATTTATAGTGCAATTAAGGACTTACAAAGCAAAGCGCC
TGATAAAAATATCGTTATTTTCACCCATAATCATTGCCTGACATATATTG
CTAAAGATAAGCGTGACGCGACATTTAAACCTGATTATCTGGATGGTTTA
GTCATGCATGTGGAAAAAGGCAAAGTTTATCTGGATGGGGAATTCGTTA
ACCACTAA

SEQ ID NO: 2: Translated Amino Acid Sequence of *E. coli* RNA 5' Polyphosphatase
The first 4 amino acids of the amino terminus of the ~24-kD protein and
the ~19-kD protein are in italics or underlined, respectively.

*MLAF*CRSSLKSKKYIILLALAAIAGLGTHAAWS<u>SNGL</u>PRIDNKTLARLAQQH
PVVVLFRHAERCDRSTNQCLSDKTGITVKGTQDARELGNAFSADIPDFDLYS
SNTVRTIQSATWFSAGKKLTVDKRLLQCGNEIYSAIKDLQSKAPDKNIVIFTH
NHCLTYIAKDKRDATFKPDYLDGLVMHVEKGKVYLDGEFVNH

US 8,309,335 B2

SELECTIVE 5' LIGATION TAGGING OF RNA

CROSS-REFERENCE TO RELATED APPLICATIONS

The present application is a divisional application of U.S. Ser. No. 12/707,243, filed Feb. 17, 2010, which is a continuation-in-part of pending International Patent Application Ser. No. PCT/US2008/073305, International Filing Date Aug. 15, 2008, which claims priority to expired U.S. Provisional Patent Application Ser. No. 60/956,536, filed Aug. 17, 2007. The present application is also a continuation-in-part of pending International Patent Application Ser. No. PCT/US2009/042723, International Filing Date May 4, 2009, which claims priority to expired U.S. Provisional Patent Application Ser. No. 61/050,046, filed May 2, 2008, all of which are herein incorporated by reference in their entireties.

FIELD OF THE INVENTION

The invention relates to novel methods, compositions, and kits for selectively tagging the 5'-ends of one or more desired classes or types of RNA molecules, wherein each class is composed of the RNA molecules that have a particular chemical moiety or group on the 5'-position of their 5'-nucleotides. Some of the methods use a new class of enzymes discovered by the applicants called RNA 5' polyphosphatases (RPP). These enzymes specifically convert RNAs that have a 5'-polyphosphate group, but not 5'-capped RNA, to RNAs that have a 5'-monophosphate group. Some novel methods discovered by the applicants also use another novel class of enzymes, called RNA 5' monophosphatases (RMP), that convert RNAs that have a 5' monophosphate group, but not RNAs that have a 5' polyphosphate group, to RNAs that have a 5' hydroxyl group. Still other methods use RPP, RMP, and/or other enzymes, including capping enzymes, decapping enzymes, and nucleic acid pyrophosphatases, alone or sequentially in combination, to provide new methods for selective 5'-ligation tagging of desired classes of RNA molecules. The methods, compositions and kits are useful, for example, for research, human or non-human diagnostics, or therapeutics.

BACKGROUND OF THE INVENTION

Recent studies have shown that almost all parts of the human genome, including even so-called "non-coding regions", are transcribed into RNA (e.g., see Genome Research Volume 17, Issue 6: June 2007). As a result, there is currently great interest in identifying, characterizing and determining the biological fate and functions of all transcribed RNAs, including mRNAs, non-coding RNAs, such as microRNAs (miRNAs) or their pri-miRNA or pre-miRNA precursors, and other RNA molecules, including those which have not been identified.

There is also continuing interest to identify and analyze expression of various RNA molecules in order to understand differentiation, biological responses to environment, and other biological processes in normal and abnormal cells in eukaryotes. For example, there is great interest to study disease-related RNA molecules in eukaryotic cells in order to understand the initiation and progression of each disease and, hopefully, to find treatments or ways to prevent the disease or the disease progression.

With respect to diseases of eukaryotes caused by pathogenic bacteria, mycoplasma, and viruses, there is great interest to identify, characterize and determine the biological functions of RNAs encoded by genomes of both the host and the pathogen during the course of infection, disease initiation, and disease progression.

The nature of the 5' ends of different classes of RNA molecules plays an important role in their biological structure and function. The chemical moieties on the 5' ends of an RNA molecules influence their structure, stability, biochemical processing, transport, biological function and fate in a cell or organism. The chemical moieties commonly found at the 5' ends of different RNA classes include triphosphates, monophosphates, hydroxyls, and cap nucleotides. The particular chemical moiety on the 5' end provides important clues to the origin, processing, maturation and stability of the RNA. Characterization of this moiety in a newly identified RNA could even suggest a role for the RNA in the cell. Therefore, methods that can discriminate between classes of RNA molecules that contain different 5' end groups are important tools for characterizing, studying, and manipulating RNA.

For example, bacterial mRNAs typically have a triphosphate group on their 5' ends. Still further, many eukaryotic RNAs that are not translated into protein, referred to as "non-coding RNAs" or "ncRNAs," have been described, and many of these ncRNAs have a 5' triphosphate group. In addition, small prokaryotic and eukaryotic ribosomal RNAs (e.g., 5S or 5.8S rRNAs), and transfer RNAs (tRNAs) typically have a 5' triphosphate group.

Most eukaryotic cellular mRNAs and most eukaryotic viral mRNA transcripts are "capped" at their 5' terminus. A "cap" or "cap nucleotide" consists of a guanine nucleoside that is joined via its 5'-carbon to a triphosphate group that is, in turn, joined to the 5'-carbon of the most 5'-nucleotide of the primary mRNA transcript, and in most eukaryotes, the nitrogen at the 7 position of guanine in the cap nucleotide is methylated. Thus, most eukaryotic cellular mRNAs and most eukaryotic viral mRNAs have an "$N^7$-methylguanosine" or "$m^7G$" cap or cap nucleotide on their 5' ends.

In addition to eukaryotic cellular and viral mRNAs, some ncRNAs are also capped, and some capped ncRNAs also have a 3' poly(A) tail, like most eukaryotic mRNAs. For example, Rinn, J L et al. (Cell 129: 1311-1323, 2007) described one capped and polyadenylated 2.2-kilobase ncRNA encoded in the HOXC region of human chromosome 12, termed "HOTAIR," that has profound effects on expression of HOXD genes on chromosome 2. In addition, some other eukaryotic RNAs in a sample, such as small nuclear RNAs ("snRNAs"), and pre-miRNAs, can be capped.

The 5' caps of eukaryotic cellular and viral mRNAs (and some other forms of RNA) play important roles in mRNA metabolism, and are required to varying degrees for processing and maturation of an mRNA transcript in the nucleus, transport of mRNA from the nucleus to the cytoplasm, mRNA stability, and efficient translation of the mRNA to protein. For example, the cap plays a pivotal role in the initiation of protein synthesis and in eukaryotic mRNA processing and stability in vivo. The cap provides resistance to 5' exoribonuclease (XRN) activity and its absence results in rapid degradation of the mRNA (e.g., see Mol. Biol. Med. 5: 1-14, 1988; Cell 32: 681-694, 1983). Thus, mRNA prepared (e.g., in vitro) for introduction (e.g., via microinjection into oocytes or transfection into cells) and expression in eukaryotic cells should be capped.

Many eukaryotic viral RNAs are infectious only when capped, and when RNA molecules that are not capped (i.e., they are "uncapped") are introduced into cells via transfection or microinjection, they are rapidly degraded by cellular RNases (e.g., see Krieg, and Melton, Nucleic Acids Res. 12: 7057, 1984; Drummond, et al. Nucleic Acids Res. 13: 7375, 1979).

The primary transcripts of many eukaryotic cellular genes and eukaryotic viral genes require processing to remove intervening sequences (introns) within the coding regions of these transcripts, and the benefits of the cap also extend to stabilization of such pre-mRNA. For example, it was shown that the presence of a cap on pre-mRNA enhanced in vivo splicing of pre-mRNA in yeast, but was not required for splicing, either in vivo or using in vitro yeast splicing systems (Fresco, L D and Buratowski, S, RNA 2: 584-596, 1996; Schwer, B et al., Nucleic Acids Res. 26: 2050-2057, 1998; Schwer, B and Shuman, S, RNA 2: 574-583, 1996). The enhancement of splicing was primarily due to the increased stability of the pre-mRNA since, in the absence of a cap, the pre-mRNA was rapidly degraded by 5' exoribonuclease (Schwer, B, Nucleic Acids Res. 26: 2050-2057, 1998). Thus, it is also beneficial that transcripts synthesized for in vitro RNA splicing experiments are capped.

While capped mRNA remains in the cytoplasm after being exported from the nucleus, some other RNAs, such as some snRNAs have caps that are further methylated and then imported back into the nucleus, where they are involved in splicing of introns from pre-mRNA to generate mRNA exons (Mattaj, Cell 46: 905-911, 1986; Hamm et al., Cell 62: 569-577, 1990; Fischer, et al., J. Cell Biol. 113: 705-714, 1991).

The splicing reaction generates spiced intron RNA that initially comprises RNA that has a 5' monophosphate group. Thus, at least some initially-generated intron RNA molecules from pre-mRNA splicing reactions also have a 5' phosphate group. In addition, some other RNAs, such as eukaryotic or viral-encoded micro RNAs (miRNAs), and both eukaryotic and prokaryotic large ribosomal RNA molecules (rRNA), including 18S and 26S or 28S eukaryotic rRNAs, or 16S and 23S prokaryotic rRNAs, have a monophosphate group on their 5' ends.

RNase A-degraded RNAs and some other endonucleolytically processed RNA molecules have a 5' hydroxyl group.

Enzymes that modify the 5' ends of RNA are useful tools for characterizing and manipulating various RNA molecules in vitro. For example, alkaline phosphatase (AP) (e.g., APEX™ alkaline phosphatase (EPICENTRE), shrimp alkaline phosphatase (USB, Cleveland, Ohio), or Arctic alkaline phosphatase (New England Biolabs, MA) converts the 5' triphosphates of uncapped primary RNA and the 5' monophosphates of rRNA to 5' hydroxyl groups, generating RNAs that have a 5' hydroxyl group, but does not affect capped RNA. Nucleic acid pyrophosphatase (PPase) (e.g., tobacco acid pyrophosphatase (TAP)) cleaves the triphosphate groups of both capped and uncapped RNAs to synthesize RNAs that have a 5' monophosphate group. A decapping enzyme (e.g., yeast decapping enzyme, mammalian decapping enzyme, *Arabidopsis thaliana* decapping enzyme, or vaccinia virus decapping enzymes D9 or D10) converts capped RNA (e.g., $m^7G$-capped RNA) to RNA that has a 5' monophosphate group. A capping enzyme (e.g., SCRIPTCAP™ capping enzyme, EPICENTRE; poxvirus capping enzyme; vaccinia virus capping enzyme; or *Saccharomyces cerevisiae* capping enzyme RNA triphosphatase) converts RNA that has a 5' triphosphate group or RNA that has a 5' diphosphate group to capped RNA. Polynucleotide kinase (PNK; e.g., T4 PNK) monophosphorylates hydroxyl groups on the 5' ends of RNA molecules and removes monophosphate groups on the 3' ends of RNA molecules (e.g., 3' monophosphates generated from the action of RNase A). Further, 5' exoribonuclease (XRN; e.g., *Saccharomyces cerevisiae* Xrn I exoribonuclease) digests 5'-monophosphorylated RNA to mononucleotides, but generally does not digest RNA that has a 5' triphosphate, 5' cap, or 5' hydroxyl group.

The reaction specificity of RNA ligase can also be a useful tool to discriminate between RNA molecules that have different 5' end groups. This enzyme catalyzes phosphodiester bond formation specifically between a 5' monophosphate in a donor RNA and a 3'-hydroxyl group in an acceptor oligonucleotide (e.g., an RNA acceptor oligonucleotide). Thus, RNAs that have a monophosphate group on their 5' ends, whether present in a sample or obtained by treatment of 5'-triphosphorylated or 5'-capped RNA with TAP, are donor substrates for ligation to an acceptor nucleic acid that has a 3' hydroxyl group using RNA ligase. RNA molecules that contain triphosphate, diphosphate, hydroxyl or capped 5' end groups do not function as donor molecules for RNA ligase (e.g., T4 RNA ligase, EPICENTRE, or bacteriophage TS2126 RNA ligase). Thus, RNAs that have a hydroxyl group on their 5' ends, whether present in a sample or obtained by treatment with AP, cannot serve as donor substrates for RNA ligase (e.g., T4 RNA ligase, EPICENTRE, or bacteriophage TS2126 RNA ligase). Similarly, RNA molecules that contain a 3'-terminal blocked group (e.g., RNA molecules that have a 3'-phosphate group or a 3'-beta-methoxyphenylphosphate group) do not function as acceptor substrates for RNA ligase.

Numerous publications disclose use of alkaline phosphatase (AP), tobacco acid pyrophosphatase (TAP), and RNA ligase to manipulate $m^7G$-capped eukaryotic mRNAs using so-called "oligo capping methods." For example, oligo capping methods and their use are disclosed in: World Patent Applications WO0104286; and WO 2007/117039 A1; U.S. Pat. No. 5,597,713; Suzuki, Y et al., Gene 200: 149-156, 1997; Suzuki, Y and Sugano, S, Methods in Molecular Biology, 175: 143-153, 2001, ed. by Starkey, M P and Elaswarapu, R, Humana Press, Totowa, N.J.; Fromont-Racine, M et al., Nucleic Acids Res. 21: 1683-4, 1993; and in Maruyama, K and Sugano, S, Gene 138: 171-174, 1994.

In those oligo capping methods, total eukaryotic RNA or isolated polyadenylated RNA is first treated with AP and then the AP is inactivated or removed. The AP converts RNA that has a 5' triphosphate (e.g., uncapped primary RNA) and RNA that has a 5' monophosphate to RNA that has a 5' hydroxyl. The sample is then treated with TAP, which converts the 5'-capped eukaryotic mRNA to mRNA that has a 5' monophosphate. The resulting 5'-monophosphorylated mRNA is then "oligo-capped" (or "5' ligation tagged") with an acceptor oligonucleotide using RNA ligase. The "oligo-capped" mRNA that has a "tag" joined to its 5' end in turn serves as a template for synthesis of first-strand cDNA that has a tag joined to its 3' end. Then, double-stranded cDNA can be made using a second-strand cDNA synthesis primer that is complementary to the tag joined to the 3' end of the first-strand cDNA, and the resulting double-stranded cDNA can be used (e.g., to generate a full-length cDNA library). Oligo capping methods in the art are useful for 5' ligation tagging of $m^7G$-capped RNA, for making full-length first-strand cDNA using the 5'-ligation-tagged RNA as a template, for making full-length double-stranded cDNA (including full-length cDNA libraries), and for identification of the 5' ends of eukaryotic mRNA (e.g., by sequencing or methods such as random amplification of cDNA ends (5'RACE).

However, one problem with the oligo capping and other methods presently in the art is that the AP step converts the 5' ends of all RNA molecules that have a 5' triphosphate or a 5' monophosphate group to a 5' hydroxyl group (e.g., see FIG. 2 of World Patent Applications WO0104286). Thus, although the AP step is beneficial for some applications because it results in dephosphorylation of 5'-monophosphorylated RNA molecules (e.g., miRNA) so they cannot serve as donors for ligation to the acceptor oligonucleotide by RNA ligase, the AP step also results in dephosphorylation of uncapped mRNA molecules and uncapped non-coding primary RNA molecules (which may have functional significance) so they cannot serve as a donors for ligation to the acceptor oligonucleotide. What is needed in the art are methods for selectively 5' ligation tagging 5'-triphosphorylated uncapped RNA molecules, such as uncapped mRNA and non-coding primary RNA, in the sample, and for converting said 5'-ligation-tagged RNA molecules to cDNA, without also 5' ligation tagging 5'-monophosphorylated RNA molecules in the sample.

In addition, what is needed in the art are methods for selectively dephosphorylating those RNA molecules in a sample that have a 5' monophosphate group without also removing the 5' triphosphate group from primary RNA transcripts. What is needed are methods, compositions, and kits that employ an enzyme composition that is capable of selectively digesting a 5' monophosphate group of undesired RNA to a 5' hydroxyl group so that the undesired RNA will not be 5' ligation tagged by the acceptor oligonucleotide. Thus, what is needed are methods, compositions, and kits that employ an RNA 5' monophosphatase enzyme composition.

Still further, although the methods known in the art can be used for selective 5' ligation tagging of $m^7G$-capped RNA molecules, there is currently no good method in the art for selective 5' ligation tagging of only uncapped primary RNA molecules in a sample that also contains capped RNA molecules. This is regrettable because it would be desirable to specifically oligo cap (or "5' ligation tag") and study the uncapped eukaryotic primary RNAs that are believed to play a role in cellular biological activities, including regulation of gene expression. What is further needed in the art is a method for selective 5' ligation tagging of uncapped eukaryotic primary RNA molecules in a sample that also contains capped eukaryotic RNA molecules.

It is further regrettable that there is currently no good method in the art for selective 5' ligation tagging of only uncapped primary RNA molecules in samples that also contain capped RNA molecules because, in general, bacterial mRNA molecules are not capped. Thus, it is difficult to study the expression of genes of pathogenic (e.g., mycoplasma) or symbiotic (e.g., *Rhizobium*) prokaryotes that are associated with eukaryotic cells. What is needed in the art are methods for selective 5' ligation tagging of 5'-polyphosphorylated RNA of prokaryotes, including uncapped primary RNA molecules of bacteria or mycoplasma that are present or associated with eukaryotic cells, such as pathogenic or symbiotic prokaryotes in association with eukaryotic cells, without also 5' ligation tagging capped eukaryotic mRNA molecules (e.g., to study prokaryotic gene expression during pathogenic or symbiotic processes).

What is further needed in the art are methods for selective 5' ligation tagging of primary prokaryotic RNA molecules in samples from diverse environments (e.g., from soils, oceans, lakes, rivers, and other environments, including those with different or extreme conditions of temperature, pH, content of elements or chemicals, or other properties) in order to obtain, identify, characterize, clone, express, study, and exploit those RNA molecules for practical purposes (e.g., for identifying RNA transcripts to express enzymes or proteins with medical or industrial applications). By way of example, what is needed are 5' ligation tagging methods that are easier, more efficient and that provide more and better data for metatranscriptomic surveys and research than methods known in the art (e.g., the methods described by J. Frias-Lopez et al., Proc. Natl. Acad. Sci. USA 105: 3805-3810, 2008).

Thus, what is needed in the art are methods for selective 5' ligation tagging of desired RNA molecules without also 5' ligation tagging undesired RNA molecules in the sample (e.g., for selective 5' ligation tagging of uncapped primary RNA molecules but not capped RNA molecules in samples that contain both uncapped and capped RNA).

Prior to the present invention, no methods were known in the art for using an enzyme that would selectively digest the 5' triphosphate of primary RNA, such as uncapped eukaryotic primary RNA or bacterial mRNA, to a 5' monophosphate without also digesting capped eukaryotic mRNA. Thus, oligo capping methods known in the art could not be used for selectively synthesizing cDNA from uncapped eukaryotic primary RNA and/or full-length prokaryotic mRNA, for cloning cDNA prepared from uncapped full-length eukaryotic primary RNA and/or prokaryotic mRNA, for RNA amplification of uncapped full-length eukaryotic primary RNA and/or prokaryotic mRNA, or for capture and identification of the exact 5' ends of uncapped full-length eukaryotic primary RNA and/or prokaryotic primary mRNA in samples that also contained capped RNA molecules. What is needed in the art are methods, compositions, and kits that employ an enzyme composition that is capable of digesting a 5' triphosphate group of an uncapped primary RNA to a monophosphate under conditions wherein said enzyme composition does not digest the 5' end of RNA that is capped. Thus, what is needed are methods, compositions, and kits that employ an RNA 5' polyphosphatase enzyme composition.

What is needed in the art are methods, compositions, and kits that employ an RNA 5' polyphosphatase enzyme composition and/or an RNA 5' monophosphatase enzyme composition, including in combination with one or more other enzymes known in the art, for 5' ligation tagging of any desired population of RNA molecules with an acceptor oligonucleotide using RNA ligase, for synthesizing cDNA from full-length desired RNA (e.g., full-length capped eukaryotic RNA, full-length uncapped eukaryotic primary RNA, and/or full-length prokaryotic primary mRNA) and for cloning said cDNA, for RNA amplification of said desired RNA, and for capture and identification of the exact 5' ends of said desired RNA (e.g., by sequencing, or by using methods such as random amplification of cDNA ends (RACE), exon arrays, or other microarrays). What is needed are better and more efficient methods for making tagged DNA fragments from specific types of RNA molecules in samples for use in nucleic acid amplification, for making labeled target for expression analysis (e.g., using microarrays or qPCR) and for use as templates for next-generation sequencing.

SUMMARY OF THE INVENTION

In some embodiments, the present invention provides methods for 5' ligation tagging of uncapped RNA in a sample that has a 5' polyphosphate group, comprising: (A) providing: (i) a sample that contains uncapped RNA that has a 5' polyphosphate group, including wherein the sample additionally contains RNA that has a 5' monophosphate group and/or capped RNA and/or RNA that has a 5' hydroxyl group; (ii) RNA 5' polyphosphatase; (iii) an acceptor oligonucleotide that exhibits a tag; and (iv) RNA ligase; (B) contacting the sample with the RNA 5' polyphosphatase under conditions and for sufficient time wherein the uncapped RNA that has a 5' polyphosphate group is converted to RNA that has a 5' monophosphate group; and (C) contacting the sample from step (B) with the acceptor oligonucleotide and the RNA ligase under conditions and for sufficient time wherein the 3' end of the acceptor oligonucleotide is ligated to RNA that has a 5' monophosphate group but not to the capped RNA and 5'-ligation-tagged RNA is generated.

In other embodiments, the present invention provides the sample provided in step (A) additionally contains RNA that has a 5' monophosphate group but the acceptor oligonucleotide is only ligated to the RNA that has a 5' monophosphate group which was converted from the uncapped RNA that has a 5' polyphosphate group in step (B) and is not ligated to the RNA that has a 5' monophosphate group already in the sample provided in step (A), wherein the method additionally comprises the substeps of: providing an RNA 5' monophosphatase; and, prior to step (B), contacting the sample with the RNA 5' monophosphatase under conditions and for sufficient time wherein RNA in the sample that has a 5' monophosphate group is converted to RNA that has a 5' hydroxyl group; and inactivating or removing the RNA 5' monophosphatase.

In other embodiments, the method additionally comprises 5' ligation tagging of the capped RNA in the sample, wherein the method additionally comprises the substeps of: providing a nucleic acid pyrophosphatase or decapping enzyme; and, prior to step (C), contacting the sample from step (B) with the nucleic acid pyrophosphatase or the decapping enzyme under conditions and for sufficient time wherein capped RNA in the sample is converted to RNA that has a 5' monophosphate group, whereby the capped RNA contained in the sample provided in step (A) is also 5'-ligation tagged in step (C).

In some embodiments, the present invention provides methods for 5' ligation tagging of capped RNA in a sample, the method comprising the steps of: (A) providing: (i) a sample that contains capped RNA, and, optionally, uncapped RNA that has a 5' polyphosphate group, and/or RNA that has a 5' monophosphate group; and/or RNA that has a 5' hydroxyl group, (ii) RNA 5' polyphosphatase; (iii) RNA 5' monophosphatase; (iv) a nucleic acid pyrophosphatase or decapping enzyme; (v) an acceptor oligonucleotide; and (vi) RNA ligase; (B) contacting the sample with the RNA 5' polyphosphatase under conditions and for sufficient time wherein the uncapped RNA that has a 5' polyphosphate group is converted to RNA that has a 5' monophosphate group; (C) contacting the sample from step (B) with the RNA 5' monophosphatase under conditions and for sufficient time wherein RNA that has a 5' monophosphate group is converted to RNA that has a 5' hydroxyl group; (D) inactivating or removing the RNA 5' monophosphatase; (E) contacting the sample following step (D) with the nucleic acid pyrophosphatase or the decapping enzyme under conditions and for sufficient time wherein capped RNA in the sample is converted to RNA that has a 5' monophosphate group; (F) contacting the sample from step (E) with the acceptor oligonucleotide and the RNA ligase under conditions and for sufficient time wherein the 3' end of the acceptor oligonucleotide is ligated to the 5' end of the RNA that has a 5' monophosphate group that was generated in step (E) but is not ligated to the RNA that has a 5' monophosphate group which was converted from the uncapped RNA that has a 5' polyphosphate group in step (B) or to the RNA that has a 5' monophosphate group already in the sample provided in step (A), and 5'-ligation-tagged RNA is generated from the capped RNA.

In certain embodiments, the present invention provides methods for 5' ligation tagging of capped RNA and/or uncapped RNA that has a 5' polyphosphate group, comprising: (A) providing: (i) a sample that contains capped RNA and/or uncapped RNA that has a 5' polyphosphate group; (ii) nucleic acid pyrophosphatase; (iii) an acceptor oligonucleotide; and (iv) RNA ligase; (B) contacting the sample, wherein the sample has not been contacted with an alkaline phosphatase, with the nucleic acid pyrophosphatase under conditions and for sufficient time wherein the capped RNA and the uncapped RNA that has a 5' polyphosphate group are converted to RNA that has a 5' monophosphate group; (C) contacting the sample from step (B) with the acceptor oligonucleotide and the RNA ligase under conditions and for sufficient time wherein the 3' end of the acceptor oligonucleotide is ligated to the 5' end of the RNA that has a 5' monophosphate group and 5'-ligation-tagged RNA is generated.

In particular embodiments, the sample provided in step (A) additionally contains RNA that has a 5' monophosphate group, but the acceptor oligonucleotide is only ligated to the RNA that has a 5' monophosphate group which was converted from capped RNA and/or from the RNA that is uncapped and has a 5' polyphosphate group in step (B) and is not ligated to the RNA that has a 5' monophosphate group already in the sample provided in step (A), wherein the method additionally comprises the substeps of: providing an RNA 5' monophosphatase; and, prior to step (B), contacting the sample with the RNA 5' monophosphatase under conditions and for sufficient time wherein RNA in the sample that has a 5' monophosphate group is converted to RNA that has a 5' hydroxyl group; and inactivating or removing the RNA 5' monophosphatase.

In further embodiments, the present invention provides methods for 5' ligation tagging of uncapped RNA that has a 5' polyphosphate group in a sample without also 5' ligation tagging RNA in the sample that has a 5' monophosphate group, comprising: (A) providing: (i) a sample that contains at uncapped RNA that has a 5' polyphosphate group and RNA that has a 5' monophosphate group; (ii) a capping enzyme; (iii) an RNA 5' monophosphatase or alkaline phosphatase; (iv) a nucleic acid pyrophosphatase or decapping enzyme; (v) an acceptor oligonucleotide; and (vi) RNA ligase; (B) contacting the sample with the capping enzyme under conditions and for sufficient time wherein the uncapped RNA that has a 5' polyphosphate group is converted to capped RNA; (C) contacting the sample from step (B) with the RNA 5' monophosphatase or the alkaline phosphatase under conditions and for sufficient time wherein RNA that has a 5' monophosphate group is converted to RNA that has a 5' hydroxyl group; (D) inactivating or removing the RNA 5' monophosphatase or the alkaline phosphatase that was used in step (C); (E) contacting the sample following step (D) with the nucleic acid pyrophosphatase or the decapping enzyme under conditions and for sufficient time wherein capped RNA is converted to RNA that has a 5' monophosphate group; (F) contacting the sample from step (E) with the acceptor oligonucleotide and the RNA ligase under conditions and for sufficient time wherein the 3' end of the acceptor oligonucleotide is ligated to the 5' end of the RNA that has a 5' monophosphate group and 5'-ligation-tagged RNA is generated.

In some embodiments, the sample provided in step (A) additionally contains capped RNA, and wherein 5'-ligation-tagged RNA is generated both from the capped RNA provided in the sample of step (A) and from the uncapped RNA in the sample that has a 5' polyphosphate group which is capped in step (B).

In particular embodiments, the present invention provides methods for 5' ligation tagging capped RNA and RNA that has a 5' monophosphate group in a sample without also 5' ligation tagging uncapped RNA in the sample that has a 5' polyphosphate group, the method comprising the steps of: (A) providing: (i) a sample that contains at least capped RNA, uncapped RNA that has a 5' polyphosphate group and RNA that has a 5' monophosphate group; (ii) a decapping enzyme; (iii) an acceptor oligonucleotide; and (iv) RNA ligase; (B)

contacting the sample with the decapping enzyme under conditions and for sufficient time wherein capped RNA is converted to RNA that has a 5' monophosphate group; and (C) contacting the sample from step (B) with the acceptor oligonucleotide and the RNA ligase under conditions and for sufficient time wherein the 3' end of the acceptor oligonucleotide is ligated to the 5' end of the RNA that has a 5' monophosphate group and 5'-ligation-tagged RNA is generated.

In other embodiments, the present invention provides methods for 5' ligation tagging of capped RNA in a sample without also 5' ligation tagging uncapped RNA that has a 5' polyphosphate group or RNA that has a 5' monophosphate group, the method comprising the steps of: (A) providing: (i) a sample that contains at capped RNA, uncapped RNA that has a 5' polyphosphate group, RNA that has a 5' monophosphate group, and/or RNA that has a 5' hydroxyl group; (ii) an RNA 5' monophosphatase or alkaline phosphatase; (iii) a decapping enzyme; (iv) an acceptor oligonucleotide; and (v) RNA ligase; (B) contacting the sample with the RNA 5' monophosphatase or the alkaline phosphatase under conditions and for sufficient time wherein the respective enzyme is active and the reactions it catalyzes can go to completion; (C) inactivating or removing the RNA 5' monophosphatase or the alkaline phosphatase that was used in step (B); (D) contacting the sample from step (C) with the decapping enzyme under conditions and for sufficient time wherein capped RNA is converted to RNA that has a 5' monophosphate group; and (E) contacting the sample from step (D) with the acceptor oligonucleotide and the RNA ligase under conditions and for sufficient time wherein the 3' end of the acceptor oligonucleotide is ligated to the 5' end of the RNA that has a 5' monophosphate group that was generated from the capped RNA in step (D) and 5'-ligation-tagged RNA is generated.

In other embodiments, the method additionally comprises the steps of: providing a poly(A) polymerase and ATP; and contacting the sample with the poly(A) polymerase and ATP under conditions and for sufficient time wherein a poly(A) tail is added to the 3'-ends of the RNA molecules in the sample and RNA that has a poly(A) tail is generated.

In particular embodiments, the sample comprises a first sample that contains RNA derived from cells of a first type or a first condition or from a first environment, and wherein the method further comprises subtraction from the 5'-ligation-tagged RNA generated from the first sample those RNA molecules that are also present in a second sample derived from cells of a second type or a second condition or from a second environment, thereby generating a population of 5'-ligation-tagged RNA molecules derived from RNA that is present only in the first sample but absent in the second sample, the method comprising the steps of: (i) providing the 5'-ligation-tagged RNA generated from the first sample, and a second sample that contains RNA derived from cells of a second type or a second condition or from a second environment; (ii) preparing first-strand cDNA by reverse transcription of the RNA in the second sample; (iii) annealing to the 5'-ligation-tagged RNA generated from the first sample the first-strand cDNA prepared from the RNA from the second sample under conditions and for sufficient time wherein a hybridization complex is formed between the 5'-ligation-tagged RNA generated from the first sample and the first-strand cDNA prepared from RNA from the second sample; and (iv) treating the hybridization complex with the RNase H under conditions and for sufficient time wherein the RNA to which the cDNA is annealed is digested, and subtracted 5'-ligation-tagged RNA consisting of 5'-ligation-tagged RNA derived from RNA that is present only in the first sample but absent in the second sample is generated.

In further embodiments, the acceptor oligonucleotide that is provided in step (A) for generating 5'-ligation-tagged RNA from RNA in the first sample contains an affinity molecule, and the method further comprises the steps of: providing a solid surface to which an affinity-binding substance that is capable of binding the affinity molecule is attached; and, either prior to or after step (iv), contacting the 5'-ligation-tagged RNA generated from the first sample to the solid surface under conditions and for sufficient time wherein the 5'-ligation-tagged RNA from the first sample binds to the solid surface to which the affinity-binding substance is attached, and the 5'-ligation-tagged RNA derived from RNA in the first sample is captured on the solid surface.

In some embodiments, the method further comprises synthesizing first-strand cDNA from the 5'-ligation-tagged RNA, wherein the method additionally comprises the steps of: providing an RNA-dependent DNA polymerase; and contacting the 5'-ligation-tagged RNA with the RNA-dependent DNA polymerase under conditions and for sufficient time wherein first-strand cDNA that is complementary to the 5'-ligation-tagged RNA is synthesized; including wherein the method additionally comprises: providing a first-strand cDNA synthesis primer that is complementary to the 5'-ligation-tagged RNA and contacting the 5'-ligation-tagged RNA with the first-strand cDNA synthesis primer and the RNA-dependent DNA polymerase under conditions and for sufficient time wherein cDNA that is complementary to the 5'-ligation-tagged RNA is synthesized; such as wherein the first-strand cDNA synthesis primer comprises a sequence wherein at least its 3' end exhibits a sequence selected from the group consisting of: a sequence that is complementary to a homopolymeric sequence that was added post-transcriptionally, either in vivo in the cell or in vitro, to the 3' end of the RNA in the sample or to the 3' end of the 5'-ligation-tagged RNA; a sequence that is complementary to a known sequence at the 3' end of one or more RNA molecules; a sequence that is complementary to one or more internal regions of one or more RNA molecules; a collection of all possible sequences wherein each sequence is random; a sequence that is complementary to a poly(A) tail, selected from among an oligo(dT)n sequence, an oligo(dU)n sequence, an oligo(U)n sequence, an oligo(dT)nX anchored sequence, an oligo(dU)nX anchored sequence, and an oligo(U)nX anchored sequence; and a sequence that is complementary to an oligonucleotide tag that is added to the 3' end of the RNA in the sample or to the 3' end of the 5'-ligation-tagged RNA; and/or wherein the first-strand cDNA synthesis primer additionally exhibits a specific 5' sequence which is 5'-of the sequence exhibited at its 3' end, wherein the specific 5' sequence is capable of serving as a template for synthesis of second-strand cDNA that exhibits a specific 3' sequence that is complementary to the specific 5' sequence and that provides a site for specific priming of second-strand cDNA.

In particular embodiments, the method additionally comprises the steps of: providing RNase H and RNase I; and contacting the sample containing first-strand cDNA with the RNase H and the RNase I under conditions and for sufficient time wherein the RNA is digested. In other embodiments, the method additionally comprises the steps of: providing a DNA-dependent DNA polymerase; and contacting the first-strand cDNA with the DNA-dependent DNA polymerase under conditions and for sufficient time wherein double-stranded cDNA is synthesized; including wherein the method additionally comprises the steps of: providing a second-strand cDNA synthesis primer that is complementary to the portion of the first-strand cDNA that is complementary to the acceptor oligonucleotide provided in step (A), and a DNA-dependent DNA polymerase; and contacting the second-strand cDNA synthesis primer and the DNA-dependent DNA polymerase with the first-strand cDNA under conditions and for sufficient time wherein double-stranded cDNA is synthesized; wherein the DNA-dependent DNA polymerase is the same as the RNA-dependent DNA polymerase provided for synthesis of first-strand cDNA; or wherein the DNA-dependent DNA polymerase is different from the RNA-dependent DNA polymerase provided for synthesis of first-strand cDNA.

In particular embodiments, the 5' portion of the acceptor oligonucleotide, the 5'-portion of the first-strand cDNA synthesis primer or the 5'-portion of the second-strand cDNA synthesis primer exhibits a sequence for one strand of a double-stranded RNA polymerase promoter and the method further comprises the steps of: providing: an RNA polymerase that can synthesize RNA using the double-stranded RNA polymerase promoter for which a sequence for one strand is exhibited in the acceptor oligonucleotide, the first-strand cDNA synthesis primer, or the second-strand cDNA synthesis primer; and contacting the double-stranded cDNA with the RNA polymerase under conditions and for sufficient time wherein RNA is synthesized.

In some embodiments, the acceptor oligonucleotide, the first-strand cDNA primer, or the second-strand cDNA primer contains or is joined to an affinity molecule, and the method additionally comprises the steps of: providing a solid surface that is covalently or non-covalently coated with an affinity binding substance that is capable of specifically binding the affinity molecule; and, either prior to or following the step in which it is involved, contacting the acceptor oligonucleotide, the first-strand cDNA primer, or the second-strand cDNA primer that is chemically joined to the affinity molecule under conditions and for sufficient time wherein it binds to affinity binding substance that is joined to the solid surface.

In further embodiments, the respective 5'-ligation-tagged RNA, first-strand cDNA, or second-strand cDNA that is synthesized contains an affinity molecule and the 5'-ligation-tagged RNA, first-strand cDNA, or second-strand cDNA that contains the affinity molecule is captured, isolated or purified by binding it to the solid surface, the method comprising the steps of: contacting the 5'-ligation-tagged RNA, the first-strand cDNA, or the second-strand cDNA that contains the affinity molecule with the solid surface in the presence of reagents and under conditions that facilitate its binding to the affinity-binding substance that is attached to the solid surface, wherein the 5'-ligation-tagged RNA, the first-strand cDNA, or the second-strand cDNA that contains the affinity molecule is bound to the surface, thereby capturing, isolating, or purifying the 5'-ligation-tagged RNA, the first-strand cDNA, or the second-strand cDNA that contains the affinity molecule; including wherein the affinity molecule is biotin and the affinity binding substance is avidin or streptavidin, or wherein the affinity molecule is digoxigenin and the affinity binding substance is an antibody that specifically binds digoxigenin.

In some embodiments, the present invention provides kits for performing the methods of any of claims 1 through 26, wherein the kit comprises an RNA 5' polyphosphatase (RPP) and at least one other component selected from the group consisting of: an RNA 5' monophosphatase (RMP); an alkaline phosphatase (AP); a nucleic acid pyrophosphatase; a decapping enzyme; a capping enzyme; an ligase; an RNA acceptor oligonucleotide; a poly(A) polymerase; a poly(U) polymerase; an RNA-dependent DNA polymerase (RT); a first-strand cDNA synthesis primer; an RNase H; a second-strand cDNA synthesis primer; an RNA polymerase (RNAP); 5' exoribonuclease (Xrn); a polynucleotide kinase (PNK); and an RNA molecule that has a 5' triphosphate or diphosphate group wherein the beta or gamma phosphate of the group is labeled; or wherein the kit comprises RNA 5' monophosphatase (RMP) (e.g., RNA 5' monophosphatase 1 (RMP1, EPICENTRE) and at least one other component selected from the group consisting of: an RNA 5' polyphosphatase (e.g., an aluminum-inducible RNA 5' polyphosphatase, e.g., E. coli RNA 5' polyphosphatase I (RPP I), EPICENTRE, or Shigella RNA 5' polyphosphatase I); an alkaline phosphatase (e.g., APEX™ Alkaline Phosphatase (EPICENTRE), shrimp alkaline phosphatase (USB, Cleveland, Ohio), or Arctic Alkaline Phosphatase (New England Biolabs, MA); a nucleic acid pyrophosphatase (e.g., tobacco acid pyrophosphatase (TAP), EPICENTRE); a decapping enzyme (e.g., yeast decapping enzyme, mammalian decapping enzyme, Arabidopsis thaliana decapping enzyme, and poxvirus or vaccinia virus decapping enzyme (e.g., virus decapping enzymes D9 and D10)); a capping enzyme (e.g., poxvirus capping enzyme, Saccharomyces cerevisiae capping enzyme, or SCRIPTCAP™ capping enzyme kit, (EPICENTRE)); RNA ligase (e.g., T4 RNA ligase, EPICENTRE, or bacteriophage TS2126 RNA ligase); an RNA acceptor oligonucleotide; poly(A) polymerase (e.g., E. coli poly(A) polymerase, EPICENTRE); an RNA-dependent DNA polymerase (RT) (e.g., SUPERSCRIPT RT (Invitrogen, Carlsbad, Calif.), AMV RT, MMLV RT (EPICENTRE)); a first-strand cDNA synthesis primer; RNase H (e.g., E. coli RNase H or HYBRIDASE™ RNase H, EPICENTRE); a second-strand cDNA synthesis primer; an RNA polymerase (RNAP) (e.g., a T7-type RNAP, e.g., T7 RNAP, T3 RNAP, or SP6 RNAP, EPICENTRE); 5' exoribonuclease (e.g., TERMINATOR™ 5'-phosphate-dependent exonuclease or Saccharomyces cerevisae Xrn I exoribonuclease (Xrn I), EPICENTRE); polynucleotide kinase (PNK) (e.g., T4 PNK, EPICENTRE); an RNA molecule that has a 5' triphosphate or diphosphate group wherein the beta or gamma phosphate of the group is labeled; including wherein the RPP is selected from among an aluminum-inducible RPP, E. coli RPP I, and Shigella RPP I; and, if included in the kit, the at least one other component is selected from the group consisting of: the RMP is RNA 5' monophosphatase 1 (RMP1); the AP is selected from among APEX™ alkaline phosphatase, shrimp alkaline phosphatase, and arctic alkaline phosphatase; the nucleic acid pyrophosphatase is tobacco acid pyrophosphatase (TAP); the decapping enzyme is selected from among yeast decapping enzyme, mammalian decapping enzyme, Arabidopsis thaliana decapping enzyme, poxvirus decapping enzyme, and vaccinia virus decapping enzyme (e.g., vaccinia virus decapping enzymes D9 and D10); the capping enzyme is selected from among poxvirus capping enzyme, Saccharomyces cerevisiae capping enzyme, and SCRIPTCAP™ capping enzyme; the RNA ligase is selected from among T4 RNA ligase and bacteriophage TS2126 RNA ligase; the poly (A) polymerase is selected from among E. coli poly(A) polymerase and Saccharomyces cerevisiae poly(A) polymerase; the RT is selected from among SUPERSCRIPT™ RT, AMV RT, and MMLV RT; the RNase H is selected from among E. coli RNase H and HYBRIDASE™ RNase H; the RNAP is selected from among a T7-type RNAP, T7 RNAP, T3 RNAP, and SP6 RNAP; the 5' exoribonuclease is selected from among TERMINATOR™ 5'-phosphate-dependent exonuclease and Saccharomyces cerevisae Xrn I exoribonuclease (Xrn I); or the PNK is T4 PNK.

In other embodiments, the present invention provides methods for adding a poly(A) tail to the 3'-ends of 2'OMe-RNA molecules in a sample, wherein the 2'-OMe group is on their 3'-terminal nucleotides, wherein the method comprises:

(a) incubating the sample with an adenylated mononucleotide (A5' pp 5'X) (e.g., adenylated adenosine-5'-monophosphate or diadenosine pyrophosphate (A5' pp 5'A)) and T4 RNA ligase (e.g., T4 RNA ligase 1 or T4 RNA ligase 2 or truncated T4 RNA ligase 2) under conditions and for sufficient time wherein at least one mononucleotide-5'-phosphate residue (5'-XMP) (e.g., 5'-AMP) is ligated to the 3'-ends of the 2'OMe-RNA molecules; and then (b) contacting the sample from step (a) with poly(A) polymerase and ATP under conditions and for sufficient time wherein a poly(A) tail is added to the 3' ends of the 2'OMe RNA molecules that have that have at least one mononucleotide-5'-phosphate residue (5'-XMP) (e.g., 5'-AMP) ligated their 3'-ends.

In some embodiments, the present invention provides methods for adding a homopolynucleotide tail (i.e., a poly(X) tail) (e.g. a poly(A) tail) to the 3'-ends of RNA molecules of interest in a sample (including to RNA molecules of interest that have a 2'OMe group on their 3'-terminal nucleotides or to RNA molecules of interest that lack a 2'OMe group on their 3'-terminal nucleotides), wherein the method comprises: incubating the sample with a molar excess of an adenylated 5'-mononucleotide (A5' pp 5'X) (e.g., adenylated adenosine-5'-monophosphate or diadenosine pyrophosphate (A5' pp 5'A)) and T4 RNA ligase (e.g., T4 RNA ligase 1 or T4 RNA ligase 2 or truncated T4 RNA ligase 2) under conditions and for sufficient time wherein a homopolymeric tail (poly(X) tail) (e.g., a poly(A) tail) is added to the 3'-ends of the RNA molecules of interest as a result of multiple successive ligation transfers of the 5'-mononucleotide (5'-XMP) residue from the adenylated 5'-mononucleotide ligation donor (A5' pp 5'X) (e.g., A5' pp 5'A)).

DESCRIPTION OF THE FIGURES

FIG. 2 shows activities of enzymes on RNA substrates that have different 5' end groups.

FIG. 3 shows reaction with RNA substrates by the enzymes indicated in FIG. 2.

FIG. 4 shows the DNA and amino acid sequences of *E. coli* RNA 5' polyphosphatase.

DESCRIPTION OF THE INVENTION

The invention relates to novel methods, compositions, and kits for selectively tagging the 5'-ends of one or more desired classes or types of RNA molecules for use in research, human or non-human diagnostic, or therapeutic applications. Each RNA class consists of RNA molecules that have a particular chemical moiety or group on the 5'-position of their 5'-nucleotides. The selectivity of the method, referred to as "5' ligation tagging," is conferred by one or more specific enzymes that, alone or in combination, selectively convert only the desired class or classes of RNA molecules to RNA molecules that have a 5' monophosphate, which RNA molecules can then serve as donors for ligation to an acceptor oligonucleotide (e.g., an RNA acceptor oligonucleotide) using RNA ligase, and one or more other specific enzymes that, alone or in combination, selectively convert only the undesired class or classes of RNA molecules to RNA molecules that have a 5' hydroxyl, which RNA molecules cannot serve as donors for ligation to an acceptor oligonucleotide. For example, novel methods are disclosed for using RNA 5' polyphosphatase (RPP), a novel new class of enzymes discovered by the applicants, to selectively convert RNA that has a 5' triphosphate, but not 5'-capped RNA, to RNA that has a 5' monophosphate, and then using an RNA acceptor oligonucleotide for 5' ligation tagging of the RNA that has a 5' monophosphate. Also, methods discovered by the applicants are disclosed for using RNA 5' monophosphatase (RMP) to selectively convert RNA that has a 5' monophosphate, but not RNA that has a 5' triphosphate, to RNA that has a 5' hydroxyl, which cannot serve as a donor for ligation. In some embodiments, the 5'-ligation-tagged RNA is used as a template for synthesis of tagged first-strand cDNA or double-stranded cDNA (e.g., for use as tagged templates for DNA sequencing, including using Roche 454, Illumina Solexa, or other massively parallel or "next-generation" sequencing platforms, or for making full-length cDNA for cloning, amplification or other applications). In some embodiments, the double-stranded cDNA contains an RNA polymerase promoter and the method further comprises synthesizing amplified sense or antisense RNA (e.g., for use in RT-qPCR, as target for microarray expression analysis, promoter identification, RNA processing analysis, and 5' or 3' RACE).

Figure 1:
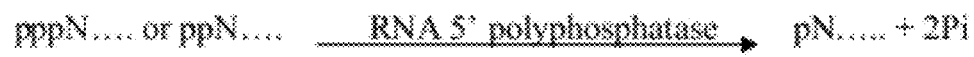
FIG. 1 shows examples of reactions catalyzed by RNA 5' polyphosphatase.
Figure 1:
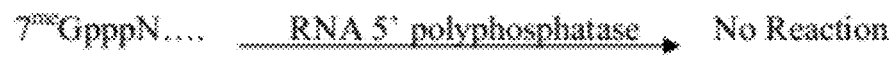

In some embodiments, the present invention provides methods employing a class of enzymes discovered by the applicants: RNA 5' polyphosphatases. For example, in some embodiments, the present invention provides methods employing a novel bacterial RNA 5' polyphosphatase enzyme (RPP) that the applicants designated "RNA 5' polyphosphatase I" ("RPP I"). Unlike tobacco acid pyrophosphatase (TAP), RNA 5' polyphosphatase does not digest the triphosphate bridge of capped RNA (e.g., $m^7G$-capped RNA), but it does convert 5'-triphosphorylated RNA or 5'-diphosphorylated RNA to RNA that has a 5' monophosphate group (FIG. 1). Following treatment of uncapped primary RNA or 5'-diphosphorylated RNA with RNA 5' polyphosphatase, the beta-gamma-dephosphorylated RNA can be tagged with an acceptor oligonucleotide (e.g., an RNA acceptor oligonucleotide) using RNA ligase.

Further disclosed herein is the novel use of RNA 5' monophosphatase (RMP) for converting RNA that has a 5' monophosphate group to RNA that has a 5' hydroxyl group. RMP converts RNA that has a 5' monophosphate (e.g., most eukaryotic "micro RNA" or "miRNA") to RNA that has a 5' hydroxyl, so that it cannot serve as a donor for ligation, and therefore, will not be 5' ligation tagged. In addition to miRNAs, most ribosomal RNAs (rRNAs), such as 18S and 26S or 28S eukaryotic rRNAs or 16S and 23S prokaryotic rRNAs, also have a 5'-monophosphate group. The applicants found that RMP1 removed the 5'-monophosphate group from these rRNA molecules and can be used for this purpose. However, the applicants found certain other methods are more efficient than RMP treatment for removing the large amounts of rRNA in most samples (e.g., rRNA comprises about 95 to 98% of the total RNA in most cells). Thus, in some preferred embodiments, rRNA is removed from the sample that is provided for use in the method of the present invention (e.g., using RIBOMINUS™ Kits from Invitrogen Life Technologies). Removal of the rRNA using alternative methods so that the sample that is provided for use in 5' ligation tagging is substantially free of rRNA enables the user to more effectively 5'-ligation tag other less-abundant RNA molecules in the sample that have a 5'-monophosphate group (e.g., miRNA) using the present methods. Therefore, unless otherwise specifically stated herein, it will be understood that, in some preferred embodiments, 5'-monophosphorylated rRNA molecules have been substantially removed from the samples provided in step (A) of a method of the present invention.

RPP and RMP can be used in combination with other enzymes already known in the art (e.g., FIG. 2) in order to convert virtually any desired population of RNA molecules having a particular group on its 5' end to RNA that has a 5' monophosphate group, which is then capable of being 5' ligation tagged with an RNA acceptor oligonucleotide using RNA ligase. Alternatively, RPP and RMP, alone or in combination with other enzymes known in the art, can be used to convert virtually any desired population of RNA molecules having a particular group on its 5' end to RNA that has a 5' hydroxyl group, which is then incapable of being 5' ligation tagged with an RNA acceptor oligonucleotide using RNA ligase. Thus, RPP and RMP, used alone or in combination with other enzymes known in the art, provide novel methods for highly selective 5' ligation tagging of a desired population of RNA molecules based on the nature of the 5' end group or groups (e.g., FIG. 3). Various embodiments of these methods are presented below. However, based on the description herein, those with knowledge in the art will know and understand other methods for 5' ligation tagging of specific populations of RNA using RPP or RMP in combination with other enzymes known in the art that modify the 5' ends of RNA, all of which methods are within the scope of the present invention.

Method 1 of the present invention is a method for 5' ligation tagging of uncapped RNA that has a 5' polyphosphate group, the method comprising the steps of: (A) providing: (i) a sample that contains uncapped RNA that has a 5' polyphosphate group (e.g., RNA that has a 5' triphosphate or RNA that has a 5' diphosphate group); (ii) RNA 5' polyphosphatase (e.g., *Escherichia coli* RPP I or *Shigella* RPP I); (iii) an acceptor oligonucleotide (e.g., an RNA acceptor oligonucleotide); and (iv) RNA ligase (e.g., T4 RNA ligase, EPICENTRE, or bacteriophage TS2126 RNA ligase); (B) contacting the sample with the RNA 5' polyphosphatase under conditions and for sufficient time wherein the uncapped RNA that has a 5' polyphosphate group is converted to RNA that has a 5' monophosphate group; and (C) contacting the sample from step (B) with the acceptor oligonucleotide and the RNA ligase under conditions and for sufficient time wherein the 3' end of the acceptor oligonucleotide is ligated to the 5' end of the RNA that has a 5' monophosphate group and 5'-ligation-tagged RNA is generated.

In some embodiments of method 1, the sample provided in step (A) additionally contains undesired RNA that has a 5' monophosphate group (e.g., miRNA) and, prior to converting the RNA that has a 5' polyphosphate group to RNA that has a 5' monophosphate group in step (B) or ligating the acceptor oligonucleotide to the RNA in step (C), the method additionally comprises: providing an RNA 5' monophosphatase (e.g., RNA 5' monophosphatase 1 or RMP1, EPICENTRE Technologies, Madison, Wis.); and contacting the sample that contains the undesired RNA with the RNA 5' monophosphatase in order to dephosphorylate the undesired RNA that has a 5' monophosphate group to generate RNA that has a 5' hydroxyl group so that it will not be ligated to the acceptor oligonucleotide (i.e., it is not 5' ligation tagged).

Thus, method 2 of the invention is the same as method 1, except that: in step (A), the sample additionally contains RNA that has a 5' monophosphate group, and step (A) additionally comprises providing an RNA 5' monophosphatase (e.g., RMP1); and step (B) additionally comprises, prior to contacting the sample with the RNA 5' polyphosphatase, the substeps of contacting the sample with the RNA 5' monophosphatase under conditions and for sufficient time wherein RNA in the sample that has a 5' monophosphate group is converted to RNA that has a 5' hydroxyl group, and inactivating or removing the RNA 5' monophosphatase.

In some embodiments of method 1 or method 2, the sample provided in step (A) additionally contains undesired RNA consisting of capped RNA or RNA that has a 5' hydroxyl group (which undesired RNA is not converted to RNA that has a 5'monophosphate group in step (B), and is not joined to the oligonucleotide acceptor to obtain 5'-ligation-tagged RNA in step (C)).

In some embodiments of method 1 or method 2, referred to as method 3, the method additionally comprises 5' ligation tagging of capped RNA in the sample, wherein the method additionally comprises the substeps of: providing a nucleic acid pyrophosphatase or decapping enzyme; and, prior to step (C), contacting the sample from step (B) with the nucleic acid pyrophosphatase or the decapping enzyme under conditions and for sufficient time wherein capped RNA in the sample is converted to RNA that has a 5' monophosphate group, whereby the capped RNA contained in the sample provided in step (A) is also 5'-ligation tagged in step (C).

In method 4 of the invention, the sample contains desired capped RNA and, optionally, undesired RNA that comprises uncapped RNA that has a 5' polyphosphate group (e.g., eukaryotic and/or prokaryotic RNA that has a 5' triphosphate or 5' diphosphate group, or uncapped pri-miRNA or uncapped pre-miRNA) and/or RNA that has a 5' monophosphate group (e.g., miRNA), and the method uses RNA 5' polyphosphatase to convert the uncapped RNA that has a 5' polyphosphate group to RNA that has a 5' monophosphate group, and then uses RNA 5' monophosphatase to dephosphorylate both the RNA that has a 5' monophosphate group that was obtained by contacting the uncapped RNA that has a 5' polyphosphate group with the RNA 5' polyphosphatase and the RNA in the sample that had a 5' monophosphate group prior to treatment with the RNA 5' polyphosphatase. Thus, both uncapped primary RNA and 5'-monophosphorylated RNA in the sample are converted to RNAs that have a 5' hydroxyl group, which are, therefore, not substrates for 5' ligation tagging. Then, following inactivation or removal of the RNA 5' monophosphatase, the sample is contacted with nucleic acid pyrophosphatase (e.g., tobacco acid pyrophosphatase) or a decapping enzyme (e.g., yeast decapping enzyme, mammalian decapping enzyme, *Arabidopsis thaliana* decapping enzyme, or D9 and D10 vaccinia virus decapping enzymes) to convert capped RNA to RNA that has a 5' monophosphate group for 5' ligation tagging. In different embodiments, the capped RNA in the sample is either naturally occurring (e.g., eukaryotic mRNA) or generated by in vitro capping (e.g., of prokaryotic mRNA) using a capping enzyme. Thus, in some embodiments, the 5'-ligation tagging method is useful for mapping transcriptional start sites (e.g., in eubacterial systems). The current CAGE methods known in the art do not enable mapping transcription start sites of prokaryotic (e.g., eubacterial) transcripts. One benefit of method 4 of the present invention compared to the oligo capping methods in the art is that, if desired, each type of RNA in the sample (based on the nature of its 5' end) can be 5' ligation tagged by taking aliquots from the sample for 5' ligation tagging after each step that generates RNA that has a 5' monophosphate group. This method enables 5' ligation tagging of capped RNA without also 5' ligation tagging uncapped RNA that has a 5' polyphosphate group or RNA in the sample that has a 5' monophosphate group.

Thus, method 4 is a method for 5' ligation tagging of capped RNA in a sample, comprising the steps of: (A) providing (i) a sample that contains capped RNA (e.g., m$^7$G-capped RNA), and, optionally, uncapped RNA that has a 5' polyphosphate group (e.g., RNA that has a 5' triphosphate and/or RNA that has a 5' diphosphate group), and RNA that has a 5' monophosphate group (e.g., miRNA); (ii) RNA 5' polyphosphatase (e.g., *E. coli* RPP I or *Shigella* RPP I); (iii)

RNA 5' monophosphatase (e.g., RMP1); (iv) nucleic acid pyrophosphatase (e.g., TAP) or a decapping enzyme (e.g., yeast decapping enzyme, mammalian decapping enzyme, *Arabidopsis thaliana* decapping enzyme, or D9 and D10 vaccinia virus decapping enzymes); (v) an acceptor oligonucleotide (e.g., an RNA acceptor oligonucleotide); and (vi) RNA ligase (e.g., T4 RNA ligase, EPICENTRE, or bacteriophage TS2126 RNA ligase); (B) contacting the sample with the RNA 5' polyphosphatase under conditions and for sufficient time wherein the uncapped RNA that has a 5' polyphosphate group is converted to RNA that has a 5' monophosphate group; (C) contacting the sample with the RNA 5' monophosphatase under conditions and for sufficient time wherein RNA that has a 5' monophosphate group is converted to RNA that has a 5' hydroxyl group; (D) inactivating or removing the RNA 5' monophosphatase; (E) contacting the sample with the nucleic acid pyrophosphatase or the decapping enzyme under conditions and for sufficient time wherein capped RNA in the sample is converted to RNA that has a 5' monophosphate group; (F) contacting the sample from step (E) with the acceptor oligonucleotide and the RNA ligase under conditions and for sufficient time wherein the 3' end of the acceptor oligonucleotide is ligated to the 5' end of the RNA that has a 5' monophosphate group that was generated in step (E) but is not ligated to the RNA that has a 5' monophosphate group which was converted from the uncapped RNA that has a 5' polyphosphate group in step (B) or to the RNA that has a 5' monophosphate group already in the sample provided in step (A), and 5'-ligation-tagged RNA is generated from the capped RNA.

In some embodiments of method 4, the sample additionally contains RNA that has a 5' hydroxyl group, which is not 5' ligation tagged in step (F).

Method 5 of the invention is a method for 5' ligation tagging of capped RNA and uncapped primary RNA that has a 5' polyphosphate group, comprising the steps of: (A) providing (i) a sample that contains capped RNA (e.g., m$^7$G-capped RNA) and/or uncapped RNA that has a 5' polyphosphate group (e.g., RNA that has a 5' triphosphate or a 5' diphosphate group); (ii) nucleic acid pyrophosphatase (e.g., TAP); (iii) an acceptor oligonucleotide (e.g., an RNA acceptor oligonucleotide); and (iv) RNA ligase (e.g., T4 RNA ligase, EPICENTRE, or bacteriophage TS2126 RNA ligase); (B) contacting the sample, wherein the sample has not been contacted with an alkaline phosphatase, with the nucleic acid pyrophosphatase under conditions and for sufficient time wherein the capped RNA and the uncapped RNA that has a 5' polyphosphate group are converted to RNA that has a 5' monophosphate group; (C) contacting the sample from step (B) with the acceptor oligonucleotide and the RNA ligase under conditions and for sufficient time wherein the 3' end of the acceptor oligonucleotide is ligated to the 5' end of the RNA that has a 5' monophosphate group and 5'-ligation-tagged RNA is generated.

In some embodiments of method 5, the sample additionally contains RNA that has a 5' monophosphate group, which is also 5' ligation tagged in step (C), or RNA that has a 5' hydroxyl group, which is not 5' ligation tagged in step (C).

Method 5 differs from the oligo capping methods in the prior art because those methods use an AP, which converts the 5' ends of RNA that has a 5' triphosphate to RNA that has a 5' hydroxyl, which cannot be used as substrates for 5' ligation tagging (or oligo capping) by RNA ligase. The benefit of the present method 5 is that it generates 5'-ligation-tagged RNA from RNA that has a 5' triphosphate and from RNA that has a 5' monophosphate, which permits analysis of the identity (e.g., sequence), quantity or relative abundance of 5'-triphosphorylated and 5'-monophosphorylated RNA molecules (e.g., compared to other RNA molecules within a sample and/or in one or more other samples), annotation, and biological function. Uncapped RNA that has a 5' triphosphate or a 5' monophosphate may have important biological functions. On the other hand, one potential disadvantage of the present method compared to methods in the art is that, since there is no step of treating the RNA in the sample with AP, RNA molecules in the sample that have a 5' monophosphate group will also be 5' ligation tagged, which 5'-ligation-tagged RNA molecules may not be of interest for a particular purpose.

Method 6 of the invention is a method for 5' ligation tagging of both capped RNA and uncapped RNA that has a 5' polyphosphate group in a sample without also 5' ligation tagging RNA in the sample that has a 5' monophosphate group, the method comprising the steps of: (A) providing (i) a sample that contains capped RNA (e.g., m$^7$G-capped RNA), uncapped RNA that has a 5' polyphosphate group (e.g., eukaryotic and/or prokaryotic RNA that has a 5' triphosphate or a 5' diphosphate group), and RNA that has a 5' monophosphate group (e.g., miRNA); (ii) RNA 5' monophosphatase (e.g., RMP1); (iii) a nucleic acid pyrophosphatase (e.g., TAP); (iv) an acceptor oligonucleotide (e.g., an RNA acceptor oligonucleotide); and (v) RNA ligase (e.g., T4 RNA ligase, EPICENTRE, or bacteriophage TS2126 RNA ligase); (B) contacting the sample with the RNA 5' monophosphatase under conditions and for sufficient time wherein RNA in the sample that has a 5' monophosphate group is converted to RNA that has a 5' hydroxyl group; (C) inactivating or removing the RNA 5' monophosphatase; (D) contacting the sample from step (C) with the nucleic acid pyrophosphatase under conditions and for sufficient time wherein the capped RNA and the uncapped RNA that has a 5' polyphosphate group are converted to RNA that has a 5' monophosphate group; (E) contacting the sample from step (D) with the acceptor oligonucleotide and the RNA ligase under conditions and for sufficient time wherein the 3' end of the acceptor oligonucleotide is ligated to the 5' end of the RNA that has a 5' monophosphate group that was generated in step D) and 5'-ligation-tagged RNA is generated.

In some embodiments of method 6, the sample additionally contains RNA that has a 5' hydroxyl group, which is not 5' ligation tagged in step (E).

Method 6 differs from the oligo capping methods in the prior art because those methods use an AP, which converts RNA that has a 5' triphosphate group to RNA that has a 5' hydroxyl group, which cannot be used as substrates for oligo capping by RNA ligase. One benefit of the present method is that it generates 5'-ligation-tagged RNA from RNA that has a 5' triphosphate group, which may have important biological functions. Thus, 5' ligation tagging of uncapped RNA that has a 5' triphosphate group permits analysis of its identity (e.g., sequence), quantity or relative abundance compared to other RNA molecules (e.g., within a sample a compared to the abundance in another sample), annotation, and biological function. One other benefit of the present method is that use of the RNA 5' monophosphatase converts RNA in the sample that has a 5' monophosphate group to RNA that has a 5' hydroxyl group which, therefore, will not be 5' ligation tagged. Thus, this method can be used to remove 5'-monophosphorylated RNA that is not of interest for a particular purpose.

Method 7 of the invention is a method for 5' ligation tagging of uncapped RNA that has a 5' polyphosphate group in a sample without also 5' ligation tagging RNA in the sample that has a 5' monophosphate group, the method comprising the steps of: (A) providing (i) a sample that contains uncapped RNA that has a 5' polyphosphate group (e.g., RNA that has a 5' triphosphate group (e.g., prokaryotic mRNA) or RNA that has a 5' diphosphate group) and RNA that has a 5' monophosphate group (e.g., miRNA); (ii) a capping enzyme (e.g., SCRIPTCAP™ capping enzyme system, EPICENTRE); (iii) an RNA 5' monophosphatase (e.g., RMP1, EPICENTRE) or alkaline phosphatase (e.g., APEX™ alkaline phosphatase, EPICENTRE; shrimp alkaline phosphatase, USB, Cleveland, Ohio; or Arctic alkaline phosphatase, New England Biolabs, MA); (iv) nucleic acid pyrophosphatase (e.g., TAP, EPICENTRE) or a decapping enzyme (e.g., yeast decapping enzyme, mammalian decapping enzyme, Arabidopsis thaliana decapping enzyme, or D9 and D10 vaccinia virus decapping enzymes); (v) an acceptor oligonucleotide (e.g., an RNA acceptor oligonucleotide); and (vi) RNA ligase (e.g., T4 RNA ligase, EPICENTRE, or bacteriophage TS2126 RNA ligase); (B) contacting the sample with the capping enzyme under conditions and for sufficient time wherein the uncapped RNA that has a 5' polyphosphate group is converted to capped RNA; (C) contacting the sample from step (B) with the RNA 5' monophosphatase or the alkaline phosphatase under conditions and for sufficient time wherein RNA that has a 5' monophosphate group is converted to RNA that has a 5' hydroxyl group; (D) inactivating or removing the RNA 5' monophosphatase or the alkaline phosphatase that was used in step (C); (E) contacting the sample following step (D) with the nucleic acid pyrophosphatase or the decapping enzyme under conditions and for sufficient time wherein capped RNA is converted to RNA that has a 5' monophosphate group; and (F) contacting the sample from step (E) with the acceptor oligonucleotide and the RNA ligase under conditions and for sufficient time wherein the 3' end of the acceptor oligonucleotide is ligated to the 5' end of the RNA that has a 5' monophosphate group and 5'-ligation-tagged RNA is generated.

In some embodiments of method 7, the sample additionally contains RNA that has a 5' hydroxyl group, which is not 5' ligation tagged in step (F).

Step (B) of method 7, which comprises treating the sample with a capping enzyme, generates capped RNA from the uncapped RNA that has a 5' polyphosphate group (e.g., RNA that has a 5' triphosphate group, such a prokaryotic primary RNA, or RNA that has a 5' diphosphate group). Then, in step (C), the RNA in the sample that has a 5' monophosphate group (e.g., miRNA) is converted to RNA that has a 5' hydroxyl group, which is not 5' ligation tagged by RNA ligase. Finally, the capped RNA is converted to RNA that has a 5' monophosphate group using a nucleic acid pyrophosphatase (e.g., TAP) or a decapping enzyme, and the RNA that has a 5' monophosphate group is then 5' ligation tagged using RNA ligase.

Method 8 of the invention comprises an embodiment of method 7 except that: the sample provided in step (A) additionally contains capped RNA (e.g., $m^7G$-capped RNA, e.g., eukaryotic mRNA), and, in step (F), the method generates 5'-ligation-tagged RNA from both the capped RNA provided in the sample in step (A) and the uncapped RNA in the sample that has a 5' polyphosphate group which is capped in step (B). In some embodiments of method 8, the sample additionally contains RNA that has a 5' hydroxyl group, which is not 5' ligation tagged in step (F).

In some embodiments of any of the methods wherein a nucleic acid pyrophosphatase (e.g., TAP) is provided in step (A) (e.g., some embodiments of methods 4 through 8), the method further comprises the step of: inactivating or removing the nucleic acid pyrophosphatase following the step of contacting the sample that contains capped RNA or uncapped RNA that has a 5' polyphosphate group with the nucleic acid pyrophosphatase under conditions and for sufficient time wherein capped RNA and uncapped RNA that has a 5' polyphosphate group in the sample is converted to RNA that has a 5' monophosphate group. If possible with respect to a particular embodiment, it is preferable to inactivate the nucleic acid pyrophosphatase by changing the conditions of the reaction mixture following the reaction to new conditions wherein the nucleic acid pyrophosphatase is inactive, but the enzyme used in the next step of the method is active. For example, tobacco acid pyrophosphatase (TAP) is active in a reaction mixture consisting of 50 mM sodium acetate (pH 6.0), 1 mM EDTA, 0.1%13-mercaptoethanol and 0.01% Triton X100. Following the reaction, the TAP can be inactivated by adjusting the pH to about 7.5 by the addition of sodium phosphate (pH 7.8) to the TAP reaction mixture to a final concentration of 20 mM. Of course, it is important to verify that the enzyme used in the next step of the method is active under these conditions.

Method 9 of the invention is a method for 5' ligation tagging capped RNA and RNA that has a 5' monophosphate group in a sample without also 5' ligation tagging uncapped RNA in the sample that has a 5' polyphosphate group, the method comprising the steps of: (A) providing (i) a sample that contains at least capped RNA, uncapped RNA that has a 5' polyphosphate group (e.g., RNA that has a 5' triphosphate group (e.g., prokaryotic mRNA) or RNA that has a 5' diphosphate group), and RNA that has a 5' monophosphate group (e.g., miRNA); (ii) a decapping enzyme (e.g., yeast decapping enzyme, mammalian decapping enzyme, Arabidopsis thaliana decapping enzyme, or D9 and D10 vaccinia virus decapping enzymes); (iii) an acceptor oligonucleotide (e.g., an RNA acceptor oligonucleotide); and (iv) RNA ligase (e.g., T4 RNA ligase, EPICENTRE, or bacteriophage TS2126 RNA ligase); (B) contacting the sample with the decapping enzyme under conditions and for sufficient time wherein capped RNA is converted to RNA that has a 5' monophosphate group; and (C) contacting the sample from step (B) with the acceptor oligonucleotide and the RNA ligase under conditions and for sufficient time wherein the 3' end of the acceptor oligonucleotide is ligated to the 5' end of the RNA that has a 5' monophosphate group and 5'-ligation-tagged RNA is generated.

In some embodiments of method 9, the sample additionally contains RNA that has a 5' hydroxyl group, which is not 5' ligation tagged in step (C).

Method 10 of the invention is a method for 5' ligation tagging of capped RNA in a sample without also 5' ligation tagging uncapped RNA that has a 5' polyphosphate group or RNA that has a 5' monophosphate group in the sample, the method comprising the steps of: (A) providing (i) a sample that contains at least capped RNA, uncapped RNA that has a 5' polyphosphate group (e.g., RNA that has a 5' triphosphate group (e.g., prokaryotic mRNA) or RNA that has a 5' diphosphate group), RNA that has a 5' monophosphate group (e.g., miRNA), and/or RNA that has a 5' hydroxyl group; (ii) an RNA 5' monophosphatase (e.g., RMP1, EPICENTRE) or alkaline phosphatase (e.g., APEX™ alkaline phosphatase, EPICENTRE; shrimp alkaline phosphatase, USB, Cleveland, Ohio; or Arctic alkaline phosphatase, New England Biolabs, MA); (iii) a decapping enzyme (e.g., yeast decapping enzyme, mammalian decapping enzyme, Arabidopsis thaliana decapping enzyme, or D9 and D10 vaccinia virus decapping enzymes); (iv) an acceptor oligonucleotide (e.g., an RNA acceptor oligonucleotide); and (v) RNA ligase (e.g., T4 RNA ligase, EPICENTRE, or bacteriophage TS2126 RNA ligase); (B) contacting the sample with the RNA 5' monophosphatase or the alkaline phosphatase under conditions and for sufficient time wherein the respective enzyme is active and the reactions it catalyzes can go to completion; (C)

inactivating or removing the RNA 5' monophosphatase or the alkaline phosphatase that was used in step (B); (D) contacting the sample with the decapping enzyme under conditions and for sufficient time wherein capped RNA is converted to RNA that has a 5' monophosphate group; and (E) contacting the sample from step (D) with the acceptor oligonucleotide and the RNA ligase under conditions and for sufficient time wherein the 3' end of the acceptor oligonucleotide is ligated to the 5' end of the RNA that has a 5' monophosphate group that was generated from the capped RNA in step (D) and 5'-ligation-tagged RNA is generated.

In some embodiments of method 10, the sample additionally contains RNA that has a 5' hydroxyl group, which is not 5' ligation tagged in step (E).

In some embodiments of any of the methods wherein a decapping enzyme (e.g., yeast decapping enzyme, mammalian decapping enzyme, *Arabidopsis thaliana* decapping enzyme, or D9 and D10 vaccinia virus decapping enzymes) is provided in step (A) (e.g., in some embodiments of methods 4 and 7 through 10), the method further comprises the step of: inactivating or removing the decapping enzyme following the step of contacting the sample that contains capped RNA with the decapping enzyme under conditions and for sufficient time wherein capped RNA in the sample is converted to RNA that has a 5' monophosphate group. If possible with respect to a particular embodiment, it is preferable to inactivate the decapping enzyme by changing the conditions of the reaction mixture following the reaction to new conditions wherein the decapping enzyme is inactive, but the enzyme used in the next step of the method is active. Of course, it is important to verify that the enzyme used in the next step of the method is active under these conditions.

The invention also comprises embodiments of any of methods 1 through 10 wherein, in step (A), a 5' exoribonuclease (XRN) is additionally provided (e.g., *Saccharomyces cerevisae* Xrn I exoribonuclease (Xrn I); TERMINATOR™ 5'-phosphate-dependent exonuclease, EPICENTRE), and, prior to step (B), the sample is contacted with the XRN under conditions and for sufficient time wherein RNA in the sample that has a 5' monophosphate group is digested.

The invention also comprises embodiments of any of methods 1 through 10 wherein a 5' exoribonuclease (XRN) is additionally provided in step (A) (e.g., *Saccharomyces cerevisae* Xrn I exoribonuclease (Xrn I); TERMINATOR™ 5'-phosphate-dependent exonuclease, EPICENTRE), and, following a step wherein an RNA that is present in the sample is converted to an RNA that has a 5' monophosphate group, the sample is contacted with the XRN under conditions and for sufficient time wherein the RNA that has a 5' monophosphate is digested. In some of these embodiments, the step of contacting the sample with the XRN replaces another step in the reaction, such as a step of contacting the sample with an RNA 5' monophosphatase (RMP) or alkaline phosphatase (AP).

In some preferred embodiments of any of methods 1 through 10, the sample provided in step (A) is treated to remove ribosomal RNA (e.g., 18S and 26S or 28S eukaryotic rRNA, or 16S and 23S prokaryotic rRNA) prior to its use in the method (e.g., using RIBOMINUS™ rRNA removal kits from INVITROGEN, or another suitable methods). Removal of the ribosomal RNA using a protocol such as that for a RIBOMINUS kit facilitates analysis of the RNA molecules of interest in the sample, including RNA molecules of interest that have a 5'-monophosphate group, using a method of the present invention.

Method 11 of the invention comprises embodiments of any of methods 1 through 10, including any embodiments thereof, wherein at least some of the RNA molecules of interest in a sample do not have a poly(A) tail, wherein the method additionally comprises adding a poly(A) tail to the 3'-end of the RNA molecules of interest.

In some embodiments, the method of adding the poly(A) tail comprises the steps of: providing a poly(A) polymerase (e.g., *Escherichia coli* poly(A) polymerase or *Saccharomyces* poly(A) polymerase) and ATP; and contacting the sample with the poly(A) polymerase and the ATP under conditions and for sufficient time wherein a poly(A) tail is added to the 3' ends of the RNA molecules in the sample and RNA that has a poly(A) tail is generated.

However, the applicants found that RNA molecules that have a 2'-O-methyl group (2'OMe) on the 3'-terminal nucleotide (e.g., plant miRNAs, germline-specific piwiRNAs, endogenous siRNAs), are either poorly adenylated or are not adenylated in vitro using either *E. coli* or *Saccharomyces* poly(A) polymerase. This is unfortunate because there is currently great interest in studying such 2'-O-methylated RNAs (also referred to as "2'OMe-RNAs") to profile their abundances, identify their functions, and use them for research, medical and agricultural applications. Polyadenylation of such 2'OMe-RNAs would enable addition of a priming site for synthesis of first-strand cDNAs and other downstream manipulations, including amplification (e.g., for RNA amplification) and/or for adding a sequencing tag domain to the first-strand cDNA or double-stranded cDNA (e.g., for preparing templates for next-generation or older sequencing methods, e.g., Sanger sequencing methods). The applicants observed that incubation of a molar excess of purified di-adenosine pyrophosphate (A5' pp 5'A, the adenylated form of adenosine-5'-monophosphate) with 2'OMe-RNA (e.g., a chemically synthesized 2'OMe-oligoribonucleotide (IDT, Coralville, Iowa); e.g., a 2'OMe-oligoribonucleotide identical to miR173[2'OMe], a 2'OMe-*Arabidopsis thaliana* miRNA) and RNA ligase (e.g., T4 RNA ligase 1 or T4 RNA ligase 2 (EPICENTRE, Madison, Wis.) resulted in approximately quantitative synthesis of a 2'OMe-oligoribonucleotide that had either one or two adenosine nucleotides ligated to the 3'-position of its 3'-end, and then a poly(A) tail (e.g., that was suitable for serving as a priming site for first-strand cDNA synthesis) was added to approximately 100% of these adenosine nucleotide-extended 2'OMe-oligoribonucleotide molecules using poly(A) polymerase in an in vitro reaction according to the instructions of the manufacturer (EPICENTRE, Madison, Wis., USA). Thus, in one specific embodiment of method 11 wherein at least some of the RNA in the sample that it is desired to be 5' ligation tagged has a 2'OMe group on its 3'-terminal nucleotide and wherein the step of adding the poly(A) tail comprises using a poly(A) polymerase, the method additionally comprises, prior to the step of contacting the sample with the poly(A) polymerase and the ATP, the step of: incubating the sample that contains the RNA that has a 2'OMe group on its 3'-terminal nucleotide with diadenosine pyrophosphate (A5' pp 5'A) and T4 RNA ligase (e.g., T4 RNA ligase 1 or T4 RNA ligase 2) in the absence of ATP or NAD under conditions and for sufficient time wherein at least one adenosine residue is added to the 3' ends of at least the RNA molecules that have a 2'OMe group on their 3'-terminal nucleotides.

Unexpectedly, the applicants further observed that incubating a sample that contained RNA of interest that had a 2'OMe group on its 3'-terminal nucleotide (or that contained RNA of interest that did not have a 2'OMe group on its 3'-terminal nucleotide) with diadenosine pyrophosphate (A5' pp 5'A) and T4 RNA ligase (e.g., T4 RNA ligase 1 or T4 RNA ligase 2) for longer reaction times resulted in addition of multiple adenosines to the 3'-end of the RNA that had a 2'OMe group on its 3'-terminal nucleotide. For example, in one experiment, approximately 15 to 20 adenosines were added to approximately all of the 51-mer 5'-triphosphorylated RNA molecules during a 4-hour reaction with a molar excess of diadenosine pyrophosphate (A5' pp 5'A) and T4 RNA ligase (e.g., T4 RNA ligase 1 or T4 RNA ligase 2). Thus, in some embodiments, method 11 of adding a poly(A) tail to the 3'-end of the RNA molecules of interest in the sample comprises only the step of incubating the sample that contains the RNA molecules of interest with a molar excess of diadenosine pyrophosphate (A5' pp 5'A) and T4 RNA ligase (e.g., T4 RNA ligase 1 or T4 RNA ligase 2) under conditions and for sufficient time wherein a poly(A) tail comprising or consisting of multiple adenosines is added to the 3'-end of the RNA molecules of interest.

The applicants believe that the methods comprising incubating the sample that contains the RNA molecules of interest (e.g., wherein the RNA molecules of interest comprise RNA molecules that have a 2'OMe group on their 3'-terminal nucleotides or wherein the RNA molecules of interest comprise any one or more RNA molecules, whether with or without a 2'OMe group) with a molar excess of diadenosine pyrophosphate (A5' pp 5'A) and T4 RNA ligase (e.g., T4 RNA ligase 1 or T4 RNA ligase 2, including truncated T4 RNA ligase 2) under conditions and for sufficient time that a poly(A) tail comprising or consisting of multiple adenosines is added to their 3'-ends are novel methods which have not previously been described in the art, and which are inventive even when they are not linked to the present methods for ligating an acceptor oligo nucleotide to the 5'-ends of the RNA molecules of interest for 5' ligation tagging.

Thus, one embodiment of the invention is a general method for adding a poly(A) tail to the 3'-ends of 2'OMe-RNA molecules in a sample, wherein the 2'-OMe group is on their 3'-terminal nucleotides, wherein the method comprises the steps of: (a) incubating the sample with an adenylated mononucleotide (A5' pp 5'X) (e.g., adenylated adenosine-5'-monophosphate or diadenosine pyrophosphate (A5' pp 5'A)) and T4 RNA ligase (e.g., T4 RNA ligase 1 or T4 RNA ligase 2 or truncated T4 RNA ligase 2) under conditions and for sufficient time wherein at least one mononucleotide-5'-phosphate residue (5'-XMP) (e.g., 5'-AMP) is ligated to the 3'-ends of the 2'OMe-RNA molecules; and then (b) contacting the sample from step (a) with poly(A) polymerase and ATP under conditions and for sufficient time wherein a poly(A) tail is added to the 3' ends of the 2'OMe-RNA molecules that have that have at least one mononucleotide-5'-phosphate residue (5'-XMP) (e.g., 5'-AMP) ligated their 3'-ends.

Thus, another embodiment of the invention is a general method for adding a homopolynucleotide tail (i.e., a poly(X) tail) (e.g. a poly(A) tail) to the 3'-ends of RNA molecules of interest in a sample (including to RNA molecules of interest that have a 2'OMe group on their 3'-terminal nucleotides or to RNA molecules of interest that lack a 2'OMe group on their 3'-terminal nucleotides), wherein the method comprises: incubating the sample with a molar excess of an adenylated 5'-mononucleotide (A5' pp 5'X) (e.g., adenylated adenosine-5'-monophosphate or diadenosine pyrophosphate (A5' pp 5'A)) and T4 RNA ligase (e.g., T4 RNA ligase 1 or T4 RNA ligase 2 or truncated T4 RNA ligase 2) under conditions and for sufficient time wherein a homopolymeric tail (poly(X) tail) (e.g., a poly(A) tail) is added to the 3'-ends of the RNA molecules of interest as a result of multiple successive ligation transfers of the 5'-mononucleotide (5'-XMP) residue from the adenylated 5'-mononucleotide ligation donor (A5' pp 5'X) (e.g., A5 ' pp 5'A)).

In some embodiments of method 11, the poly(A) tail is added to the 5'-ligation-tagged RNA generated in any of methods 1 through 10. In some other embodiments of method 11, the step of adding the poly(A) tail to the RNA in the sample is performed prior to generating the 5'-ligation-tagged RNA.

In some embodiments of method 11, the acceptor oligonucleotide for 5' ligation tagging is an RNA acceptor oligonucleotide that has a 5' cap nucleotide, and the method additionally comprises the steps of: transforming a eukaryotic cell with the 5'-ligation-tagged RNA that has a poly(A) tail, wherein the 5'-ligation-tagged RNA that has a poly(A) tail is expressed in the eukaryotic cell; in some of these embodiments, the 5'-ligation-tagged RNA that has a poly(A) tail is generated from RNA in the sample that encodes protein (e.g., from RNA comprising prokaryotic mRNA), and the protein is expressed in the eukaryotic cell.

In still other embodiments of method 11, an enzyme that adds a different homopolymeric tail to the 3' end of the RNA in the sample is used in any of methods 1 through 10. For example, an enzyme and reaction conditions that result in addition of a poly(U) or poly(C) or poly(I) tail to the 3' end of the RNA in the sample can be used, in which case a suitable primer that anneals to the homopolymeric tail can be used in embodiments discussed herein wherein a primer is provided and used in the method. Enzymes that have poly(U) polymerase activity have been described in the art (e.g., Kwak, Jae Eun and Wickens, M, RNA 13: 860-867, 2007). Any enzyme that is capable of adding a homopolymeric nucleotide tail to the 3' end of the RNA in the sample can be used for any of methods 1 through 10 of the present invention.

Method 11 can be beneficial because the addition of a poly(A) or another homopolymeric tail to the 3' ends of RNA in the sample provides a priming site for synthesis of first-strand cDNA from all of the RNA molecules in the sample, even if the RNA in the sample comprises a variety of different RNA molecules that exhibit different sequences. Also, since the poly(A) tail (or another homopolymeric tail) is added to the 3' end of the RNA in the sample or the 5'-ligation-tagged RNA generated in any of methods 1 through 10, the use of this tail as a priming site for a first-strand cDNA synthesis primer provides at least the potential for generating full-length first-strand cDNA, which would not be the case if an internal sequence with the RNA or the 5'-ligation-tagged RNA is used as a priming site.

In those embodiments of methods of the invention herein, wherein a poly(A) or other homopolymeric tail is added to the RNA in the sample or the 5'-ligation-tagged RNA, it will be understood herein that the term "5'-ligation-tagged RNA" refers to 5'-ligation-tagged RNA that has a poly(A) or other homopolymeric tail on its 3' end.

Still other embodiments of the invention provide methods and kits for obtaining only type-specific or condition-specific or environment-specific 5'-ligation-tagged RNA by subtraction of that portion of the 5'-ligation-tagged RNA in cells of one type or condition or environment that is the same as RNA in cells of another type or condition or environment.

Thus, in some embodiments, the method further comprises the steps of: annealing to the 5'-ligation-tagged RNA generated from a first sample that contained RNA from cells of one state or condition or environment an excess of cDNA prepared from a second sample that contained RNA from cells of a second state or condition or environment; and contacting the 5'-ligation-tagged RNA to which the cDNA is annealed with RNase H under conditions and for sufficient time wherein the 5'-ligation-tagged RNA that is annealed to the cDNA is digested and 5'-ligation-tagged RNA to which no cDNA is annealed is not digested, thereby subtracting the 5'-ligation-tagged RNA that is homologous to the cDNA. In some embodiments wherein the 5'-ligation-tagged RNA from the first sample was generated using an acceptor oligonucleotide to which an affinity molecule is attached or joined, the 5'-ligation-tagged RNA from the first sample that remains following the subtraction step is recovered following the subtraction step by contacting the sample containing the 5'-ligation-tagged RNA from the first sample with a solid surface to which an affinity binding substance that is capable of binding the affinity molecule is attached under conditions and for sufficient time wherein the affinity molecule binds to the affinity binding substance that is attached to the surface. In some embodiments, the affinity molecule is biotin and the affinity binding substance that is attached to the solid surface is avidin or streptavidin.

Thus, some embodiments of the invention provide methods for generating 5'-ligation-tagged RNA from RNA in one sample from which RNA that is in common with RNA in a second sample has been subtracted. For example, method 12 of the invention comprises embodiments of any of methods 1 through 11, wherein the sample comprises a first sample that contains RNA derived from cells of a first type or a first condition or from a first environment, and wherein the method results in subtraction from the 5'-ligation-tagged RNA generated from the first sample those RNA molecules that are also present in a second sample derived from cells of a second type or a second condition or from a second environment, thereby generating a population of 5'-ligation-tagged RNA molecules derived from RNA that is present only in the first sample but absent in the second sample, the method comprising the steps of: (i) providing the 5'-ligation-tagged RNA generated from the first sample, and a second sample that contains RNA derived from cells of a second type or a second condition or from a second environment; (ii) preparing first-strand cDNA by reverse transcription of the RNA in the second sample; (iii) annealing the 5'-ligation-tagged RNA generated from the first sample to the first-strand cDNA prepared from RNA from the second sample under conditions and for sufficient time wherein a hybridization complex is formed between the 5'-ligation-tagged RNA generated from the first sample and the first-strand cDNA prepared from RNA from the second sample; (iv) treating the hybridization complex with the RNase H under conditions and for sufficient time wherein the RNA to which the cDNA is annealed is digested, and subtracted 5'-ligation-tagged RNA consisting of 5'-ligation-tagged RNA derived from RNA that is present only in the first sample but absent in the second sample is generated; and (v) obtaining the subtracted 5'-ligation-tagged RNA.

In some embodiments of method 12, the method further comprises the step of: inactivating or removing the RNase H after step (iv). In preferred embodiments, the RNase H is inactivated by heating.

Method 13 is an embodiment of method 12, wherein the acceptor oligonucleotide that is provided in step (A) for generating 5'-ligation-tagged RNA from RNA in the first sample contains an affinity molecule, and the method further comprises the steps of: providing a solid surface to which an affinity-binding substance that is capable of binding the affinity molecule is attached; and, either prior to or after step (iv), contacting the 5'-ligation-tagged RNA generated from the first sample to the solid surface under conditions and for sufficient time wherein the 5'-ligation-tagged RNA from the first sample binds to the solid surface to which the affinity-binding substance is attached, and the 5'-ligation-tagged RNA derived from RNA in the first sample is captured on the solid surface.

Thus, methods 12 and 13 for generating and capturing subtracted 5'-ligation-tagged RNA each provide a way to obtain a sample that contains a population of RNA molecules that is specific for the type of cells in the sample (i.e., "type-specific") or for the condition(s) to which the cells in the sample were subjected (i.e., "condition-specific") or for the environment from which the cells in the sample were obtained (i.e., "environment-specific"). This population of RNA molecules (sometimes referred to "subtracted RNA" or "subtracted 5'-ligation-tagged RNA") is useful for further analysis or use. By way of example, the subtracted RNA can be identified (e.g. by analysis on an Affymetrix, Agilent, Illumina, or NimbleGen Systems microarray chip) or it can be used to prepare first-strand cDNA for use as templates for sequencing (e.g., using Sanger dideoxy or any of the "Nex-Gen" sequencing methods in the art (e.g., using the 454 sequencer from Roche, the Solexa sequencer from Illumina, the Solid sequencer from Applied Biosystems, or any other sequencers and systems in the art). In some embodiments, the 5'-ligation-tagged RNA has a tag on its 5' end that exhibits a sequence tag domain (e.g., for a Roche 454A sequence adaptor or its complement) and the first-strand cDNA is synthesized using a first-strand cDNA synthesis primer that exhibits a second sequence tag domain (e.g., for a Roche 454B sequence adaptor or its complement), thereby providing suitable 5'- and 3'-tagged first-strand cDNA molecules (e.g., for use as sequencing templates on the Roche 454 platform).

Still further, if the subtracted RNA is from a cell with a condition, such as a cancer cell, or a cell from another organic disease, or a cell that is infected with a bacterial, mycoplasmal, fungal, or viral pathogen, it comprises a population of potential pharmaceutical drug targets, which, if further validated, can be used to develop pharmaceuticals to relieve symptoms or potentially cure the disease. Of course, a validated condition-specific target can also be used to develop human or animal diagnostic tests, assays and kits. The subtracted RNA is also useful for research purposes. For example, in one embodiment, subtracted RNA from a cancer stem cell is compared with subtracted RNA from normal cells of the same type and/or other cancer cells which are not stem cells from the cancer lesion in order to understand the progression of the cancer and develop therapies and treatments. In still another embodiment, the subtracted RNA is used for synthesis of capped and polyadenylated RNA, which is further used for making an RNA-loaded antigen-presenting cell (APC) for use as a vaccine to prevent or treat a disease. For example, in some embodiments, subtracted RNA from the cancer stem cell from a tumor from a patient is used to make capped and polyadenylated RNA for use in transforming a dendritic cell prepared from the same patient, wherein the dendritic cell that is loaded with the tumor-specific RNA presents tumor-specific antigens. The tumor antigen-presenting dendritic cells are activated and used to make a vaccine to attempt to induce a cell-mediated immune response in the patient. In still another embodiment, the tumor antigen-presenting dendritic cells are used to make cytotoxic T-lymphocytes (CTLs) in culture, and the CTLs are administered to the patient (e.g., intravenously, subcutaneously, intramuscularly, intraperitoneally, or via another delivery route) as an immunotherapeutic vaccine to treat the patient. In still other embodiments, the subtracted RNA is used to make type-specific or condition-specific proteins or polypeptides by in vitro translation, which can be used as antigens to make an immunotherapeutic vaccine to prevent or treat a disease.

Still further, if the subtracted RNA is from a sample that contains cells from a particular environment, such as prokaryotic or eukaryotic microorganisms from an environmental sample, the method can be used to identify (e.g., sequence), quantify or determine the relative abundance of the nucleic acid molecules (e.g., by measuring the abundance of one or more nucleic acid molecules from or derived from one sample compared to the abundance of the nucleic acid molecules in another sample, e.g., using microarrays, digital next-generation sequencing, or other methods), annotate, and find the biological function of nucleic acid molecules expressed in the environmental sample, and to compare those aspects of one environmental sample with those aspects of other environmental samples, whether from the same location and environment at different times, or from different locations and environments. Thus, the methods can be used for various metatranscriptomics studies, including for identification of useful genes for research or for industrial or other commercial applications.

Method 14 of the invention comprises embodiments of any of methods 1 through 13 wherein the method further comprises synthesizing first-strand cDNA from the 5'-ligation-tagged RNA, wherein the method additionally comprises the steps of: providing an RNA-dependent DNA polymerase; and contacting the 5'-ligation-tagged RNA with the RNA-dependent DNA polymerase under conditions and for sufficient time wherein first-strand cDNA that is complementary to the 5'-ligation-tagged RNA is synthesized.

In some embodiments of method 14, a first-strand cDNA synthesis primer that is complementary to the RNA in the sample is not provided for synthesis of the first-strand cDNA using the RNA-dependent DNA polymerase. Without being bound by theory, the cDNA is presumably synthesized in these embodiments by intermolecular or intramolecular priming. In some embodiments, the cDNA that is synthesized is double-stranded. Without being bound by theory, the double-stranded cDNA is presumably synthesized by intermolecular priming (e.g., using RNA annealed to the cDNA for priming synthesis of the second strand of cDNA) or intramolecular priming (e.g., using a hairpin at the 3' end of the first strand of cDNA for priming synthesis of the second strand of cDNA).

In other embodiments of method 14, a first-strand cDNA synthesis primer is provided for priming synthesis of the first-strand cDNA using the 5'-ligation-tagged RNA as a template (which 5'-ligation-tagged RNA includes any poly(A) or other homopolymeric tail or oligonucleotide tag sequence on its 3' end). Thus, method 15 comprises method 14, wherein method 15 additionally comprises the steps of: providing a first-strand cDNA synthesis primer that is complementary to the 5'-ligation-tagged RNA; and contacting the 5'-ligation-tagged RNA with the first-strand cDNA synthesis primer and the RNA-dependent DNA polymerase under conditions and for sufficient time wherein cDNA that is complementary to the 5'-ligation-tagged RNA is synthesized.

Method 16 comprises embodiments of method 15 wherein the first-strand cDNA synthesis primer comprises a sequence wherein at least its 3' end exhibits a sequence selected from the group consisting of: a sequence that is complementary to a homopolymeric sequence that was added post-transcriptionally, either in vivo in the cell or in vitro, to the 3' end of the RNA in the sample or to the 3' end of the 5'-ligation-tagged RNA; a sequence that is complementary to a known sequence at the 3' end of one or more RNA molecules; a sequence that is complementary to one or more internal regions of one or more RNA molecules (e.g., that is complementary to one or more specific internal sequences); a collection of all possible sequences wherein each sequence is random (e.g., a random hexamer sequence or a random nonamer sequence, wherein at least one primer is present that is complementary to every sequence in the RNA); a sequence that is complementary to a poly(A) tail (e.g., a sequence selected from among an oligo (dT)n sequence, an oligo(dU)n sequence, an oligo(U)n sequence, an oligo(dT)nX anchored sequence, an oligo(dU) nX anchored sequence, and an oligo(U)nX anchored sequence of any length, but preferably wherein "n" is between about 6 and about 24 nucleotides, and "X" is a mixture of dG, dC and dA nucleotides); and a sequence that is complementary to an oligonucleotide tag that is added to the 3' end of the RNA in the sample or to the 3' end of the 5'-ligation-tagged RNA.

In some preferred embodiments of method 16, the first-strand cDNA synthesis primer is complementary to a poly(A) tail or other homopolymeric tail sequence or to an oligonucleotide tag sequence on the 3' end of the RNA of interest. These embodiments are preferred for some applications because a first-strand cDNA synthesis primer that anneals at the 3' end of the RNA molecules enables potential synthesis of full-length first-strand cDNA. Then, if the first-strand cDNA is used to make double-stranded cDNA, and the second-strand cDNA synthesis primer is complementary to the portion of the first-strand cDNA that is, in turn, complementary to the acceptor oligonucleotide that was ligated to the 5' end of the RNA of interest, the double-stranded cDNA will also be full-length and will encompass the sequences that correspond to the true 5' and 3' ends of the RNA molecules of interest. In some embodiments, the method for priming a poly(A) tail is preferred because a poly(A) tail can be added to all of the RNA molecules in a population even if the RNA comprises different sequences. In some embodiments, the poly(A) tail is naturally occurring in the sample (e.g., eukaryotic mRNA, including oligo(dT)-selected poly(A)-tailed eukaryotic mRNA). These embodiments are useful, for example, for making cDNA from one or more (including all) full-length RNA molecules (e.g., mRNA molecules) in the sample (e.g., for cloning; or for gene expression analysis using an array or microarray; or for sequencing; or for other analysis).

In some other embodiments of method 16, wherein the first-strand cDNA synthesis primer is a complementary to a known sequence within RNA in the sample (e.g., that is complementary to a known sequence at the 3' end of the coding region of the RNA), the method is useful for making cDNA from specific mRNAs for cloning or expression analysis of specific genes.

In other embodiments of method 16, wherein the first-strand cDNA synthesis primer exhibits a random sequence (e.g., a random hexamer or a random nonamer primer), the method is used for making cDNA from degraded RNA, such as degraded mRNA from a formalin-fixed paraffin-embedded tissue section, e.g., for cloning or expression analysis of genes in the tissue section. A first-strand cDNA synthesis primer that exhibits a random sequence can also be used in embodiments for making cDNA wherein the sequence of the RNA is unknown, or the RNA comprises multiple different RNA molecules that exhibit different sequences.

Method 17 of the invention comprises any of the embodiments of method 16 wherein the first-strand cDNA synthesis primer additionally exhibits a specific 5' sequence which is 5'-of the sequence exhibited at its 3' end, wherein said specific 5' sequence is capable of serving as a template for synthesis of second-strand cDNA that exhibits a specific 3' sequence that is complementary to the specific 5' sequence and that provides a site for specific priming of second-strand cDNA. In some embodiments, the specific 5' sequence comprises or consists of a tag that exhibits one or more tag domains, such as a sequencing tag domain that exhibits a Roche 454 sequencing adaptor, e.g., for massively parallel DNA sequencing using the Roche 454 sequencing platform.

Method 18 of the invention comprises embodiments of any of methods 14 through 17 wherein the method additionally comprises the steps of: providing RNase H (e.g., *Escherichia coli* RNase H or HYBRIDASE™ Thermostable RNase H, EPICENTRE, Madison, Wis.) and RNase I (e.g., *Escherichia coli* RNase I, EPICENTRE); and contacting the sample containing first-strand cDNA with the RNase H and the RNase I under conditions and for sufficient time wherein the RNA is digested.

Method 18 is used for removing the RNA template and the unhybridized RNA following synthesis of the first-strand cDNA. In some preferred embodiments of method 18, the method further comprises the step of inactivating or removing the RNase H and the RNase I. In some embodiments, the RNase H and the RNase I are inactivated by heating the reaction prior to proceeding to the next step (e.g., at 70° C. for about 15-30 minutes for *E. coli* RNase H and RNase I). In some embodiments of methods wherein the treatment with RNase H and RNase I is followed by one or more other steps wherein the presence of the RNase H and RNase I are not detrimental, the step of inactivating or removing the RNase H and the RNase I is omitted.

Method 19 of the invention comprises embodiments of any of methods 14 through 18 wherein the method additionally comprises the steps of: providing a DNA-dependent DNA polymerase; and contacting the first-strand cDNA with the DNA-dependent DNA polymerase under conditions and for sufficient time wherein double-stranded cDNA is synthesized.

Method 20 comprises embodiments of any of methods 14 through 19 wherein the method additionally comprises synthesis of double-stranded cDNA, wherein the method additionally comprises the steps of: providing a second-strand cDNA synthesis primer that is complementary to the portion of the first-strand cDNA that is complementary to the acceptor oligonucleotide provided in step (A), and a DNA-dependent DNA polymerase; and contacting the second-strand cDNA synthesis primer and the DNA-dependent DNA polymerase with the first-strand cDNA under conditions and for sufficient time wherein double-stranded cDNA is synthesized.

Method 21 comprises embodiments of methods 19 or 20 wherein the DNA-dependent DNA polymerase is the same as the RNA-dependent DNA polymerase provided for synthesis of first-strand cDNA.

Method 22 comprises embodiments of methods 19 or 20 wherein the DNA-dependent DNA polymerase is different from the RNA-dependent DNA polymerase provided for synthesis of first-strand cDNA.

Method 23 comprises embodiments of any of methods 19 through 22 wherein the 5' portion of the acceptor oligonucleotide (e.g., an RNA acceptor oligonucleotide), the 5'-portion of the first-strand cDNA synthesis primer, or the 5'-portion of the second-strand cDNA synthesis primer exhibits a sequence for one strand of a double-stranded RNA polymerase promoter (e.g., for a T7-type RNA polymerase, such as T7, T3, or SP6 RNA polymerase) and the method further comprises the steps of: providing an RNA polymerase that can synthesize RNA using the double-stranded RNA polymerase promoter for which a sequence for one strand is exhibited in the acceptor oligonucleotide, first-strand cDNA synthesis primer, or the second-strand cDNA synthesis primer; and contacting the double-stranded cDNA with the RNA polymerase under conditions and for sufficient time wherein RNA is synthesized.

Thus, in some embodiments of method 23, the acceptor oligonucleotide exhibits a sequence for one strand of an RNA polymerase promoter, whereas in other embodiments, the acceptor oligonucleotide does not exhibit a sequence for one strand of an RNA polymerase promoter.

In some embodiments of method 23, wherein the acceptor oligonucleotide does not exhibit a sequence for one strand of an RNA polymerase promoter, the sequence for one strand of an RNA polymerase promoter is exhibited by the 5' portion of the second-strand cDNA synthesis primer, wherein its 3' portion exhibits a sequence that is complementary to and anneals to the tag at the 3' end of the first-strand cDNA. The tag at the 3' end of the first-strand cDNA is, in turn complementary to the acceptor oligonucleotide which was ligated to RNA that has a 5' monophosphate group by the RNA ligase during the 5' ligation tagging step of the method. Thus, the tag at the 3' end of the first-strand cDNA is added during the step of contacting the 5'-ligation-tagged RNA with the RNA-dependent DNA polymerase. Then, during the step of synthesizing the double-stranded DNA, the RNA polymerase promoter is generated by DNA-dependent DNA polymerase extension of both the second-strand cDNA primer using the first-strand cDNA as a template, and extension of the first-strand cDNA using the 5' portion of the second-strand cDNA synthesis primer as a template. In some of these embodiments, RNA synthesized using the double-stranded cDNA is sense RNA with respect to the RNA contained in the sample provided in step (A) of the method.

In still other embodiments of method 23, wherein the acceptor oligonucleotide does not exhibit a sequence for one strand of an RNA polymerase promoter, the sequence for one strand of an RNA polymerase promoter is exhibited by the 5' portion of the first-strand cDNA synthesis primer, wherein its 3' portion exhibits a sequence that is complementary to the 5'-ligation-tagged RNA generated using the method. In some of these embodiments, RNA synthesized using the double-stranded cDNA is anti-sense RNA with respect to the RNA contained in the sample provided in step (A) of the method.

Method 24 comprises embodiments of any of methods 1 through 23, wherein the acceptor oligonucleotide, the first-strand cDNA primer, or the second-strand cDNA primer, respectively, contains or is joined to an affinity molecule (e.g., biotin or digoxigenin), and the method additionally comprises the steps of: providing a solid surface that is covalently or non-covalently coated with an affinity binding substance that is capable of specifically binding and forming a specific binding pair with the affinity molecule (e.g., streptavidin or avidin for binding biotin, or an antibody for binding digoxigenin); and, either prior to or following the step in which it is used, contacting the respective acceptor oligonucleotide, the first-strand cDNA primer, or the second-strand cDNA primer that is chemically joined to the affinity molecule under conditions and for sufficient time wherein it binds to affinity binding substance that is joined to the solid surface.

With respect to method 24, the invention is not limited to a particular solid surface, which can be porous or non-porous, and of any composition, size or shape that is suitable for the particular method and application. For example, the solid surface can be selected from the group consisting of: magnetic beads, coated beads, slides, the wells of a microtiter plate, tubes, and dipsticks consisting of glass, plastic (e.g., latex or polystyrene), silica, Teflon, or another suitable material. The purpose of the solid surface that is coated with the affinity binding substance is to permit manipulation (e.g., capture and washing to remove from other molecules in a reaction mixture), isolation, and capture of the acceptor oligonucleotide, the first-strand cDNA primer, or the second-strand cDNA primer that is chemically joined to the affinity molecule, or to permit manipulation, isolation, and capture of the respective 5'-ligation-tagged RNA, first-strand cDNA, second-stranded cDNA, or double-stranded cDNA obtained therefrom. In order to prevent non-specific binding, in some embodiments, the solid support is treated with a large excess of a substance selected from the group consisting of: DNA-free tRNA; protein (e.g. BSA), polysaccharide (e.g., glycogen, dextran sulphate, or heparin). The invention is also not limited to a specific affinity molecule or affinity binding substance, so long as they are capable of specifically binding and forming a specific binding pair.

Method 25 of the invention comprises preferred embodiments of method 24 wherein the respective 5'-ligation-tagged RNA, first-strand cDNA, or second-strand cDNA that is synthesized contains an affinity molecule and said 5'-ligation-tagged RNA, first-strand cDNA, or second-strand cDNA that contains the affinity molecule is captured, isolated or purified by binding it to the solid surface, the method comprising the steps of: contacting the 5'-ligation-tagged RNA, the first-strand cDNA, or the second-strand cDNA that contains the affinity molecule with the solid surface in the presence of reagents and under conditions that facilitate its binding to the affinity-binding substance that is attached to the solid surface, wherein the 5'-ligation-tagged RNA, the first-strand cDNA, or the second-strand cDNA that contains the affinity molecule is bound to the surface, thereby capturing, isolating, or purifying the 5'-ligation-tagged RNA, the first-strand cDNA, or the second-strand cDNA that contains the affinity molecule.

Method 26 comprises embodiments of methods 24 or 25 wherein the affinity molecule is biotin and the affinity binding substance is avidin or streptavidin, or wherein the affinity molecule is digoxigenin and the affinity binding substance is an antibody that specifically binds digoxigenin.

In some embodiments of any of methods 1 through 26, the uncapped RNA that has a 5' polyphosphate group comprises or consists of RNA that has a 5' triphosphate group selected from among: primary eukaryotic RNA; primary prokaryotic RNA (e.g., bacterial mRNA); ncRNA; and RNA that is synthesized in an in vitro transcription reaction using an RNA polymerase.

In some embodiments of any of methods 1 through 26, the uncapped RNA that has a 5' polyphosphate group comprises or consists of RNA that has a 5' diphosphate group that is the product of digestion of a primary RNA transcript with an RNA triphosphatase of a capping enzyme system (e.g., poxvirus capping enzyme, vaccinia capping enzyme, *Saccharomyces cerevisiae* capping enzyme, or SCRIPTCAP™ capping enzyme kit, EPICENTRE).

In general, the sample provided in step (A) of any of methods 1 through 26 can be from a eukaryote, a prokaryote, or from both one or more eukaryotes and/or one or more prokaryotes. In some embodiments, the RNA in the sample is amplified using an in vitro transcription or RNA amplification; however, in such embodiments, it is preferred that that RNA is 5' ligation tagged prior to the in vitro transcription or RNA amplification so that the group on the 5' end of the RNA in the sample that it is 5' ligation tagged is what is present in the biological source.

With respect to any of the methods of the present invention: If present in the sample, uncapped RNA that has a 5' polyphosphate group can consist of RNA that has a 5' triphosphate group or RNA that has a 5' diphosphate group. In some embodiments of any of the methods, if present in the sample, the uncapped RNA that has a 5' triphosphate group is selected from the group consisting of: prokaryotic primary RNA, eukaryotic primary RNA, and RNA synthesized by in vitro transcription of a DNA template using an RNA polymerase. In some embodiments, the RNA synthesized by in vitro transcription of a DNA template using an RNA polymerase is from an RNA amplification reaction, including an RNA amplification reaction that synthesizes sense or anti-sense RNA using one or more methods of the present invention. In some embodiments of any of the methods, if present in the sample, the uncapped RNA that has a 5' triphosphate group comprises eukaryotic mRNA, eukaryotic non-coding RNA, prokaryotic mRNA, and/or prokaryotic non-coding RNA. In some embodiments of any of the methods, the RNA that has a 5' diphosphate group, if present in the sample, can be the product of digestion of uncapped primary RNA by an RNA triphosphatase (e.g., a polypeptide that has RNA triphosphatase activity which comprises a capping enzyme system (e.g., a poxvirus capping enzyme, a vaccinia virus capping enzyme, or a *Saccharomyces cerevisiae* RNA triphosphatase), or it can be the product of digestion of 5' capped RNA with a decapping enzyme that comprises a Dcp2 subunit (e.g., eukaryotic mRNA decapping enzymes: Coller, J and Parker, R, Ann. Rev. Biochem. 73: 861-890, 2004; yeast decapping enzyme: Steiger, M et al., RNA 9: 231-238, 2003; mammalian decapping enzymes: Piccirillo, C et al., RNA 9: 1138-1147, 2003; *Arabidopsis thaliana* decapping enzymes: Gunawardana, D et al., Nucleic Acids Res. 36: 203-216, 2008, and Iwasaki S, et al., FEBS Lett. 581: 2455-2459, 2007); and vaccinia virus decapping enzymes vaccinia virus D9 or D10 decapping enzymes; Parrish, S and Moss, B, J. Virol. 81: 12973-12978, 2007; Parrish, S et al., Proc Natl Acad Sci USA 104: 2139-2144, 2007).

In general, if the RNA molecules of interest that it is desired to 5' ligation tag comprise RNA molecules in the sample that have a 5'-hydroxyl group, any of methods 1 through 26 additionally comprise the step of treating the sample with polynucleotide kinase (PNK) (e.g., T4 PNK) and ATP under conditions and for sufficient time wherein the RNA in the sample that has a 5'-hydroxyl group is converted to RNA that has a 5'-monophosphate group prior to the step comprising incubating the RNA with the acceptor oligonucleotide and the RNA ligase.

In general, an RNA acceptor oligonucleotide is the preferred acceptor oligonucleotide that is provided and used in all of the methods of the invention wherein an acceptor oligonucleotide is provided and used. Thus, in some preferred embodiments of any of methods 1 through 26, the acceptor oligonucleotide is an RNA acceptor oligonucleotide (also referred to as an "RNA acceptor oligo" or "RNA acceptor" or "acceptor RNA" or "RNA acceptor molecule" or "RNA oligo acceptor" or the like). However, in some embodiments, a DNA acceptor oligonucleotide is used. The acceptor oligonucleotide is not limited with respect to length, but, in general, the minimum size of an RNA acceptor oligonucleotide consists of a trinucleoside diphosphate. In some preferred embodiments the RNA acceptor oligonucleotide consists of between 3 ribonucleotides and about 25 ribonucleotides. An RNA acceptor oligonucleotide in this small size range is preferred over a larger one because it is possible to use a higher molar concentration of the RNA acceptor oligonucleotide for the RNA ligase step (e.g., to increase the efficiency of 5' ligation tagging of the RNA donor molecules), and because there is less likelihood that the shorter RNA acceptor oligonucleotide will anneal to itself or to one or more RNA sequences exhibited by the RNA donor molecules, either of which could decrease ligation efficiency or result in artifacts. Thus, in some preferred embodiments, it is preferred that the RNA acceptor oligonucleotide exhibits a sequence that is unlikely to anneal to itself (e.g., due to complementarity of intramolecular sequences) and that is unlikely to anneal to RNA donor molecules or other nucleic acids in the sample (e.g., due to complementarity of intermolecular sequences)

In some preferred embodiments, the 5' end of the RNA acceptor oligonucleotide has a 5' hydroxyl group so that it cannot serve as an RNA donor for ligation. In some preferred embodiments, the 5' end of the RNA acceptor oligonucleotide has a 5' cap nucleotide, which 5'-capped RNA acceptor oligonucleotide cannot serve as an RNA donor for ligation.

With respect to the nucleoside composition, in some preferred embodiments wherein T4 RNA ligase is used as the ligase, the 3' terminal nucleotide of the RNA acceptor oligonucleotide consists of adenosine. In some preferred embodiments, the 3' terminal nucleotide of the RNA acceptor oligonucleotide does not consist of uridine. In some preferred embodiments, the last two nucleotides at the 3' end of the RNA acceptor oligonucleotide consist of adenosine. In some preferred embodiments, the last three nucleotides at the 3' end of the RNA acceptor oligonucleotide consist of adenosine. In some preferred embodiments, the 3' terminal nucleotide of the RNA acceptor oligonucleotide does not consist of uridine. Additional information for designing and using an RNA acceptor oligonucleotide and information related to the properties and use of the donor RNA that is to be 5' ligation tagged using the methods of the present invention have been disclosed in the art (e.g., Gumport R I and Uhlenbeck O C, Gene Amplif Anal. 2: 313-345, 1981; Gumport R I and Uhlenbeck O C, Gene Amplif Anal. 2: 313-345, 1981; Romaniuk E, McLaughlin L W, Neilson T, and Romaniuk P J. Eur J. Biochem. 125: 639-43, 1982; Romaniuk P J and Uhlenbeck O C. Methods Enzymol.;100: 52-59, 1983; and Uhlenbeck O C and Gumport R I (1982) In: The Enzymes Vol. XV, pp. 31-58, (Boyer, P. D., ed.) Academic Press, New York). In general, the particular nucleotide composition of the 5'-phosphorylated end of the donor molecule does not have nearly as much effect on the efficiency of 5' ligation tagging as the nucleotide composition of the 3'-hydroxylated end of the RNA acceptor oligonucleotide.

In some other preferred embodiments, another RNA ligase than T4 RNA ligase is used as the ligase (e.g., bacteriophage TS2126 RNA ligase) and the 3' terminal nucleotide or nucleotides of the RNA acceptor oligonucleotide may consist of one or more nucleosides other than adenosine. If possible, the 3' nucleotides of the RNA acceptor oligonucleotide that are optimal for ligation to 5'-monophosphorylated donor RNA molecules by the particular RNA ligase are experimentally determined.

A variety of different enzymes are used in the methods of the invention. In some embodiments of any of the methods of the invention wherein an RNA 5' polyphosphatase (RPP) is used, the RPP is selected from among an aluminum-inducible RNA 5' polyphosphatase, an *E. coli* RPP, *E. coli* RPP I, a *Shigella* RPP, and *Shigella* RPP I. In some embodiments of any of the methods of the invention wherein an RNA 5' monophosphatase (RMP) is used, the RMP is RNA 5' monophosphatase 1 (RMP1, EPICENTRE). In some embodiments of any of the methods of the invention wherein an alkaline phosphatase is used, the alkaline phosphatase is selected from among APEX™ alkaline phosphatase (EPICENTRE), shrimp alkaline phosphatase (USB, Cleveland, Ohio), and Arctic alkaline phosphatase (New England Biolabs, MA). In some embodiments of any of the methods of the invention wherein a nucleic acid pyrophosphatase is used, the pyrophosphatase is tobacco acid pyrophosphatase (TAP) (EPICENTRE). In some embodiments of any of the methods of the invention wherein a decapping enzyme is used, the decapping enzyme is selected from among yeast decapping enzyme, mammalian decapping enzyme, *Arabidopsis thaliana* decapping enzyme, and vaccinia virus decapping enzymes D9 or D10. In some embodiments of any of the methods of the invention wherein a capping enzyme is used, the capping enzyme is selected from among a poxvirus capping enzyme, *Saccharomyces cerevisiae* capping enzyme, vaccinia virus capping enzyme, and SCRIPTCAP™ capping enzyme (EPICENTRE). In some embodiments of any of the methods of the invention wherein an RNA ligase is used, the RNA ligase is selected from among T4 RNA ligase, EPICENTRE, and bacteriophage TS2126 RNA ligase. In some embodiments of any of the methods of the invention wherein a poly(A) polymerase is used, the poly(A) polymerase is selected from among *E. coli* poly(A) polymerase, (EPICENTRE) and *Saccharomyces cerevisiae* poly(A) polymerase. In some embodiments of any of the methods of the invention wherein an RNA-dependent DNA polymerase is used, the RNA-dependent DNA polymerase is selected from among SUPERSCRIPT RT (Invitrogen, Carlsbad, Calif.), AMV RT, and MMLV RT (EPICENTRE). In some embodiments of any of the methods of the invention wherein an RNase H is used, the RNase H is selected from among *E. coli* RNase H (EPICENTRE), Tth RNase H, Tfl RNase H, and HYBRIDASE™ RNase H (EPICENTRE). In some embodiments of any of the methods of the invention wherein an RNA polymerase (RNAP) is used, the RNA polymerase is selected from among a T7-type RNAP, T7 RNAP, T3 RNAP, and SP6 RNAP (EPICENTRE). In some embodiments of any of the methods of the invention wherein an exoribonuclease (XRN) is used, the exoribonuclease is selected from among *Saccharomyces cerevisae* Xrn I exoribonuclease (Xrn I), and TERMINATOR™ 5'-phosphate-dependent exonuclease (EPICENTRE). In some embodiments of any of the methods of the invention wherein a polynucleotide kinase (PNK) is used, the polynucleotide kinase is T4 PNK (EPICENTRE).

Those with knowledge in the art will understand that the order of performing certain steps of the various methods of the invention is important, but that the order of the steps can be varied provided that the effects of each of the enzymes on the groups at the 5'-ends of the various classes of RNA molecules that may be present in the sample are carefully taken into account so as not to adversely affect the intended goal.

In some embodiments of any of the methods of the invention wherein a particular enzyme is provided and used, the method also further comprises the step of: inactivating or removing the particular enzyme following its use in the method. If possible with respect to a particular embodiment, it is preferable to inactivate the particular enzyme either by heating or by changing the conditions of the reaction mixture following the reaction to new conditions wherein the particular enzyme becomes inactive, but the enzyme used in the next step of the method is active. For example: RNA 5' monophosphatase 1 (RMP1) can be inactivated by heating the reaction mixture at 65° C. for about 15 minutes; *E. coli* RNA 5' polyphosphatase I (RPP I) can be inactivated in the RPP I reaction mixture by adding magnesium to a final concentration of about 1 to 10 mM and/or inorganic phosphate ions to a final concentration of about 0.1 mM; and tobacco acid pyrophosphatase (TAP) can be inactivated by adjusting the pH from pH 6.0 to about pH 7.5 by the addition of sodium phosphate (pH 7.8) to the TAP reaction mixture to a final concentration of about 10 mM. Of course, it is important to verify that the enzyme used in the next step of the method is active under the reaction conditions that result from the inactivation step for the particular enzyme.

One embodiment of the invention is a kit comprising RNA ligase (e.g., T4 RNA ligase or bacteriophage TS2126 RNA ligase (all from EPICENTRE); an RNA acceptor oligonucleotide; and an RNA 5' polyphosphatase (e.g., an aluminum-inducible RNA 5' polyphosphatase, e.g., *Escherichia coli* RNA 5' polyphosphatase I (*E. coli* RPP I or RPP I, EPICENTRE) or *Shigella* RNA 5' polyphosphatase I). In some embodiments, the kit additionally comprises RNA 5' monophosphatase (e.g., RNA 5' monophosphatase 1 (RMP1, EPICENTRE). In some embodiments of the kit that additionally comprises RNA 5' monophosphatase, the kit additionally comprises a nucleic acid pyrophosphatase (e.g., tobacco acid pyrophosphatase (TAP), EPICENTRE); or a decapping enzyme (e.g., yeast decapping enzyme, mammalian decapping enzyme, *Arabidopsis thaliana* decapping enzyme, or vaccinia virus decapping enzymes D9 or D10).

Another embodiment of the invention is a kit comprising RNA ligase (e.g., T4 RNA ligase, EPICENTRE, or bacteriophage TS2126 RNA ligase); an RNA acceptor oligonucleotide; an RNA 5' monophosphatase (e.g., RNA 5' monophosphatase 1 (RMP1, EPICENTRE); and a nucleic acid pyrophosphatase (e.g., tobacco acid pyrophosphatase (TAP), EPICENTRE).

Another embodiment of the invention is a kit comprising a nucleic acid pyrophosphatase (e.g., tobacco acid pyrophosphatase), an RNA acceptor oligonucleotide, and bacteriophage TS2126 RNA ligase.

Another embodiment of the invention is a kit comprising RNA ligase (e.g., T4 RNA ligase, EPICENTRE, or bacteriophage TS2126 RNA ligase); an RNA acceptor oligonucleotide; RNA 5' polyphosphatase (e.g., an aluminum-inducible RNA 5' polyphosphatase, e.g., *Escherichia coli* RNA 5' polyphosphatase I (*E. coli* RPP I or RPP I, EPICENTRE) or *Shigella* RNA 5' polyphosphatase I), and at least one other component selected from the group consisting of: RNA 5' monophosphatase (e.g., RNA 5' monophosphatase 1 (RMP1, EPICENTRE); and a nucleic acid pyrophosphatase (e.g., tobacco acid pyrophosphatase (TAP), EPICENTRE); and a decapping enzyme (e.g., yeast decapping enzyme, mammalian decapping enzyme, *Arabidopsis thaliana* decapping enzyme, or vaccinia virus decapping enzymes D9 or D10).

Another embodiment of the invention is a kit comprising RNA ligase (e.g., T4 RNA ligase, EPICENTRE, or bacteriophage TS2126 RNA ligase); an RNA acceptor oligonucleotide; a capping enzyme (e.g., poxvirus capping enzyme, *Saccharomyces cerevisiae* capping enzyme, or SCRIPTCAP™ capping enzyme kit, (EPICENTRE)); and at least one other component selected from the group consisting of: RNA 5' monophosphatase (e.g., RNA 5' monophosphatase 1 (RMP1), EPICENTRE) or an alkaline phosphatase (e.g., APEX™ Alkaline Phosphatase (EPICENTRE), shrimp alkaline phosphatase (USB, Cleveland, Ohio), or Arctic Alkaline Phosphatase (New England Biolabs, MA); and a nucleic acid pyrophosphatase (e.g., tobacco acid pyrophosphatase (TAP), EPICENTRE) or a decapping enzyme (e.g., yeast decapping enzyme, mammalian decapping enzyme, *Arabidopsis thaliana* decapping enzyme, or vaccinia virus decapping enzymes D9 or D10).

Another embodiment of the invention is a kit comprising RNA ligase (e.g., T4 RNA ligase, EPICENTRE, or bacteriophage TS2126 RNA ligase); an RNA acceptor oligonucleotide; a decapping enzyme (e.g., yeast decapping enzyme, mammalian decapping enzyme, *Arabidopsis thaliana* decapping enzyme, or vaccinia virus decapping enzymes D9 or D10); and at least one other component selected from the group consisting of: RNA 5' monophosphatase (e.g., RNA 5' monophosphatase 1 (RMP1), EPICENTRE); and an alkaline phosphatase (e.g., APEX™ Alkaline Phosphatase (EPICENTRE), shrimp alkaline phosphatase (USB, Cleveland, Ohio), or Arctic Alkaline Phosphatase (New England Biolabs, MA).

Another embodiment of the invention is a kit comprising RNA ligase (e.g., T4 RNA ligase, EPICENTRE, or bacteriophage TS2126 RNA ligase); an RNA acceptor oligonucleotide; and a decapping enzyme (e.g., yeast decapping enzyme, mammalian decapping enzyme, *Arabidopsis thaliana* decapping enzyme, or vaccinia virus decapping enzymes D9 or D10).

In some embodiments of any of the above kits, the kit additionally comprises at least one other component selected from the group consisting of: polynucleotide kinase (PNK) (e.g., T4 PNK, EPICENTRE), a first-strand cDNA synthesis primer; a second-strand cDNA synthesis primer; and an RNA-dependent DNA polymerase; and an RNA polymerase (RNAP) (e.g., a T7-type RNAP, e.g., T7 RNAP, T3 RNAP, or SP6 RNAP, EPICENTRE).

Another embodiment of the invention is a kit comprising RNA 5' polyphosphatase (e.g., an aluminum-inducible RNA 5' polyphosphatase, e.g., *Escherichia coli* RNA 5' polyphosphatase I (*E. coli* RPP I or RPP I, EPICENTRE) or *Shigella* RNA 5' polyphosphatase I) in combination with and at least one other component selected from the group consisting of: RNA 5' monophosphatase (e.g., RNA 5' monophosphatase 1 (RMP1, EPICENTRE); an alkaline phosphatase (e.g., APEX™ Alkaline Phosphatase (EPICENTRE), shrimp alkaline phosphatase (USB, Cleveland, Ohio), or Arctic Alkaline Phosphatase (New England Biolabs, MA); a nucleic acid pyrophosphatase (e.g., tobacco acid pyrophosphatase (TAP), EPICENTRE); a decapping enzyme (e.g., yeast decapping enzyme, mammalian decapping enzyme, *Arabidopsis thaliana* decapping enzyme, or vaccinia virus decapping enzymes D9 or D10); a capping enzyme (e.g., poxvirus capping enzyme, *Saccharomyces cerevisiae* capping enzyme, or SCRIPTCAP™ capping enzyme kit, (EPICENTRE)); RNA ligase (e.g., T4 RNA ligase, EPICENTRE, or bacteriophage TS2126 RNA ligase); an RNA acceptor oligonucleotide; a poly(A) polymerase (e.g., *E. coli* poly(A) polymerase, EPICENTRE) or a poly(U) polymerase; an RNA-dependent DNA polymerase (RT) (e.g., SUPERSCRIPT RT (Invitrogen, Carlsbad, Calif.), AMV RT, MMLV RT (EPICENTRE)); a first-strand cDNA synthesis primer; RNase H (e.g., *E. coli* RNase H or HYBRIDASE™ RNase H, EPICENTRE); a second-strand cDNA synthesis primer; an RNA polymerase (RNAP) (e.g., a T7-type RNAP, e.g., T7 RNAP, T3 RNAP, or SP6 RNAP, EPICENTRE); 5' exoribonuclease (XRN) (e.g., *Saccharomyces cerevisae* Xrn I exoribonuclease (Xrn I), or TERMINATOR™ 5'-phosphate-dependent exonuclease, EPICENTRE); polynucleotide kinase (PNK) (e.g., T4 PNK, EPICENTRE); and an RNA molecule that has a 5' triphosphate or diphosphate group wherein the beta or gamma phosphate of said group is labeled.

Another embodiment of the invention is a kit comprising RNA 5' monophosphatase (RMP) (e.g., RNA 5' monophosphatase 1 (RMP1, EPICENTRE), in combination with at least one other component selected from the group consisting of: an RNA 5' polyphosphatase (e.g., an aluminum-inducible RNA 5' polyphosphatase, e.g., *Escherichia coli* RNA 5' polyphosphatase I (*E. coli* RPP I or RPP I, EPICENTRE) or *Shigella* RNA 5' polyphosphatase I); an alkaline phosphatase (e.g., APEX™ Alkaline Phosphatase (EPICENTRE), shrimp alkaline phosphatase (USB, Cleveland, Ohio), or Arctic Alkaline Phosphatase (New England Biolabs, MA); a nucleic acid pyrophosphatase (e.g., tobacco acid pyrophosphatase (TAP), EPICENTRE); a decapping enzyme (e.g., yeast decapping enzyme, mammalian decapping enzyme, *Arabidopsis*

*thaliana* decapping enzyme, or vaccinia virus decapping enzymes D9 or D10); a capping enzyme (e.g., poxvirus capping enzyme, *Saccharomyces cerevisiae* capping enzyme, or SCRIPTCAP™ capping enzyme kit, (EPICENTRE)); RNA ligase (e.g., T4 RNA ligase, EPICENTRE, or bacteriophage TS2126 RNA ligase); an RNA acceptor oligonucleotide; poly (A) polymerase (e.g., *E. coli* poly(A) polymerase, EPICENTRE); an RNA-dependent DNA polymerase (RT) (e.g., SUPERSCRIPT RT (Invitrogen, Carlsbad, Calif.), AMV RT, MMLV RT (EPICENTRE)); a first-strand cDNA synthesis primer; RNase H (e.g., *E. coli* RNase H or HYBRIDASE™ RNase H, EPICENTRE); a second-strand cDNA synthesis primer; an RNA polymerase (RNAP) (e.g., a T7-type RNAP, e.g., T7 RNAP, T3 RNAP, or SP6 RNAP, EPICENTRE); 5' exoribonuclease (XRN) (e.g., TERMINATOR™ 5'-phosphate-dependent exonuclease, EPICENTRE, or *Saccharomyces cerevisae* Xrn I exoribonuclease (Xrn I)); polynucleotide kinase (PNK) (e.g., T4 PNK, EPICENTRE); and an RNA molecule that has a 5' triphosphate or diphosphate group wherein the beta or gamma phosphate of said group is labeled.

The methods, kits and compositions of the invention have wide applicability. For example, the nucleic acid molecules generated using them can be used for synthesizing cDNA from any desired full-length RNA (e.g., full-length capped eukaryotic mRNA, miRNA, full-length uncapped eukaryotic primary RNA, including non-coding RNA, or full-length prokaryotic primary mRNA) and for cloning said cDNA, for RNA amplification of said desired RNA, and for capture and identification of the exact 5' ends of said desired RNA (e.g., by sequencing, or by using methods such as random amplification of cDNA ends (RACE), exon arrays, or other microarrays).

In general, any of methods 1 through 26 or any of the kits and compositions disclosed herein provide improvements over and can be used for the same purposes and applications as described in World Patent Application WO 2007/117039 A1.

In some embodiments of the invention, any of methods 1 through 26 or any of the kits and compositions disclosed herein is used, either separately or in combination, to generate nucleic acid molecules consisting of labeled or unlabeled 5'-ligation-tagged RNA, first-strand cDNA, second-strand cDNA, double-stranded cDNA, or RNA synthesized by in vitro transcription of the double-stranded cDNA from each of two different samples and said molecules are used to analyze, identify (e.g., sequence), quantify or determine the relative abundance of the nucleic acid molecules (e.g., by measuring the abundance of one or more nucleic acid molecules from or derived from one sample compared to the abundance of the nucleic acid molecules in another sample, e.g., using a microarray or real-time PCR), annotate, and find the biological function of the RNA molecules in the sample from which said nucleic acid molecules are generated. In some embodiments, the nucleic acid molecules are analyzed, identified, quantified, sequenced, annotated, or the biological function is found for research purposes, whereas in other embodiments this work is performed for commercial purposes (e.g., to find and express genes for industrial, agricultural, or other commercial applications, or to use the information for medical, therapeutic, or diagnostic applications in humans or animals.)

Definitions

The present invention will be understood and interpreted based on the definitions of terms as defined below.

When the terms "for example", "e.g.", "such as", "include", "including" or variations thereof are used herein, these terms will not be deemed to be terms of limitation, and will be interpreted to mean "but not limited to" or "without limitation."

An "acceptor oligonucleotide", as used herein, means an oligonucleotide that has a 3' hydroxyl group that is capable of being ligated to the 5' end of an RNA that has a 5' phosphate group by the action of an RNA ligase, wherein the RNA that has a 5' phosphate group is referred to as the "donor." An acceptor oligonucleotide that consists of ribonucleotides is referred to herein as an "RNA acceptor oligonucleotide" or an "RNA acceptor."

"Affinity binding molecules" or a "specific binding pair" herein means molecules that have affinity for and "bind" to each other under certain conditions, referred to as "binding conditions." Biotin and streptavidin or avidin are examples of a "specific binding pair" or "affinity binding molecules", but the invention is not limited to use of this particular specific binding pair.

An "affinity molecule", as defined herein, means a molecule that is capable of specifically binding to another substance that is referred to herein as an "affinity binding substance." The affinity molecule and the affinity binding substance make up or comprise "affinity binding molecules" or a "specific binding pair." Affinity molecules (e.g., biotin or digoxigenin) can be conjugated to other molecules (e.g., to RNA or DNA) and affinity binding substances (e.g., streptavidin or avidin, which bind biotin, or a specific antibody that binds digoxigenin) can be covalently conjugated or non-covalently bound to a solid surface using methods known in the art (e.g., using reagents and methods as described in Avidin-Biotin Chemistry: A Handbook, by D. Savage et al., Pierce Chemical Company, 1992, and in Handbook of Fluorescent Probes and Research Products, Ninth Edition, by R.P. Hoagland, Molecular Probes, Inc., and in BIOCONJUGATE Techniques, by Greg T. Hermanson, Published by Academic Press, Inc., San Diego, Calif., 1996). Affinity molecules that are conjugated to DNA or RNA can also be synthesized using an oligonucleotide synthesizer using reagents and methods known in the art.

The term "binding" according to the present invention means the interaction between an affinity molecule and an affinity binding substance as a result of non-covalent bonds, such as, hydrogen bonds, hydrophobic interactions, van der Waals bonds, and ionic bonds. Without being bound by theory, it is believed in the art that these kinds of non-covalent bonds result in binding, in part due to complementary shapes or structures of the molecules involved in the specific binding pair. Based on the definition for "binding," and the wide variety of affinity binding molecules or specific binding pairs, it is clear that binding conditions vary for different specific binding pairs. Those skilled in the art can easily find or determine conditions whereby, in a sample, binding occurs between the affinity binding molecules. In particular, those skilled in the art can easily determine conditions whereby binding between affinity binding molecules that would be considered in the art to be "specific binding" can be made to occur. As understood in the art, such specificity is usually due to the higher affinity between the affinity binding molecules than for other substances and components (e.g., vessel walls, solid supports) in a sample. In certain cases, the specificity might also involve, or might be due to, a significantly more rapid association of affinity binding molecules than with other substances and components in a sample.

A "cap" or a "cap nucleotide" is a modified guanine nucleotide that is joined to the 5' end of a primary RNA transcript. The RNA that has the cap nucleotide joined to its 5' end is referred to as "capped RNA" or "capped RNA transcript" or "capped transcript." A common cap nucleoside is 7-methylguanosine or N7-methylguanosine (sometimes referred to as "standard cap"), which has a structure designated as "m$^7$G," in which case the capped RNA or "m$^7$G-capped RNA" has a structure designated as m$^7$G(5')ppp(5')N$_1$(pN)$_x$—OH(3'), or more simply, as m$^7$ GpppN$_1$(pN)$_x$ or m$^7$G(5')ppp(5')N, wherein m$^7$G represents the 7-methylguanosine cap nucleoside, ppp represents the triphosphate bridge between the 5' carbons of the cap nucleoside and the first nucleotide of the primary RNA transcript, N$_1$(pN)$_x$—OH(3') represents the primary RNA transcript, of which N$_1$ is the most 5'-nucleotide, "p" represents a phosphate group, "G" represents a guanosine nucleoside, "m$^7$" represents the methyl group on the 7-position of guanine, and "(5')" indicates the position at which the "p" is joined to the ribose of the cap nucleotide and the first nucleoside of the mRNA transcript ("N"). In addition to this "standard cap," a variety of other naturally-occurring and synthetic cap analogs are known in the art. RNA that has any cap nucleotide is referred to as "capped RNA." The capped RNA can be naturally occurring from a biological sample or it can be obtained by in vitro capping of RNA that has a 5' triphosphate group or RNA that has a 5' diphosphate group with a capping enzyme system (e.g., vaccinia capping enzyme system or *Saccharomyces cerevisiae* capping enzyme system). Alternatively, the capped RNA can be obtained by in vitro transcription (IVT) of a DNA template that contains an RNA polymerase promoter, wherein, in addition to the GTP, the IVT reaction also contains a dinucleotide cap analog (e.g., a m$^7$ GpppG cap analog or an N$^7$-methyl, 2'-O-methyl-GpppG ARCA cap analog or an N$^7$-methyl, 3'-O-methyl-GpppG ARCA cap analog) using methods known in the art (e.g., using an AMPLICAP™ T7 capping kit (EPICENTRE)).

In vivo, capping of a 5'-triphosphorylated primary mRNA transcript occurs via several enzymatic steps (e.g., see Martin, S A et al., J. Biol. Chem. 250: 9322, 1975; Myette, J R and Niles, E G, J. Biol. Chem. 271: 11936, 1996; M A Higman, et al., J. Biol. Chem. 267: 16430, 1992).

The following enzymatic reactions are involved in capping of eukaryotic mRNA:

(1) RNA triphosphatase cleaves the 5'-triphosphate of mRNA to a diphosphate, pppN$_1$(p)N$_x$—OH(3')→ppN$_1$(pN)$_x$—OH(3')+Pi; and then (2) RNA guanyltransferase catalyzes joining of GTP to the 5'-diphosphate of the most 5' nucleotide (N$_1$) of the mRNA, ppN$_1$(pN)$_x$—OH(3')+GTP→G(5')ppp(5')N$_1$(pN)$_x$—OH(3')+PPi; and finally, (3) guanine-7-methyltransferase, using S-adenosyl-methionine (AdoMet) as a co-factor, catalyzes methylation of the 7-nitrogen of guanine in the cap nucleotide, G(5')ppp(5')N$_1$(pN)$_x$—OH(3')+AdoMet→m$^7$G(5')ppp(5')N$_1$(pN)$_x$—OH(3')+AdoHyc.

RNA that results from the action of the RNA triphosphatase and the RNA guanyltransferase enzymatic activities, as well as RNA that is additionally methylated by the guanine-7-methyltransferase enzymatic activity, is referred to herein as "5' capped RNA" or "capped RNA", and a "capping enzyme system" or, more simply, a "capping enzyme" herein means any combination of one or more polypeptides having the enzymatic activities that result in "capped RNA." Capping enzyme systems, including cloned forms of such enzymes, have been identified and purified from many sources and are well known in the art (e.g., see Shuman, S, Prog. Nucleic Acid Res. Mol. Biol. 66: 1-40, 2001; Shuman, S, Prog. Nucleic Acid Res. Mol. Biol. 50: 101-129, 1995; Shuman, S et al., J. Biol. Chem. 255: 11588, 1980; Banerjee, A K, Microbiol. Rev. 44: 175-205, 1980; Wang, S P et al., Proc. Natl. Acad. Sci. USA 94: 9573, 1997; Higman M. A. et al., J. Biol. Chem. 267: 16430, 1992; Higman, M A et al., J. Biol. Chem. 269: 14974-14981, 1994; Myette, J R and Niles, E G, J. Biol. Chem. 271: 11936-11944, 1996). Any capping enzyme system that can convert uncapped RNA that has a 5' polyphosphate to capped RNA can be used in any of the embodiments of the present invention that provide or use a capping enzyme system. In some embodiments, the capping enzyme system is a poxvirus capping enzyme system. In some preferred embodiments, the capping enzyme system is vaccinia virus capping enzyme. In some embodiments, the capping enzyme system is *Saccharomyces cerevisiae* capping enzyme. Also, in view of the fact that genes encoding RNA triphosphatase, RNA guanyltransferase and guanine-7-methyltransferase from one source can complement deletions in one or all of these genes from another source, the capping enzyme system can originate from one source, or one or more of the RNA triphosphatase, RNA guanyltransferase, and/or guanine-7-methyltransferase activities can comprise a polypeptide from a different source.

A "decapping enzyme," as defined herein, means an enzyme that converts a capped RNA to an RNA that has a 5' monophosphate group under conditions wherein it does not convert RNA that has a 5' polyphosphate group to RNA that has a 5' monophosphate group. In eukaryotes, long capped RNA is typically converted to an RNA that has a 5' monophosphate group by a decapping enzyme consisting of a Dcp1/Dcp2 complex, of which, Dcp2 is the catalytic subunit and the decapping enzyme is referred to herein as a "Dcp2-type decapping enzyme." Thus, in preferred embodiments of the invention wherein a decapping enzyme is used, the decapping enzyme is a Dcp2-type decapping enzyme. A Dcp2-type decapping enzyme is a member of the Nudix superfamily of enzymes, which enzymes share a conserved amino acid sequence called the Nudix (or MutT) motif or Nudix box, Dunckley, T. and Parker, R. EMBO J. 18: 5411-5422, 1999; van Dijk, E et al., EMBO J. 21: 6915-6924, 2002; Steiger, M et al., RNA 9: 231-238, 2003; Xu, W et al. J. Biol. Chem. 279: 24861-24865, 2004; Gunawardana, D et al., Nucleic Acids Res. 36: 203-216, 2008 all of which are herein incorporated by reference in their entireties). A DcpS-type enzyme, which digests short capped RNAs, including dinucleotides, to RNAs that have a 5' diphosphate group is not a decapping enzyme as defined herein.

As used herein, the term "enzyme" refers to protein molecules or protein molecule aggregates that are responsible for catalyzing chemical and biological reactions. In general, a method, composition, or kit of the invention is not limited to use of a particular enzyme from a particular source. Rather, a method, composition, or kit of the present invention comprises any enzyme from any source that has an equivalent enzymatic activity to the particular enzyme disclosed herein with respect to the particular method, composition, or kit. By way of example, an RNA 5' polyphosphatase can be *Escherichia coli* or *Shigella* RNA 5' polyphosphatase I, or it can be another RNA 5' polyphosphatase enzyme that converts RNA that has a 5' polyphosphate group to RNA that has a 5' monophosphate group under suitable reaction conditions; an RNA-dependent DNA polymerase can be AMV reverse transcriptase; MMLV reverse transcriptase; SUPERSCRIPT I, SUPERSCRIPT II, SUPERSCRIPT III, or AMV THERMOSCRIPT reverse transcriptase (INVITROGEN); or MONSTERSCRIPT reverse transcriptase (EPICENTRE), or it can be another enzyme that can synthesize DNA using RNA as a template and an oligonucleotide primer that anneals to a complementary sequence therein under suitable reaction conditions; a polynucleotide kinase can be T4 polynucleotide kinase or it can be another enzyme that can transfer a monophosphate group from ATP or another nucleoside-5'-triphosphate to the 5' end of RNA that has a 5' hydroxyl group under suitable reaction conditions; a poly(A) polymerase can be *Escherichia coli* poly(A) polymerase encoded by the pcnB gene or it can be another enzyme that, in the presence of ATP, can synthesize a poly(A) tail on the 3' end of RNA that has a 3' hydroxyl group in the absence of a nucleic acid template under suitable reaction conditions; ribonuclease H can be *Escherichia coli* RNase H or HYBRIDASE™ Thermostable RNase H (EPICENTRE, Madison, Wis.) or it can be another enzyme that, under suitable reaction conditions, digests RNA that is annealed to DNA but does not digest single-stranded RNA or RNA that is annealed to RNA; a nucleic acid pyrophosphatase can be tobacco acid pyrophosphatase or it can be another enzyme that, under suitable reaction conditions, generates RNA that has a 5' monophosphate group by cleaving the triphosphate bridge of $m^7G$-capped RNA; and an alkaline phosphatase can be APEX™ Alkaline Phosphatase (EPICENTRE, Madison, Wis.) or shrimp alkaline phosphatase or Arctic Alkaline Phosphatase (New England Biolabs, MA) or it can be another enzyme that, under suitable reaction conditions, converts RNA that has a 5' polyphosphate group or RNA that has a 5' monophosphate group to RNA that has a 5' hydroxyl group. Still further, the methods of the present invention also include embodiments wherein any one particular enzyme that is provided and used in a step of the method is replaced by a combination of two or more enzymes which, when used in combination, whether used separately in a stepwise manner or used together at the same time reaction mixture, result in synthesis of RNA that is identical to the RNA that synthesized using the one particular enzyme. The methods, buffers, and reaction conditions presented herein, including in the examples, are presently preferred for the embodiments of the methods, compositions, and kits of the present invention. However, other enzyme storage buffers, reaction buffers, and reaction conditions for use of some of the enzymes of the invention are known in the art, which may also be suitable for use in the present invention, and are included herein.

Any enzyme that is used in a method, composition or kit of the present invention can be a native protein or a recombinant protein. The term "native protein" is used herein to indicate a protein isolated from a naturally occurring (i.e., a non-recombinant) source. The term "recombinant protein" or "recombinant polypeptide" as used herein refers to a protein molecule expressed from a recombinant DNA molecule. Molecular biological techniques may be used to produce a recombinant form of a protein with identical or similar properties as compared to the native form of the protein. Variants of the native sequence may also be made to, for example, improve expression, purification, or other desired properties of the polypeptide. A recombinant protein can be a fusion protein. As used herein, the term "fusion protein" refers to a chimeric protein containing the protein of interest (e.g., *E. coli* RNA 5' polyphosphatase I (RPP I) or fragments thereof) joined to an exogenous protein fragment (e.g., the fusion partner which contains a non-RPP I protein). The fusion partner may enhance the solubility of the protein with the desired enzymatic activity as expressed in a host cell, may provide an affinity tag to allow purification of the recombinant fusion protein from the host cell or culture supernatant, or both. If desired, the fusion protein may be removed from the protein of interest by a variety of enzymatic or chemical means known to the art.

In preferred embodiments of the present invention, the enzyme composition that is used in a method, composition, or kit comprises a purified protein. As used herein, the term "purified" or "to purify" means the result of any process that removes some of a contaminant from the component of interest, such as the protein. For example, a particular desired protein (e.g., RPP I or RMP1) is purified by removal of other contaminating undesired proteins, nucleic acid, carbohydrate, lipid and/or small biochemical molecules. The removal of contaminants results in an increase in the percentage of desired protein in the composition. For example, in preferred embodiments, the RPP I or RMP1 composition is purified so as to be free of contaminating nucleic acids and other enzymes with activity on nucleic acids.

In some preferred embodiments, the desired protein (e.g., RPP I or RMP1) is obtained by expression of the gene (and/or functional variants and homologues thereof) in a plasmid or other vector that is replicated and expressed in *Escherichia coli* cells, or by expression of the gene (and/or functional variants and homologues thereof) that is inserted into the chromosome in *Escherichia coli* cells using a TRANSPOSOME™ system (e.g., an EZ-Tn5™ TRANSPOSOME™ system (EPICENTRE, Madison, Wis.) since the enzyme obtained from such a recombinant source is of a higher purity, free from contaminating enzymatic activities, and generally at a higher enzyme concentration than is obtained from non-recombinant sources.

The term "gene" as used herein, refers to a DNA sequence that comprises control and coding sequences necessary for the production of the encoded polypeptide or protein precursor. The polypeptide can be encoded by a full-length coding sequence or by any portion of the coding sequence, as long as the desired protein activity is retained.

In preferred embodiments of the invention, the enzyme is "stabilized", by which we mean that the enzyme is sufficiently pure of proteases and other contaminants which contribute to degradation and loss of enzyme activity and is provided in a formulation of enzyme storage buffer in which there is no significant loss of activity during storage at minus 20 degrees C. for six months. One suitable enzyme storage buffer for providing a stabilized composition of many enzymes (e.g., *E. coli* 5' RPP I, T4 PNK, T4 RNA ligase) comprises a 50% glycerol solution containing 50 mM Tris-HCL (pH 7.5), 100 mM NaCl, 100 mM EDTA, 1 mM DTT and 0.1% of the non-ionic detergent Triton X-100.

Moreover, variant forms of the proteins of the invention (e.g., RNA 5' polyphosphatase or RNA 5' monophosphatase) are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of the enzymes disclosed herein that contain conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., Biochemistry, pg. 17-21, 2nd ed, WH Freeman and Co., 1981). It can be readily determined whether a change in the amino acid sequence of a peptide results in a functional polypeptide by assessing the ability of the variant peptide to function in a fashion similar to the wild-type protein. Peptides having more than one replacement can readily be tested in the same manner.

More rarely, a variant of an enzyme used in a method, composition, or kit of the present invention includes "non-conservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

Variants may be produced by methods such as directed evolution or other techniques for producing combinatorial libraries of variants, described in more detail below. In still other embodiments of the present invention, the nucleotide sequences of the present invention may be engineered in order to alter the coding sequence an enzyme of a method, composition, or kit of the present invention (e.g., by engineering the sequence of an RNA 5' polyphosphatase or RNA 5' monophosphatase), including alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

Still other embodiments of the present invention provide mutant or variant forms of an enzyme of the present invention. It is possible to modify the structure of a peptide having an activity (e.g., of RNA 5' polyphosphatase) for such purposes as enhancing activity, or stability (e.g., ex vivo shelf life, and/or resistance to proteolytic degradation in vivo). Such modified peptides are considered functional equivalents of peptides having an activity of the subject proteins as defined herein. A modified peptide can be produced in which the amino acid sequence has been altered, such as by amino acid substitution, deletion, or addition.

Moreover, as described above, variant forms (e.g., mutants) of the subject proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present proteins (e.g., of RNA 5' polyphosphatase or RNA 5' monophosphatase), as well as truncation mutants (e.g., using the EZ-Tn5™ Protein Truncation Kit, EPICENTRE), and is especially useful for identifying potential variant sequences (i.e., mutants) that are functional (e.g., in RNA 5' polyphosphatase or RNA 5' monophosphatase activity). The purpose of screening such combinatorial libraries is to generate, for example, novel enzyme variants that have improved or altered enzymatic activity.

Therefore, in some embodiments of the present invention, protein variants (e.g., variants of RNA 5' polyphosphatase or RNA 5' monophosphatase) are engineered by the present method to provide altered (e.g., increased or decreased) enzymatic activity. In other embodiments, protein variants are engineered to provide heat-stable (i.e., "thermostable") or heat-labile activity for particular applications. In other embodiments of the present invention, combinatorially-derived variants are generated which have substrate variability different than that of a naturally occurring protein. Such proteins, when expressed from recombinant DNA constructs, find use in the methods described herein.

Still other embodiments of the present invention provide protein variants (e.g., variants of RNA 5' polyphosphatase or RNA 5' monophosphatase) that have intracellular half-lives dramatically different than the corresponding wild-type protein. For example, the altered protein can be rendered either more stable or less stable to proteolytic degradation or other cellular process that result in destruction of, or otherwise inactivate the protein. Such variants, and the genes which encode them, can be utilized to alter the location of expression by modulating the half-life of the protein. For instance, a short half-life can give rise to more transient biological effects and, when part of an inducible expression system, can allow tighter control of protein levels within the cell.

In still other embodiments of the present invention, protein variants (e.g., variants of RNA 5' polyphosphatase or RNA 5' monophosphatase) are generated by the combinatorial approach to act as antagonists, in that they are able to interfere with the ability of the corresponding wild-type protein to regulate cell function. In some embodiments of the combinatorial mutagenesis approach of the present invention, the amino acid sequences for a population of protein homologs, variants or other related proteins are aligned, preferably to promote the highest homology possible. Such a population of variants can include protein homologs (e.g., homologs of RNA 5' polyphosphatase or RNA 5' monophosphatase) from one or more species or sub-species, or protein variants from the same species or sub-species but which differ due to mutation or polymorphisms. Amino acids that appear at each position of the aligned sequences are selected to create a degenerate set of combinatorial sequences.

In a preferred embodiment of the present invention, the combinatorial protein library is produced by way of a degenerate library of genes encoding a library of polypeptides which each include at least a portion of potential protein sequences. For example, a mixture of synthetic oligonucleotides can be enzymatically ligated into gene sequences such that the degenerate set of potential sequences (e.g., potential sequences of RNA 5' polyphosphatase or RNA 5' monophosphatase) are expressible as individual polypeptides, or alternatively, as a set of larger fusion proteins (e.g., for phage display) containing the set of sequences therein.

There are many ways by which the library of potential protein homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential protein sequences. The synthesis of degenerate oligonucleotides is well known in the art (See e.g., Narang, Tetrahedron Lett., 39: 39, 1983; Itakura et al., Recombinant DNA, in Walton (ed.), Proceedings of the 3rd Cleveland Symposium on Macromolecules, Elsevier, Amsterdam, pp 273-289, 1981; Itakura et al., Annu Rev. Biochem., 53: 323, 1984; Itakura et al., Science 198: 1056, 1984; Ike et al., Nucl. Acid Res., 11: 477, 1983). Such techniques have been employed in the directed evolution of other proteins (See e.g., Scott et al., Science 249: 386, 1980; Roberts et al., Proc. Natl. Acad. Sci. USA 89: 2429, 1992; Devlin et al., Science 249: 404, 1990; Cwirla et al., Proc. Natl. Acad. Sci. USA 87: 6378, 1990; as well as U.S. Pat. Nos. 5,223,409; 5,198,346; and 5096815).

It is contemplated that the nucleic acids that encode the proteins can be utilized as starting nucleic acids for directed evolution. These techniques can be utilized to develop enzyme variants having desirable properties such as increased, decreased, or altered enzymatic activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458, 1996; Eckert and Kunkel, PCR Methods Appl., 1: 17-24, 1991; Caldwell and Joyce, PCR Methods Appl., 2: 28, 1992; and Zhao and Arnold, Nuc. Acids Res. 25: 1307, 1997). After mutagenesis, the resulting clones are selected for desirable activity. Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324, 1994; U.S. Pat. Nos. 5,837,458; 5,830,721; 5,811,238; 5,733,731). Gene shuffling involves random fragmentation of several mutant DNAs followed by their reassembly by PCR into full length molecules. Examples of various gene shuffling procedures include assembly following DNase treatment, the staggered extension process, and random priming in vitro recombination. In the DNase-mediated method, DNA segments isolated from a pool of positive mutants are cleaved into random fragments with DNase I and subjected to multiple rounds of PCR with no added primer. The lengths of random fragments approach that of the uncleaved segment as the PCR cycles proceed, resulting in mutations present in different clones becoming mixed and accumulating in some of the resulting sequences. Multiple cycles of selection and shuffling have led to the functional enhancement of several enzymes (Stemmer, Nature, 370:398, 1994; Stemmer, Proc. Natl. Acad. Sci. USA, 91: 10747, 1994; Crameri et al., Nat. Biotech., 14: 315, 1996; Zhang et al., Proc. Natl. Acad. Sci. USA, 94: 4504, 1997; and Crameri et al., Nat. Biotech., 15: 436, 1997).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of protein homologs or variants. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Fragments of the nucleic acids and proteins of the present invention may also be used, so long as the fragments encode or possess the desired enzymatic activity.

As used herein, "5' exoribonuclease" ("XRN") means a 5' exonuclease that has greater than 20-fold more 5'-to-3' exonuclease activity for a single-stranded RNA substrate that has a 5'-monophosphorylated terminus than for the same RNA substrate that has a 5'-triphosphorylated or 5'-capped terminus. Enzyme activity of a 5' exoribonuclease of the invention can be measured using a number of different methods. A suitable method for assaying activity and determining relative activity using RNA substrates with a 5'-triphosphate, a 5'-cap, or a 5'-monophosphate are described by Stevens and Poole (J. Biol. Chem., 270: 16063, 1995). A preferred composition of 5' exoribonuclease is *Saccharomyces cerevisiae* Xrn1p/5' exoribonuclease 1 (or "Xrn I exoribonuclease" or "Xrn 1 5' exoribonuclease" or "5' Xrn1p exoribonuclease"), which can be prepared using methods known in the art. In some embodiments, 5' exoribonuclease is obtained by expression of the *Saccharomyces cerevisiae* XRN1 gene that has been cloned in a plasmid, and then replicated and expressed in *Escherichia coli* cells.

An "oligo cap" or "oligonucleotide cap" is an acceptor oligonucleotide that is ligated to the 5' end of a 5'-monophosphorylated RNA molecule by the action of RNA ligase as part of an "oligo capping" method. In most embodiments of the oligo capping methods in the art, the oligo cap is an RNA acceptor oligonucleotide. An "oligo cap" differs from an "m$^7$G cap" that is typically found on eukaryotic mRNA molecules. The cap on eukaryotic mRNA (e.g., m$^7$G cap) and some other eukaryotic RNA molecules is sometimes referred to herein as an "m$^7$G-cap" or a "cap nucleotide" or a "nucleotide cap" to distinguish it from an "oligonucleotide cap" or an "oligo cap." We sometimes refer to the RNA with the cap nucleotide (e.g., eukaryotic mRNA) herein as "m$^7$G-capped RNA", even though the cap nucleotide may have other modifications besides the N7-methyl group of the guanine base.

As used herein a "nucleic acid pyrophosphatase" or "pyrophosphatase" ("PPase") means an enzyme that cleaves pyrophosphate bonds of the triphosphate bridge of m7G-capped RNA or of the 5' triphosphate in primary RNA that has a 5' triphosphate to generate RNA that has a 5' monophosphate. The nucleic acid pyrophosphatase can be tobacco acid pyrophosphatase ("TAP") or it can be any other enzyme that has similar activity in the method. For example, baculovirus phosphatase (BVP) (Takagi, T. et al., Proc. Natl. Acad. Sci. USA 95: 9808-9812, 1998; Gross, C. H. and Shuman, S., J. Virology 72: 7057-7063, 1998), human PIR1 protein (Deshpande, T. et al., J. Biol. Chem. 274: 16590-16594, 1999), and *E. coli* RppH protein (Deana, A et al., Nature 451: 355-358, 2008) have been reported to convert 5'-triphosphorylated RNA to 5'-monophosphorylated RNA, but their activities on capped RNA have not been reported. It is contemplated that this activity would be tested and, that any of the proteins, selected from among BVP, PIR1, and RppH protein, that has activity in converting capped RNA to RNA that has a 5' monophosphate group can be used as the nucleic acid pyrophosphatase in any of the methods of the present invention. Tobacco acid pyrophosphatase is a preferred nucleic acid pyrophosphatase for the methods of the present invention.

"PolyA polymerase" ("PAP") means a template-independent RNA polymerase found in most eukaryotes, prokaryotes, and eukaryotic viruses that selectively uses ATP to incorporate AMP residues to 3'-hydroxylated ends of RNA. Since PAP enzymes that have been studied from plants, animals, bacteria and viruses all catalyze the same overall reaction (e.g., see Edmonds, M, Methods Enzymol., 181; 161-180, 1990), are highly conserved structurally (e.g., see Gershon, P, Nature Structural Biol. 7: 819-821, 2000), and lack intrinsic specificity for particular sequences or sizes of RNA molecules if the PAP is separated from proteins that recognize AAUAAA polyadenylation signals (Wilusz, J and Shenk, T, Cell 52: 221, 1988), purified wild-type and recombinant PAP enzymes from any of a variety of sources can be used in the kits and methods of the present invention.

A "primary RNA" or "primary RNA transcript" means the RNA molecule that is synthesized by an RNA polymerase in vivo or in vitro and which RNA molecule has a triphosphate on the 5'-carbon of its most 5' nucleotide.

"Replication" means the formation or synthesis of an RNA molecule by an RNA-dependent RNA polymerase (or "replicase") using an RNA molecule as a template.

"RNA amplification" according to the present invention is a method that that results in synthesis of an RNA product wherein there is an increase in the number of copies of an RNA sequence or its complementary sequence compared to the number of copies of the sequence present in a sample. By way of example, a method that uses an oligo(dT) promoter primer as a first-strand cDNA synthesis primer can be used for synthesis of antisense RNA (aRNA) as described by Van Gelder, R. N., et al. (Proc. Natl. Acad. Sci. USA 87: 1663, 1990). Kits for this purpose are commercially available and can be used, including 1-round and 2-round amplification kits such as various 1-round and 2-round TARGETAMP™ Aminoallyl-aRNA Amplification Kits or TARGETAMP™ aRNA Amplification Kits available from EPICENTRE (Madison, Wis.). Alternatively, a second-strand cDNA synthesis primer (or a PCR primer) that exhibits, in its 5' portion, a sequence for one strand of an RNA polymerase promoter and, in its 3' portion, a sequence that is complementary to a sequence exhibited by a tag that is on the 3' end of the first-strand cDNA can be used in an RNA amplification method for synthesizing sense RNA (e.g., using methods described herein). Thus, in these embodiments, an RNA acceptor oligonucleotide is ligated to the 5' end of RNA of interest comprising RNA that has a 5' monophosphate group, thereby obtaining 5'-ligation-tagged RNA, which is then used as a template for synthesis of the first-strand cDNA using an RNA-dependent DNA polymerase. Then, double-stranded cDNA that contains the RNA polymerase promoter is synthesized using a DNA polymerase and the second-strand cDNA synthesis primer (or a PCR primer). Finally, amplified sense RNA is synthesized by in vitro transcription of the double-stranded cDNA using an RNA polymerase that binds and initiates transcription from the RNA polymerase promoter. If the RNA of interest in the sample does not already have 5' monophosphate group, it is converted to RNA that has a 5' monophosphate group (e.g., using tobacco acid pyrophosphatase to convert RNA of interest comprising both capped RNA and RNA that has a 5' polyphosphate group, or using an RNA polyphosphatase to convert only RNA that has a 5' polyphosphate group).

The present invention is also not limited to RNA amplification methods that require synthesis of double-stranded cDNA. By way of example, the present invention also comprises RNA amplification methods and compositions as described in U.S. Patent Appln. No. 2004/0171041 that use an RNA polymerase that can synthesize RNA using single-stranded templates that are functionally joined to a single-stranded promoter, such as methods that use MINI-V RNA polymerase (available from EPICENTRE in the MINI-V™ In Vitro Transcription Kit); in these embodiments, a single-stranded promoter is joined to either the 5' end of the cDNA or the 3'-end of cDNA that is made by reverse transcription of mRNA using an RNA-dependent DNA polymerase to extend a primer, resulting in synthesis of amplified antisense RNA or amplified sense RNA, respectively, by subsequent in vitro transcription of single-stranded DNA templates (e.g., using MINIV RNA polymerase).

As defined herein, "RNA ligase" means an enzyme or composition of enzyme that is capable of catalyzing the joining or ligating of an RNA acceptor oligonucleotide, which has an hydroxyl group on its 3' end, to an RNA donor, which has a 5' phosphate group on its 5' end. The invention is not limited with respect to the RNA ligase, and any RNA ligase from any source can be used in an embodiment of the methods and kits of the present invention. For example, in some embodiments, the RNA ligase is a polypeptide (gp63) encoded by bacteriophage T4 gene 63; this enzyme, which is commonly referred to simply as "T4 RNA ligase," is more correctly now called "T4 RNA ligase 1" since Ho, C K and Shuman, S (Proc. Natl. Acad. Sci. USA 99: 12709-12714, 2002) described a second RNA ligase (gp24.1) that is encoded by bacteriophage T4 gene 24.1, which is now called "T4 RNA ligase 2." Unless otherwise stated, when "T4 RNA ligase" is used in the present specification, we mean "T4 RNA ligase 1. For example, in some other embodiments, the RNA ligase is a polypeptide derived from or encoded by an RNA ligase gene from bacteriophage TS2126, which infects *Thermus scotoductus*, as disclosed in U.S. Pat. No. 7,303,901 (i.e., bacteriophage TS2126 RNA ligase).

As defined herein, "RNA 5' monophosphatase" or "RNA 5' monophosphatase enzyme" or "RNA 5' monophosphatase composition" or "RMP" means an enzyme or composition of enzyme that is capable of converting RNA that has a 5' monophosphate group to RNA that has a 5' hydroxyl group under conditions wherein said RNA 5' monophosphatase does not substantially digest uncapped primary RNA (meaning RNA that has a 5' triphosphate group) to an RNA that has a 5' hydroxyl group. In different embodiments, a suitable RNA 5' monophosphatase for use in a method of the invention that employs an RNA 5' monophosphatase is an enzyme that converts >50%, >60%, >70%, >80%, >90%, or >90% of a 5'-monophosphorylated RNA in a reaction to RNA that has a 5' hydroxyl group, without substantially digesting 5'-triphosphorylated RNA (e.g., prokaryotic mRNA) in the reaction mixture under the conditions used. For example, in some embodiments, this can be measured using methods known in the art for real-time qRT-PCR using primer pairs for that are suitable for amplifying the 5'-monophosphorylated RNA and the 5'-triphosphorylated RNA. Although RNA 5' monophosphatase is defined herein with respect to its capability of digesting a 5' monophosphate group of RNA to a 5' hydroxyl group, the RNA 5' monophosphatase can also have other enzymatic activities. For example, it will be understood herein that a RNA 5' monophosphatase may (but need not) also have enzymatic activity in removing a 3' monophosphate group from RNA that has a 3' monophosphate group. In addition, RNA 5' monophosphatase may (but need not) also be capable of cleaving a monophosphate group from the end of DNA, a ribonucleotide, a deoxyribonucleotide, or even from a non-nucleic acid substrate. One suitable RNA 5' monophosphatase that can be used in any of the methods that employ an RNA 5' monophosphatase is RNA 5' monophosphatase 1 (RMP1, EPICENTRE, Madison, Wis., USA). The invention is not limited to embodiments comprising RMP1, and any RNA 5' monophosphatase can be used so long as the enzyme functions for its intended purpose of specifically converting RNA that has a 5' monophosphate group to RNA that has a 5' hydroxyl group without converting RNA that has a 5' triphosphate group that is present in the same reaction mixture to an RNA that has a 5' hydroxyl group.

The enzymatic activity of RNA 5' monophosphatase can be defined in various ways using different substrates (e.g., p-nitrophenyl phosphate or a nucleic acid (RNA or DNA) that has a 5' monophosphate group), conditions, and assays. For example, one unit definition that can be used is: "one unit of RNA 5' monophosphatase is the amount of enzyme that dephosphorylates one micromole of p-nitrophenyl phosphate in one minute at 25° C. in 1M diethanoloamine buffer, pH 9.6, that contains 15 mM p-nitrophenyl phosphate, and 5 mM calcium chloride." For example, one other unit definition that can be used is: "one molecular biology unit (MBU) of RNA 5' monophosphatase (e.g., RNA 5' monophosphatase 1 (RMP1), EPICENTRE) is the amount of enzyme that removes the 5' monophosphate group from one microgram of a defined preparation of a nucleic acid substrate that has a 5'-monophosphate group (e.g., for RMP1, an RNA or DNA substrate, e.g., a defined preparation of 16S and/or 23S bacterial ribosomal RNA or a defined DNA that has a 5' monophosphate group) in 60 minutes at 30° C. in a suitable reaction buffer (e.g., for RMP1, one suitable reaction buffer comprises: 33 mM Tris-acetate, pH 7.5, 66 mM potassium acetate, 10 mM magnesium acetate, 5 mM calcium chloride, and 0.5 mM DTT)."

As defined herein, an "RNA 5' polyphosphatase" or "RNA polyphosphatase" means an enzyme or composition of enzyme that converts RNA that has a 5' triphosphate group (e.g., uncapped primary eukaryotic or prokaryotic RNA) or RNA that has a 5' diphosphate group to RNA that has a 5' monophosphate group but that does not convert capped RNA (e.g., m7G-capped to RNA) to RNA that has a 5' monophosphate group. However, in addition to having the enzymatic activities as defined herein, an RNA 5' polyphosphatase can also have other enzymatic activities. For example, it will be understood herein that RNA 5' polyphosphatase can also remove phosphates from any linear polyphosphate comprising two or more phosphates that is joined to the 5' end of an RNA molecule. In addition, RNA 5' polyphosphatase may also be capable of digesting a linear polyphosphate comprising two or more phosphates that is joined to the 5' end of DNA, RNA, a ribonucleotide, a deoxyribonucleotide, or even a non-nucleic acid polyphosphate substrate. Some embodiments of the present invention comprise compositions, kits, and methods that use RNA 5' polyphosphatases encoded by an aluminum-inducible bacterial gene (e.g., *Escherichia coli* RNA 5' polyphosphatase I or "*E. coli* 5' RPP I" or "*E. coli* RPP I", or sometimes simply "RPP I". The purified *E. coli* RNA 5' polyphosphatase I enzyme was found to be approximately a 19-kDa protein. The nucleic acid sequence (SEQ ID NO: 1) and amino acid sequence (SEQ ID NO: 2) of RNA 5' polyphosphatase I were determined (FIG. 4). The term "RNA 5' polyphosphatase", as used herein, can refer to the protein or the gene unless indicated otherwise.

One suitable enzyme storage buffer for providing a stabilized enzyme composition of *E. coli* RNA 5' polyphosphatase I (*E. coli* 5' RPP I) comprises a 50% glycerol solution containing 50 mM Tris-HCL (pH 7.5), 100 mM NaCl, 100 mM EDTA, 1 mM DTT and 0.1% of the non-ionic detergent Triton X-100.

The enzymatic activity of RNA 5' polyphosphatase can be defined in various ways using different substrates (e.g., an NTP, primary RNA, 6,8-difluoro-4-methylumbelliferyl phosphate), conditions, and assays. For example, one unit definition that can be used is: "one unit of RNA 5' polyphosphatase is the amount of enzyme that releases one nanomole of inorganic phosphate from ATP in 60 minutes at 37° C. under standard reaction assay conditions (e.g., for *E. coli* RNA 5' polyphosphatase I, using 1 mM ATP in a reaction buffer consisting of 50 mM HEPES/KOH, pH 7.5, 0.1 M NaCl, 1 mM EDTA, 0.1% BME and 0.01% TRITON X100)."

The methods of the present invention are not limited to the use of *E. coli* 5' RPP I. Any RNA 5' polyphosphatase that has equivalent enzymatic activity to *E. coli* 5' RPP I under the prescribed reaction conditions of the method can be used. As defined herein, "RNA 5' polyphosphatase" or "RNA polyphosphatase" means an enzyme composition that is capable of digesting a 5' triphosphate group of a primary RNA to a 5' monophosphate under conditions wherein said RNA polyphosphatase does not digest the 5' end of capped RNA to a 5' monophosphate. For example, an RNA 5' polyphosphatase can be selected from among *Escherichia coli* RNA 5' polyphosphatase I (*E. coli* RPP I) and *Shigella* RNA 5' polyphosphatase I (Shigella RPP I). However, with respect to a method of the invention, the enzyme can be any enzyme from any source that has RNA 5' polyphosphatase activity in the particular method. For example, baculovirus phosphatase (BVP) (Takagi, T. et al., Proc. Natl. Acad. Sci. USA 95: 9808-9812, 1998; Gross, C. H. and Shuman, S., J. Virology 72: 7057-7063, 1998), human PIR1 protein (Deshpande, T. et al., J. Biol. Chem. 274: 16590-16594, 1999), and *E. coli* RppH protein (Deana, A et al., Nature 451: 355-358, 2008) have been reported to convert 5'-triphosphorylated RNA to 5'-monophosphorylated RNA, but their activities on capped RNA have not been reported. It is contemplated that this activity would be tested and, that any of the proteins, selected from among BVP, PIR1, and RppH protein, that does not have activity in converting capped RNA to RNA that has a 5' monophosphate group can be used as the RNA polyphosphatase in any of the methods of the present invention that employ an RNA polyphosphatase.

As defined herein, "RNase H" means an enzyme or composition of enzyme that specifically digests the RNA that is in an RNA:DNA hybrid without digesting DNA or unhybridized RNA that is present in the same reaction mixture. Exemplary RNase H enzymes include *E. coli* RNase H, HYBRIDASE™ thermostable RNase H, and Thermus RNase H (e.g., Tth or Tfl RNase H). However, the invention is not limited with respect to the RNase H so long as it functions for its intended purpose of specifically digesting RNA that is annealed to DNA in an RNA:DNA hybrid.

As defined herein, "RNase I" means an enzyme or composition of enzyme that is capable of specifically cleaving single-stranded RNA between all dinucleotide pairs to nucleoside-3'-monophosphates without digesting double-stranded RNA or single-stranded or double-stranded DNA that is present in the same reaction mixture. An exemplary RNase I enzyme includes *E. coli* RNase I. However, the invention is not limited to the RNase I so long as the enzyme functions for its intended purpose of specifically digesting single-stranded RNA without digesting double-stranded RNA or single-stranded or double-stranded DNA that is present in the same reaction mixture.

"Nucleoside", as used herein, refers to a compound consisting of a purine (guanine (G) or adenine (A)) or pyrimidine (thymine (T), uridine (U), or cytidine (C)) base covalently linked to a pentose sugar, whereas "nucleotide" refers to a nucleoside phosphorylated at one of the hydroxyl groups of the pentose sugar.

A "nucleic acid" or a "polynucleotide", as used herein, is a covalently linked sequence of nucleotides in which the 3' position of the sugar moiety of one nucleotide is joined by a phosphodiester group to the 5' position of the sugar moiety of the next nucleotide, and in which the nucleotide residues (bases) are linked in specific sequence; i.e., a linear order of nucleotides. An "oligonucleotide", as used herein, is a short polynucleotide or a portion of a polynucleotide. An oligonucleotide typically contains a sequence of about two to about one hundred bases. The word "oligo" is sometimes used in place of the word "oligonucleotide". In some embodiments, the oligonucleotide is an acceptor oligonucleotide (also referred to as an "acceptor oligo" or "oligonucleotide acceptor" or "oligo acceptor" or "acceptor" or "acceptor molecule" or the like). An acceptor oligonucleotide has an hydroxyl group on its 3' end, which enables it to be ligated to an RNA molecule that has a 5' monophosphate (a "donor"). In some embodiments, the oligonucleotide consists of or comprises 2'-deoxyribonucleotides (DNA). In some embodiments, the oligonucleotide consists of or comprises ribonucleotides (RNA). In some preferred embodiments wherein the oligonucleotide consists of ribonucleotides (RNA), said oligonucleotide is an "RNA acceptor oligonucleotide" or an "RNA acceptor oligo" or an "RNA acceptor" or an "RNA oligonucleotide acceptor" (or the like), meaning that it has an hydroxyl group on its 3'-end and is capable of being ligated to an RNA molecule that has a monophosphate group on it 5' end (i.e., an "RNA donor" or an "RNA donor molecule" or the like) by an RNA ligase (e.g., T4 RNA ligase, EPICENTRE, or bacteriophage TS2126 RNA ligase).

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

Nucleic acid molecules are said to have "5' ends" and "3' ends" because, except with respect to a cap (as described elsewhere herein), mononucleotides are joined in one direction via a phosphodiester linkage to make oligonucleotides, in a manner such that a phosphate on the 5'-carbon of one mononucleotide sugar moiety is joined to an oxygen on the 3'-carbon of the sugar moiety of its neighboring mononucleotide. Therefore, an end of an oligonucleotide referred to as the "5' end" if its 5' phosphate is not linked to the oxygen of the 3'-carbon of a mononucleotide sugar moiety and as the "3' end" if its 3' oxygen is not linked to a 5' phosphate of the sugar moiety of a subsequent mononucleotide.

As used herein, the terms "5'-of" and "3'-of" refer to the position or orientation of a particular chemical group, nucleotide, or sequence of nucleotides relative to another chemical group, nucleotide, or sequence of nucleotides within a single strand of a nucleic acid. For example, the hydroxyl group at the 3' position of the 3' nucleotide at the 3' end of an RNA acceptor oligonucleotide, to which the 5' end of an RNA donor molecule can be ligated using an RNA ligase, is 3'-of any other group or nucleotide within the RNA acceptor oligonucleotide. All other chemical groups, nucleotides, or sequence of nucleotides are 5'-of the 3' end of the RNA acceptor oligonucleotide. For example, in some embodiments, an RNA polymerase promoter sequence can be 5'-of that nucleotide at the 3' end of the RNA acceptor oligonucleotide. Those with knowledge in the art will understand these terms in the context of nucleic acid chemistry and structure, particularly related to the 3'- and 5'-positions of sugar moieties of canonical nucleic acid nucleotides. If a first nucleic acid sequence is 3'-of a second sequence on one strand, the complement of the first sequence will be 5'-of the complement of the second sequence on the complementary strand.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue.

An "RNA triphosphatase" means an enzyme or a subunit of an enzyme of a capping enzyme system that adds a cap nucleotide (e.g., m$^7$G) to the 5' end of eukaryotic mRNA. RNA triphosphatase catalyzes cleavage of the 5' triphosphate of a primary mRNA transcript to a 5' diphosphate. In some capping enzyme systems, the RNA triphosphatase is one activity of a protein that also has guanyltransferase activity (e.g., as for the vaccinia capping enzyme), whereas in other capping enzyme systems, the RNA triphosphatase and guanyltransferase activities are in separate proteins (e.g., *Saccharomyces cerevisiae*). Any RNA triphosphatase that has activity in cleaving the 5' triphosphate of a primary mRNA transcript to a 5' diphosphate can be used in a method of the present invention.

The terms "sample" and "biological sample" are used in their broadest sense and encompass samples or specimens obtained from any source including biological and environmental sources. As used herein, the term "sample" when used to refer to biological samples obtained from organisms, includes fluids, solids, tissues, and gases. In preferred embodiments of this invention, biological samples include bodily fluids, isolated cells, fixed cells, cell lysates and the like. For example, in some embodiments, the sample is a formalin-fixed paraffin-embedded (FFPE) tissue section, and the RNA contained in the sample comprises degraded RNA molecules, including degraded capped RNA, degraded RNA that has a 5' polyphosphate group, degraded RNA that has a 5' monophosphate group, and/or degraded RNA that has a 5' hydroxyl group. Thus, in some embodiments of any of the methods for 5' ligation tagging one or more RNA molecules in a sample, the sample contains degraded RNA, and the method is used for 5' ligation tagging one or more of the respective degraded RNA molecules (e.g., degraded capped RNA or degraded 5'-triphosphorylated RNA) in the sample. In some of these embodiments, the one or more RNA molecules that are obtained, isolated, purified, or analyzed comprise only or predominantly the 5' end portions of RNA molecules derived from the naturally occurring undegraded RNA molecules (e.g., only the 5' end portions of capped RNA molecules or of 5'-triphosphorylated RNA molecules). However, these examples are not to be construed as limiting the types of samples that find use with the present invention.

A "tag" means DNA that exhibits a sequence, called the "tag sequence," that permits identification, recognition, and/or molecular or biochemical manipulation of the DNA to which the tag is joined or attached (e.g., by providing a site for annealing a primer (i.e., a "priming site") for extension by a DNA polymerase, e.g., for a DNA sequencing or nucleic acid amplification reaction; or e.g., by providing sites for annealing of oligonucleotides for a ligation reaction (i.e., a "ligation template" for ligation using a template-dependent DNA ligase, e.g., for a sequencing-by-ligation reaction); or e.g., by providing a site for annealing of oligodeoxyribonucleotides, e.g., for sequencing by hybridization, such as described by Drmanac et al in U.S. Patent Application Nos. 20090011943; 20090005252; 20080318796; 20080234136; 20080213771; 20070099208; and 20070072208). The process of joining the tag to the DNA molecule is sometimes referred to herein as "tagging" and the DNA that undergoes tagging is referred to as "tagged" (e.g., "tagged DNA"). The tag can have one or more "tag portions" or "tag domains," which mean herein a portion or domain of the tag that exhibits a sequence for a desired intended purpose or application. The names and descriptions of different tag domains are for convenience, such as to make it easier to understand and discuss the intended purposes and applications of the different portions or domains of the tag in different embodiments. However, these names and descriptions are not intended to limit the use or applications of the tag or of any of its tag domains in any way. Thus, any particular tag or tag domain can be used for any purpose in addition to, or in place of the intended or primary purpose or application. For example, a "capture tag domain" or a "capture tag" means a tag domain that exhibits a sequence for the purpose of facilitating capture of the ssDNA fragment to which the tag domain is joined (e.g., to provide an annealing site or an affinity tag for capture of the tagged RNA or DNA on a bead or other surface, e.g., wherein the annealing site of the tag domain sequence permits capture by annealing to a specific sequence which is on a surface, such as a probe on a bead or on a microchip or microarray or on a sequencing bead). In some embodiments of the method, after the tagged RNA or DNA is captured by annealing to a complementary probe on a surface, the capture tag domain provides a site for priming DNA synthesis using said tagged RNA or DNA (or the complement of said tagged RNA or DNA) as templates. In some other embodiments, the capture tag domain is joined to a chemical group or moiety that comprises or consists of an affinity binding molecule (e.g., wherein the 5'-portion of the tagged RNA or DNA is joined to a first affinity binding molecule, such as biotin, streptavidin, an antigen, or an antibody that binds the antigen, that permits capture of the tagged RNA or DNA on a surface to which a second affinity binding molecule is attached that forms a specific binding pair with the first affinity binding molecule). A "sequencing tag domain" or a "sequencing tag" means a tag domain that exhibits a sequence for the purposes of facilitating sequencing of the RNA or DNA to which the tag is joined (e.g., to provide a priming site for sequencing by synthesis, or to provide annealing sites for sequencing by ligation, or to provide annealing sites for sequencing by hybridization). For example, in some embodiments, the sequencing tag domain provides a site for priming DNA synthesis of a tagged DNA or the complement of said tagged DNA. A "detection tag domain" or a "detection tag" means a tag domain that exhibits a sequence or a detectable chemical or biochemical moiety for the purpose of facilitating detection of the tagged RNA or DNA generated using a method of the invention (e.g., wherein the sequence or chemical moiety comprises or is joined to a detectable molecule; such as a detectable molecule selected from among: a visible, fluorescent, chemiluminescent, or other detectable dye; an enzyme that is detectable in the presence of a substrate, e.g., an alkaline phosphatase with NBT plus BCIP or a peroxidase with a suitable substrate); a detectable protein, e.g., a green fluorescent protein; and an affinity-binding molecule that is bound to a detectable moiety or that can form an affinity binding pair or a specific binding pair with another detectable affinity-binding molecule; or any of the many other detectable molecules or systems known in the art). An "address tag domain" or an "address tag" means a tag domain that exhibits a sequence that permits identification of a specific sample (e.g., wherein the tagged RNA or DNA has a different address tag domain that exhibits a different sequence for each sample). A "restriction site domain" means a tag domain that exhibits a sequence for the purpose of facilitating cleavage using a restriction endonuclease. For example, in some embodiments, the restriction site domain is used to generate di-tagged RNA or DNA. In some embodiments, the restriction site domain is used to generate a compatible double-stranded 5'-end in the tag domain so that this end can be ligated to another DNA molecule using a template-dependent DNA ligase. In some preferred embodiments, the restriction site domain in the tag exhibits the sequence of a restriction site that is present only rarely, if at all, in the target DNA (e.g., a restriction site for a rare-cutting restriction endonuclease such as NotI or AscI). In some preferred embodiments, the restriction site in the restriction site domain is for a type II restriction endonuclease, such as FokI restriction endonuclease. One tag domain can comprise or provide the functions or purposes or applications of two or more other tag domains (e.g., a sequencing tag domain can comprise both a capture tag domain and an address tag domain or a detection tag domain). Still further, the tag need not be described in terms of one or more different domains in order to be used for any particular purpose or application or function.

"Transcription" means the formation or synthesis of an RNA molecule by an RNA polymerase using a DNA molecule as a template. The invention is not limited with respect to the RNA polymerase that is used for transcription. For example, a T7-type RNA polymerase can be used.

A "T7-type RNA polymerase" as defined herein is a wild-type or mutant form of an RNA polymerase derived from a T7-type bacteriophage, including both phage-encoded enzymes and enzymes obtained by cloning the RNA polymerase gene in a DNA vector and expressing it in a bacterial or other cell. This is based on the fact that the genetic organization of all T7-type bacteriophage that have been examined has been found to be essentially the same as that of T7. Examples of T7-type bacteriophages according to the invention include *Escherichia coli* phages T3, phi I, phi II, W31, H, Y, A1, 122, cro, C21, C22, and C23; *Pseudomonas putida* phage gh-1; *Salmonella typhimurium* phage SP6; *Serratia marcescens* phages IV; *Citrobacter* phage ViIII; and Klebsiella phage No. 11 (Hausmann, Current Topics in Microbiology and Immunology 75: 77-109, 1976; Korsten et al., J. Gen. Virol. 43: 57-73, 1975; Dunn, et al., Nature New Biology 230: 94-96, 1971; Towle, et al., J. Biol. Chem. 250: 1723-1733, 1975; Butler and Chamberlin, J. Biol. Chem. 257:5772-5778, 1982). Mutant RNAPs (Sousa et al., U.S. Pat. No. 5,849,546; Padilla, R and Sousa, R, Nucleic Acids Res., 15: e138, 2002; Sousa, R and Mukherjee, S, Prog Nucleic Acid Res Mol. Biol., 73: 1-41, 2003), such as T7 RNAP Y639F mutant enzyme, T3 RNAP Y640F mutant enzyme, SP6 RNAP Y631F mutant enzyme, T7 RNAP having altered amino acids at both positions 639 and 784, T3 RNAP having altered amino acids at both positions 640 and 785, or SP6 RNAP having altered amino acids at both positions 631 and 779 can also be used in some embodiments of methods or assays of the invention. In particular, such mutant enzymes can corporate dNTPs and 2'-F-dNTPs, in addition to ddNTPs and certain other substrates, which are advantageous for synthesis of RNA molecules with specific properties and uses. In some embodiments, phage N4 mini-vRNAP, which is a transcriptionally active 1,106-amino acid domain of the N4 vRNAP that corresponds to amino acids 998-2103 of N4 vRNAP and that has certain domains in common with T7 RNAP (Kazmierczak, K. M., et al., EMBO J. 21: 5815-5823, 2002; U.S. Pat. No. 7,452,705) is the T7-type RNAP. Alternatively, in some embodiments, N4 mini-vRNAP Y678F mutant enzyme (U.S. Pat. No. 7,452,705), which can incorporate non-canonical nucleotides such as 2'-F-dNTPs, is the T7-type RNAP. In order to carry out transcription, a RNA polymerase recognizes and binds to a DNA sequence of approximately 25 nucleotides in length called an "RNA polymerase promoter," a "transcription promoter" or simply a "promoter," and initiates transcription therefrom. In most cases, the promoter sequence is double-stranded. As used herein, the strand of a double-stranded promoter that is covalently joined to the template strand for synthesis of RNA is defined as the "sense strand" or "sense promoter sequence" and its complement is defined as the "anti-sense strand" or the "anti-sense promoter sequence."

As used herein, the terms "buffer" or "buffering agents" refer to materials that when added to a solution, cause the solution to resist changes in pH. As used herein, the term "reaction buffer" refers to a buffering solution in which an enzymatic reaction is performed. As used herein, the term "storage buffer" refers to a buffering solution in which an enzyme is stored.

As used herein, the terms "chelator" or "chelating agent" refer to any materials having more than one atom with a lone pair of electrons that are available to bond to a metal cation. As used herein, the term "divalent salt" or "divalent metal cation" refers to any salt in which a metal (e.g., Mg, Mn, Ca, or Sr) has a net 2+ charge in solution.

As used herein, the terms "complementary" or "complementarity" are used in reference to a sequence of nucleotides related by the base-pairing rules. For example, the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon hybridization of nucleic acids.

The term "homology" refers to a degree of complementarity of one nucleic acid sequence with another nucleic acid sequence. There may be partial homology or complete homology (i.e., complementarity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks complementarity or that has only a low degree of complementarity (e.g., less than about 30% complementarity). In the case in which specific binding is low or non-existent, the probe will not hybridize to a nucleic acid target.

When used in reference to a double-stranded nucleic acid sequence such as a cDNA or a genomic clone, the term "substantially homologous" refers to any probe which can hybridize to either or both strands of the double-stranded nucleic acid sequence under conditions of low stringency as described herein.

As used herein, the terms "hybridization" or "annealing" are used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol or betaine), the molarity of the hybridizing strands and the G:C content of the nucleic acid strands.

The terms "isolated" or "purified" when used in relation to a nucleic acid, as in "isolated polynucleotide" or "isolated oligonucleotide" or "purified RNA" or a "capped RNA that is purified" refers to a nucleic acid that is identified and separated from at least one contaminant with which it is ordinarily associated in its source. Thus, an isolated or purified nucleic acid (e.g., DNA and RNA) is present in a form or setting that is different from that in which it is found in nature or that is different from that which existed prior to subjecting it to a treatment or purification method. For example, a given DNA sequence (e.g., a gene) is found on the host cell chromosome together with other genes, and a specific RNA (e.g., a specific mRNA encoding a specific protein), is found in the cell as a mixture with numerous other mRNAs that encode a multitude of proteins. The isolated or purified polynucleotide or nucleic acid or oligonucleotide or DNA or RNA may be present in single-stranded or double-stranded form. When an isolated or purified polynucleotide or nucleic acid is to be utilized to express a protein, the polynucleotide contains at a minimum, the sense or coding strand (i.e., the polynucleotide may be single-stranded), but may contain both the sense and anti-sense strands (i.e., the polynucleotide may be double-stranded).

EXAMPLES

The following examples serve to illustrate certain preferred embodiments and aspects of the present invention and are not to be construed as limiting the scope thereof.

Discovery and Purification of RNA Polyphosphatase

The discovery of an RNA polyphosphatase (RPP) occurred when we renatured *Escherichia coli* proteins in situ in SDS-PAGE gels. The SDS-PAGE (15%) running gel was prepared by polymerization of the polyacrylamide in the presence of gamma $^{32}$P-end-labeled RNA (synthesized by in vitro transcription of a linear DNA template using T7 RNA polymerase, T7 reaction buffer, gamma-$^{32}$P-labelled GTP, and unlabelled ATP, CTP and UTP). After electrophoresis, the SDS-PAGE running buffer was exchanged by incubating the gel in non-SDS-containing buffer to remove the SDS and permit protein renaturation in situ. The gel was incubated in buffer overnight and the gel was stained with SYBR Gold (Invitrogen, Carlsbad, Calif.). An unstained band was evident which migrated with a molecular weight of approximately 30,000. However, when the gel was fixed in 7.5% acetic acid and then dried and subjected to autoradiography, two bands devoid of radioactivity were observed which migrated with molecular weights of approximately 30,000 (30 kDa) and approximately 19,000 (19 kDa). SYBR Gold staining indicated the presence of RNA in the 19-kDa band, consistent with dephosphorylation, but not with degradation, of $^{32}$P-end-labeled RNA by the 19-kDa protein. The lack of SYBR Gold staining in the 30-kDa band was consistent with the protein in the band being an RNase, which was likely RNase I.

In order to simplify the assay for enzyme activity and facilitate purification of the enzyme, we searched for alternative enzyme substrates. We found that the fluorogenic phosphatase substrate 6,8-difluoro-4-methylumbelliferyl phosphate (DiFMUP) was a substrate for the 19-kDa protein. Upon hydrolysis, this substrate is converted to the fluorescent product 6,8-difluoro-7-hydroxy-4-methylcoumarin (DiFMU), which has an absorption peak at 358 nm and an emission peak at 455 nm. Surprisingly, the RPP enzyme exhibited greater than 50-fold more activity using DiFMUP as a substrate than using 4-methylumbelliferyl phosphate (4MUP) as a substrate. Thus, using a standard ultraviolet transilluminator, DiFMUP was used to detect a single 19-kDa fluorescent band in total extracts of Escherichia coli after protein renaturation in situ on a polyacrylamide gel. The band also was stained by Coomassie blue protein dye. Using the simpler DiFMUP assay, we were able to scale up purification of the RNA polyphosphatase protein and further characterize its physical and enzymatic properties. For example, in some embodiments, the RNA polyphosphatase activity is purified using one or more of the following methods: polyethyleneimine fractionation; ammonium sulfate fractionation; Bio-Rex 70 cation exchange column chromatography (e.g., Bio-Rex 70 chromatography); gel filtration column chromatography (e.g., Sephacryl S100); and anion exchange column chromatography (e.g., SP-Sepharose). The RNA polyphosphatase activity chromatographed as a single peak in both ion exchange and gel filtration columns, suggesting that the 19-kDa protein was the sole enzyme showing this activity.

Identification of the Gene Coding for RNA Polyphosphatase

To identify the protein and determine the genetic locus coding for the RNA polyphosphatase enzyme, the RNA polyphosphatase was digested in-gel with trypsin, and the resulting tryptic digests were analyzed using matrix-assisted laser desorption ionization time of flight mass spectrometry (MALDI-TOF MS). When compared with protein sequences in NCBI database using the MASCOT search engine, the tryptic peptide sequences derived from RNA polyphosphatase matched with a protein from Escherichia coli 53638. In fact the top twelve matches (protein scores ranging from 439 to 229, $p<0.05$) were to the same protein in the database from different strains of Escherichia coli. An alignment of the twelve proteins from different strains of Escherichia coli showed that they were essentially identical. In Escherichia coli K12 (MG1655), this protein (locus tag b2252) has been annotated as an aluminum-inducible protein of unknown function. The corresponding aluminum-inducible (ais) gene maps to 50.04 min and codes for approximately a 200-amino-acid protein. It is classified as a non-essential gene whose mRNA levels were induced 16 fold after addition of 0.2 mM $ZnSO_4$ to a culture grown in a defined medium lacking inorganic phosphate. Information on the protein product of this gene was not available since it has not been detected before. Without being bound by theory, the search for conserved domains in the ORF indicates that the protein could be a member of the phosphoglycerate mutase-like superfamily. Catalytic activity of enzymes in this family typically involves phosphorylation of histidine.

Cloning and Over-expression of the ais Gene

We amplified the ais gene (b2252 locus) by polymerase chain reaction using genomic DNA isolated from Escherichia coli K12 (MG1655) using specific oligonucleotide primers that contain recognition sites for NdeI and BamHI restriction enzymes. The forward primer containing the NdeI recognition sequence was engineered to change the first codon GTG to ATG. The amplified product was cloned into the corresponding sites of an inducible T7-based pET plasmid expression vector, and following transformation of competent Escherichia coli EC100 cells and selection of recombinants, the sequence of the insert DNA was verified to be that of ais gene. RNA polyphosphatase activity of the protein from the recombinant clone was detected by fluorescence using the in situ gel assay as before and over-expression of the protein upon induction was monitored by Coomassie blue staining Purified native RNA polyphosphatase was used as a control in these experiments. Less total protein from the recombinant clone was used for the gel assay in order to minimize detection of the endogenous RNA polyphosphatase present in the uninduced cells.

Two fluorescent and Coomassie blue-staining bands were seen in protein extracts prepared from induced recombinant cells. One of these bands from the induced recombinant cells was a soluble protein with RNA polyphosphatase activity that was identical in size and properties to the 19-kDa native RNA polyphosphatase enzyme. In addition, a second 24-kDa protein with RNA polyphosphatase activity, which was present predominantly in inclusion bodies, was also over-expressed in the induced recombinant cells. The amino terminus of the purified native enzyme and recombinant 24-kDa and 19-kDa RNA polyphosphatase enzymes were determined by Edman degradation. The sequences of the amino terminus of the native and the over-expressed recombinant 19-kDa protein, S—N-G-L-P, were identical. The amino terminus of the 24-kDa recombinant protein, M-L-A-F, corresponds to the amino terminus of cloned ais gene. The amino terminal sequence, S—N-G-L-P, of the native enzyme suggested that perhaps the protein is processed by a signal peptidase and the mature enzyme is present in the periplasmic space. To determine the sub-cellular distribution of the native enzyme, Escherichia coli B cells were converted to spheroplasts and the RNA polyphosphatase activity that was released into the supernatant (periplasmic fraction) and that was retained by the spheroplast (cytoplasmic fraction) was measured by fluorescence in situ gel assay. RNA polyphosphatase was detected in the periplasmic fraction and this activity co-migrated with the 19-kDa size of the purified native enzyme. The cytoplasmic fraction also contained RNA polyphosphatase activity that migrated as a 19-kDa protein but no 24-kDa RNA polyphosphatase was detected. Without being bound by theory, the data suggests that the recombinant 19-kDa RNA polyphosphatase is a periplasmic protein derived from the 24-kDa protein by processing of the amino terminal end. The presence of a 19-kDa RNA polyphosphatase activity observed in the cytoplasmic fraction of non-recombinant cells could have been due to incomplete conversion of cells into spheroplasts and the presence of the 24-kDa active protein in recombinant cells was probably due to unprocessed protein that was present in inclusion bodies within the recombinant cells. It is interesting to note that the ais gene was categorized as a secreted protein by Zalucki, Y M, et al. (Nucleic Acids Res. 35: 5748-5754, 2007) but the predicted cleavage site was different from the identified amino terminus.

Catalytic Properties of Purified RNA Polyphosphatase

The purified RNA polyphosphatase enzyme is active over a wide range of pH (e.g., it has optimal activity in the range between pH 5.0 and pH 8.0). Surprisingly, and in contrast to some other phosphate-removing enzymes, it does not require a divalent cation like $Mg^{2+}$ and is active in the presence of EDTA. In fact, the enzyme was inhibited in the presence of 1 mM $Mg^{2+}$ cations.

In addition to removing the beta and gamma phosphates from nucleic acids, such as primary RNA or from 5'-diphosphorylated RNA (e.g., from a capping enzyme RNA triphosphatase reaction), the purified ~19-kDa single-subunit RNA polyphosphatase can remove phosphate groups from a variety of other substrates, including nucleoside-5'-diphosphates and triphosphates (e.g., NTPs, NDPs, dNTPs, dNDPs). The product of hydrolysis is a nucleoside 5' monophosphate and inorganic orthophosphate. Nucleoside-5'-monophosphates are not substrates. ADP was hydrolyzed at 50% efficiency compared to ATP. The enzyme hydrolyzes nucleoside triphosphates in a stepwise manner, releasing inorganic orthophosphate instead of pyrophosphate. A time course analysis of products of ATP hydrolysis by thin layer chromatography showed accumulation of ADP first followed by appearance of AMP. Interestingly, while polyphosphate was as good a substrate for RNA polyphosphatase as ATP, inorganic pyrophosphate does not appear to be a substrate. The symmetrical dinucleoside triphosphate G[5']ppp[5']G and its methylated derivative m7G[5']ppp[5']G were hydrolyzed very poorly, if at all, suggesting that the enzyme is an exopolyphosphatase. Also, while DiFMUP, the substrate used in the initial screening and identification of the enzyme was a good substrate, 4-methyl-umbelliferyl phosphate and p-nitrophenyl phosphate (PNPP) were poor substrates for the enzyme, and bis (p-nitrophenyl) phosphate was hydrolyzed very poorly. Without being bound by theory, it is postulated that the fluorines at positions 6 and 8 probably play a role in making DiFMUP a substrate for the enzyme even though it has a single phosphate. 5-Bromo-4-chloro-3-indolyl phosphate and the phosphoamino acid phosphoserine were essentially not recognized at all as substrates.

We believe that RNA polyphosphatases that can cleave RNA that has a triphosphate or diphosphate group on its 5' end to a monophosphate, but that cannot cleave capped RNA to a monophosphate have not previously been described in the art. This activity is useful for a variety of methods described herein. However, without being bound by theory, we do not believe that the bacteria from which RNA polyphosphatase is derived use the enzyme for a similar function in nature. Rather, we believe that the finding that RNA polyphosphatase is a periplasmic enzyme in prokaryotes indicates that its natural function may be for scavenging for essential nutrients (e.g., phosphate) in its environment. Thus, the methods described herein may be artificial, even if convenient for our purposes. Nevertheless, since these and some other phosphatases are multifunctional and are active on a broad range of phosphorylated compounds (e.g., nucleotides, sugar phosphates, phospholipids, and polyphosphates), the roles played by RNA polyphosphatases in nature remains unknown.

Isolation of Total RNA from a Sample for Use in 5' Ligation Tagging

In some embodiments, total RNA was isolated from a sample (e.g., using the MASTERPURE™ RNA purification kit, EPICENTRE, Madison, Wis., according to protocols of the manufacturer, or another suitable method in the art). In some embodiments, the total RNA was from a culture of a bacterium. In some embodiments, the total RNA was isolated from cultured HeLa human cells using the MASTERPURE™ RNA purification kit. In some embodiments, the total RNA is from an environmental source (e.g., as described by Frias-Lopez, J et al., Proc. Natl. Acad. Sci. USA 105: 3805-3810, 2008). In some embodiments, the total RNA is from a legume root nodule containing a *Rhizobium* or other nitrogen-fixing symbiotic bacterium. In some embodiments, the total RNA is from an animal or human clinical sample of a tissue infected by a bacterial or mycoplasmal pathogen. In some embodiments, the total RNA is from a human or animal sample (e.g., from a cancer specimen or from normal cell of the same type).

Treatment of RNA with RNA 5' Polyphosphatase to Convert RNA that has a 5' Polyphosphate Group to RNA that has a 5' Monophosphate Group In some embodiments, one microgram of sample RNA (either untreated or after pre-treatment with another enzyme) is incubated in a 20-microliter reaction mixture containing *E. coli* RNA 5' polyphosphatase I (RPP I, EPICENTRE) in 1× RNA 5' polyphosphatase reaction buffer consisting of 50 mM HEPES/KOH (pH 7.5), 0.1 M NaCl, 1 mM EDTA, 0.1% BME and 0.01% TRITON X100 for 30 min at 37° C.; 20 Units of the RPP I was used in a standard 20-microliter reaction, but different amounts of enzyme were used in some experiments. In some embodiments, the RPP I-treated, and/or TERMINATOR-treated sample RNA was purified using a Zymo Research RNA cleanup column (Orange, Calif.) and analyzed by agarose gel electrophoresis. The RPP I enzyme converted the 1.4-Kb 5'-triphosphorylated control transcript from an AMPLISCRIBE™ T7 Kit (EPICENTRE) to a TERMINATOR-sensitive 5'-monophosphorylated form, as shown by agarose gel analysis. In control experiments under identical conditions, the TERMINATOR enzyme did not digest an RPP I-treated 5'-capped 915-base transcript, which shows the specificity of the RPP I enzyme in converting a 5'-polyphosphorylated RNA, but not 5'-capped RNA, to a 5'-monophosphorylated form.

In some embodiments, the RPP I-treated RNA was cleaned up by Phenol:Chloroform and Chloroform extraction and ethanol precipitation. In some other embodiments wherein the sample was treated with RMP1 (see Example below) prior to treatment with RPP I, the RMP1 enzyme activity was inhibited by addition of the EDTA, and the entire reaction mix from the RMP1-treated RNA was added to 10 microliters of a 2× concentration of the RPP I reaction mix.

In some embodiments, the reaction mix from treatment of an RNA with an enzyme is extracted once with Phenol:Chloroform (1:1 mix), once with Chloroform and the RNA is recovered from the aqueous phase by ethanol precipitation and dissolved in 10.0 microliters of 10 mM Tris-HCl (pH 8.0), 1 mM EDTA.

In some embodiments wherein one desires to polyadenylate the RNA, the entire volume of the reaction mixture from the RPP I reaction is used for the poly(A) tailing reaction.

Treatment of RNA with RNA 5' Monophosphatase to Convert RNA that has a 5' Monophosphate Group to RNA that has a 5' Hydroxyl Group In some embodiments wherein a sample RNA is used in a method of the present invention for 5'-ligation tagging, up to about one microgram of the sample RNA is incubated with about one to about 100 Molecular Biology Units (MBU) (or another empirically determined optimal quantity) of RNA 5' Monophosphatase 1 (RMP1, EPICENTRE) in a reaction buffer consisting of either (i) 33 mM Tris-acetate, pH 7.5, 66 mM potassium acetate, 10 mM magnesium acetate, 5 mM calcium chloride, and 0.5 mM DTT, or (ii) 50 mM Tris-HCl, pH 8.0, 2 mM magnesium chloride, 100 mM sodium chloride, and 5 mM calcium chloride for 60 minutes at 30° C. In preferred embodiments, the rRNA (e.g., 18S and 26S or 28S eukaryotic rRNA or 16S and 23S prokaryotic rRNA) is removed from the sample prior to its use in the method of the present invention. This is because the applicants have found that other methods (e.g., RIBOMINUS™ kits) are more efficient that RMP1 for removing the high levels of rRNA (e.g., up to about 98% of total RNA) present in most samples. It was found that, if the rRNA is removed from the sample, it is easier to use the methods of the present invention for 5'-ligation tagging and downstream analyses of other less abundant 5'-monophosphorylated RNA molecules (e.g., miRNA).

Nevertheless, the applicants performed a number of experiments to study the activity and specificity of RMP1 using samples comprising different classes of RNA molecules. For example, in some experiments sample RNA consisting of either (i) total RNA from HeLa cells, or (ii) Human Total Reference RNA (STRATAGENE), or (iii) the 1.4-Kb 5'-triphosphorylated control transcript from an AMPLIS- CRIBE™ T7 High Yield Transcription Kit (EPICENTRE) was incubated with about 10-60 MBU of RMP1, (EPICENTRE) in a reaction buffer as described above. In some embodiments, the RMP1-treated sample RNA was then treated with TERMINATOR™ 5'-Phosphate-dependent Exonuclease (EPICENTRE, Madison, Wis.) according to the directions of the manufacturer. Control reactions were incubated in the same conditions without the RMP1 enzyme or without the TERMINATOR™ enzyme, respectively. In some other embodiments, the RMP1- and TERMINATOR-treated sample RNA was then purified using a Zymo Research RNA cleanup column (Orange, Calif.) and analyzed by agarose gel electrophoresis. It was observed that RMP1 at about 10 MBU or more per 20-microliter reaction decreased digestion of the 18S or 28S HeLa rRNA by the TERMINATOR™ enzyme, and 20 MBU or more of RMP1 per 20-microliter reaction significantly (but not completely) decreased digestion of the 18S or 28S HeLa rRNA by the TERMINATOR™ enzyme. In a similar reaction using STRATAGENE's Human Reference RNA, about 10 MBU or more per 20-microliter reaction detectably decreased digestion of the human 18S or 28S rRNA by the TERMINATOR™ enzyme; about 20 MBU of RMP1 per 20-microliter reaction significantly decreased digestion of the human 18S or 28S rRNA by the TERMINATOR™ enzyme; and about 40 MBU of RMP1 per 20-microliter reaction protected the human 18S or 28S rRNA from digestion by the TERMINATOR™ enzyme about two-fold better than the 20 MBU of RMP1 per 20-microliter reaction. It appears that the RMP1 dephosphorylated the 5'-monophosphorylated 18 or 28S rRNA, protecting it from digestion by TERMINATOR 5'-Phosphate-dependent Exonuclease. Prior treatment of the 1.4-Kb 5'-triphosphorylated control transcript from an AMPLISCRIBE™ T7 Kit with about 10 MBU of RMP1 did not make the 1.4-Kb transcript susceptible to digestion by the TERMINATOR enzyme, even though treatment of the RMP1-treated 1.4-Kb transcript with RPPI (see above) after treatment with the RMP1 did result in digestion of the 1.4-Kb transcript by the TERMINATOR enzyme; thus, under the conditions tested, RMP1 did not convert the 1.4-Kb 5'-triphosphorylated transcript to a TERMINATOR-sensitive 5'-monophosphorylated form or to TERMINATOR-resistant 5'-hydroxylated form, indicating the specificities of the respective RMP1 and RPP I enzymes. In other reactions, a 5'-capped 915-base RNA transcript was not digested by the TERMINATOR enzyme, whether the 5'-capped RNA transcript was untreated or was first treated with the RMP1 enzyme; the 5'-capped RNA transcript was prepared by in vitro transcription using an AMPLISCRIBE™ T7-Flash Transcription Kit (EPICENTRE), followed by capping using SCRIPTGUARD™ Capping Enzyme (EPICENTRE), both according to the directions of the manufacturer. (In some embodiments, the reaction mix is extracted once with Phenol:Chloroform (1:1 mix), once with Chloroform and the RNA is recovered from the aqueous phase by ethanol precipitation and dissolved in 10 microliters of 10 mM Tris-HCl, pH 8.0, 1 mM EDTA after the RMP1 and/or TERMINATOR treatment. In some embodiments, the reaction mix is not extracted, but 10-20 mM EDTA is added prior to proceeding to the next step (e.g., prior to a TERMINATOR or RNA 5' Polyphosphatase reaction)).

Additional experiments were performed to analyze the specificity of RMP1, RPP I and other enzymes for 5'-monophosphorylated RNA compared to 5'-triphosphorylated RNA. For these experiments, a gamma-$^{32}$P-labeled 51-mer 5'-triphosphorylated RNA was prepared by in vitro transcription using an AMPLISCRIBE™ T7 transcription kit (EPICENTRE) and gamma-$^{32}$P-GTP; and an alpha-$^{32}$P-labeled 51-mer 5'-monophosphorylated RNA of the same sequence was prepared by first treating the unlabeled 51-mer RNA made with the AMPLISCRIBE™ T7 transcription kit with APex™ thermolabile alkaline phosphatase (EPICENTRE) to prepare the 5'-hydroxylated 51-mer RNA and then labeling its 5'-end using gamma-$^{32}$P-labeled ATP and T4 polynucleotide kinase (EPICENTRE). The gamma- and alpha-$^{32}$P-labeled 51-mer RNAs were each incubated with RMP1 (EPICENTRE), RPP I (EPICENTRE), Apex™ thermolabile alkaline phosphatase, SCRIPTCAP™ capping enzyme (EPICENTRE), tobacco acid pyrophosphatase (TAP, EPICENTRE), and TERMINATOR™ 5'-phosphatase dependent exonuclease (EPICENTRE), respectively. RMP1 (2 MBU @~1 MBU per pmol) dephosphorylated ~0.13 pmol of the alpha-$^{32}$P-monophosphate-labeled 51-mer RNA to a 5'-hydroxylated form, to the same extent as did APex™ alkaline phosphatase; also, the alpha-$^{32}$P-monophosphate-labeled 51-mer RNA was digested and no $^{32}$P labeled RNA was detected following incubation with TERMINATOR exonuclease, but the $^{32}$P label was not removed from the alpha-$^{32}$P-monophosphate-labeled 51-mer RNA by RPP I, TAP, or SCRIPTCAP™ capping enzyme. Neither RMP1 (2 MBU @~1 MBU per pmol), nor TERMINATOR exonuclease removed the $^{32}$P label from the gamma-$^{32}$P-labeled 5'-triphosphorylated 51-mer RNA, but the $^{32}$P label was removed from the gamma-$^{32}$P-labeled 5'-triphosphorylated 51-mer RNA by APex alkaline phosphatase, RPP I, TAP, and SCRIPTCAP™ capping enzyme, respectively.

Polyadenylation of Total RNA

The following components are added sequentially at room temperature to 20 microliters of each reaction mix from the previous step for polyA tailing of the RNA:

| Component | Volume (microliters) |
| --- | --- |
| PolyA Polymerase 10X Rxn Buffer | 4 |
| 10 mM ATP | 4 |
| Water | 10 |
| PolyA Polymerase (4 U/microliter) | 2 |

10X PolyA Polymerase Rxn Buffer: 0.5M Tris-HCl (pH 8.0), 2.5M NaCl, 10 mM DTT, and 100 mM MgCl$_2$.

The reaction mix was incubated at 37° C. for 30 min.

In some embodiments, the reaction mix is extracted once with Phenol:Chloroform (1:1 mix), once with Chloroform and the RNA is recovered from the aqueous phase by ethanol precipitation and dissolved in 10.0 microliters of 10 mM TE Solution, consisting of Tris-HCl (pH 8.0) and 1 mM EDTA.

Polyadenylation of RNA that has a 2'-O-Methylated 3'-Terminal Nucleotide

RNA molecules that have a 2'-O-methyl group (2'OMe-RNA) on their 3'-terminal nucleotides (e.g., plant miRNAs, germline-specific piwiRNAs, endogenous siRNAs) are polyadenylated poorly or not at all by either *E. coli* or *Saccharomyces* polyA polymerase.

However, the applicants found that, following ligation of one or two AMP residues to the 3'-end of a 2'OMe-RNA, used as a ligation acceptor, to adenylated-5'-AMP (A5' pp 5'A), used as a ligation donor, by T4 RNA ligase 1 or T4 RNA ligase 2 in the absence of added ATP, the 2'OMe-RNA that had the one or two AMP residues could be polyadenylated by polyA polymerase (EPICENTRE). Also, prolonged incubation (e.g., >4 hours) of a 2000-fold molar excess of A5' pp 5'A over either the 2'OMe-RNA or RNA of the same sequence that lacked the 2'OMe group, used as the ligation acceptor, resulted in addition of approximately 15-20 nucleotide polyA tail due to a multiplicity of AMP nucleotides being sequentially ligated to the 3'-ends of each respective RNA molecule. The polyadenylated 2'OMe-RNA molecules obtained from both methods were templates for cDNA synthesis by reverse transcription using a complementary oligo(dT) or oligo(dU) primer or an anchored primer comprising oligo(dT) or oligo (dU), including such primers which also exhibited a 5'-portion that had a tag (e.g., comprising or consisting of a sequencing tag domain, e.g., a Roche 454A or 454B sequencing tag domain, e.g, for generating sequencing templates for sequencing using the Roche 454 sequencing platform or other next-generation or older sequencing platforms).

The A-extended 2'OMe-RNA, and not the 22-nucleotide RNA without the additional A nucleotides at the 3'-end, was quantitatively tailed with polyA polymerase as previously described. This polyA-tailed molecule could then be 5'-ligation tagged at the 5'-end in an ATP-dependent T4 RNA ligase 1-mediated standard ligation reaction according to the protocol of the manufacturer EPICENTRE.

Thus, in some experiments, purified A5' pp 5'A (1 mM), as a ligation donor, was incubated for various times at 22° C. with 0.5 micromolar of a 2'OMe-RNA acceptor (obtained from IDT) that has been identified as an *Arabidopsis thaliana* miRNA (miR173[2'OMe]), which exhibits the following sequence:

```
                                            (SEQ ID NO: 3)
    rUrUrCrGrCrUrUrGrCrArGrArGrArGrArArArUrCrAmC
``` in a 10-microliter reaction containing 25 mM Tris-HCl (pH 8.0), 1 mM MgCl$_2$, 50 mM NaCl, 10 mM DTT, 20% DMSO, 20 units of ScriptGuard™ RNase inhibitor, 0.5 microliter of APex™ heat-labile alkaline phosphatase (which was included in order to dephosphorylate the 5'-AMP released from the ligation reaction between the A5' pp 5'A donor and the 2'OMe-RNA acceptor) and different amounts of different preparations of either T4 RNA ligase 1 or T4 RNA ligase 2 (all enzymes were from EPICENTRE). A 2.5-microliter aliquot from each reaction was analyzed following electrophoresis on a 16% urea-polyacrylamide gel following staining with SYBR gold.

AMP residues were ligated to the 2'OMe-RNA by both T4 RNA ligase 1 and T4 RNA ligase 2, but T4 RNA ligase 2 was more efficient in ligating the donor to the 2'OMe-RNA in these experiments, especially if the percentage of the ligase enzyme molecules that were adenylated was low. T4 RNA ligase 2 (5 micromolar) added one or more AMP residues to about 50% to about 80% of the 2'OMe-RNA molecules after one to about four hours of incubation. After 12 hours of incubation, greater than about 90% of the 2'OMe-RNA molecules had one or more AMP residues ligated to their 3' ends. Extending the incubations to greater than 12 hours and/or using higher concentrations of either of the RNA ligases (e.g., >5 to about 50 micromolar) increase the ligation efficiency.

In some experiments, the resulting 5'-ligation tagged and polyA-tailed RNA was converted to cDNA by reverse transcription using MMLV reverse transcriptase, and was amplified by PCR (e.g., by adding 10-microliter of the ligation reaction mix to provide the template for first-strand cDNA synthesis in a 40 microliter reaction containing 500 micromolar each of dATP, dCTP, dGTP, dTTP, 0.5 micromolar of an anchored oligo(dT) adapter primer:

```
                                            (SEQ ID NO: 4)
    (CTATAGGCGCGCCACCGGTGTTTTTTTTTTTTTTTTTVN),
``` and 40 units of MMLV reverse transcriptase (EPICENTRE) for 10 min at 37° C., and then inactivating the enzymes by incubating at 85° C. for 10 min and removing the RNA by digesting with one microliter of RNAse mix (EPICENTRE) at 55° C. for 5 minutes).

One microliter of a 50-fold dilution of the first-strand cDNA synthesis mix was amplified by PCR in a 100-microliter reaction mixture containing 1× MasterAmp™ PCR Pre-Mix E (EPICENTRE), 20 pmoles of forward PCR primer

```
    (AATGCGGCCGCGCCTCCCTCGCGCCATCAG (SEQ ID NO: 5)),
```

20 pmoles of reverse PCR primer

```
    (TATAGGTGCCGGCGCGCCACCGGTG (SEQ ID NO: 6)),
``` and 1 microliter of FailSafe™ PCR Enzyme mix (EPICENTRE), cycled at 94° C. for 30 seconds, 60° C. for 10 seconds, and 72° C. for 10 seconds. Five microliters of the PCR reaction were analyzed after 15 and 18 cycles on a 8% polyacrylamide gel and visualized by SYBR gold staining.

The PCR product was then digested with Not I and Asc I restriction enzymes and ligated into pCDC1-K™ cloning-ready vector (EPICENTRE), which was used to transform TransforMax™ EC100™ cells (EPICENTRE). Plasmids from 21 randomly picked transformant colonies were sequenced and confirmed to correspond to the expected miR173 sequence.

Tobacco Acid Pyrophosphatase Reaction

In some embodiments, the RPP I reaction step or both the RMP1 and the RPP I reaction steps are omitted and replaced by a tobacco acid pyrophosphatase (TAP) reaction step. For example, in some embodiments, one microgram of total RNA, which has not been treated with an alkaline phosphatase, was incubated with 10 Units of Tobacco Acid Pyrophosphatase (EPICENTRE) in 50 mM sodium acetate (pH 6.0), 1 mM EDTA, 0.1%13-mercaptoethanol and 0.01% Triton X100 for 30 min at 37° C. in a volume of 10 microliters. Control reactions were incubated in the same buffer without the TAP enzyme.

Reaction for 5' Ligation Tagging of RNA that has a 5' Monophosphate Group

Each sample containing a 5'-monophosphorylated RNA that it is desired to tag by 5'-ligation tagging was treated with RPP I or TAP (either before or after, or with or without a poly(A) tailing reaction step) is then subjected to a 5' ligation tagging reaction. The following components are added sequentially at room temperature to the reaction mix from the previous step:

| Component | Volume (microliters) |
|---|---|
| Water | 4 |
| 10X RLRT Buffer | 2 |
| 200 millimolar sodium phosphate | 1 |
| 50 micromolar RNA Acceptor | 1 |
| 2 mM rATP | 1 |
| T4 RNA Ligase (5 U/microliter) | 1 |

10X RLRT Buffer:
500 mM Tris-HCl, pH 8.3, 750 mM KCl, and 30 mM MgCl$_2$.

Example Sequence of an RNA Acceptor Oligonucleotide (SEQ ID NO: 7)
rGrArGrCrGrGrCrCrGrCrCrUrGrCrArGrGrArArA The reaction mix was incubated at 37° C. for 30 min, resulting in 5' ligation tagging of 5'-monophosphorylated RNA.

First-strand cDNA Synthesis Reaction

Following the 5' ligation tagging reaction, each 5'-ligation-tagged RNA sample is used as a template for synthesis of first-strand cDNA. If desired, the first-strand cDNA synthesis primer has a tag in its 5'-portion that is not complementary to the 3'-end of the 5'-ligation-tagged RNA used as a template for first-strand cDNA synthesis; in some embodiments the tag in the 5'-portion of the first-strand cDNA synthesis primer comprises or consists of a sequencing tag domain. First-strand cDNA synthesis is accomplished by adding the following components to the reaction mix from the previous 5' ligation tagging reaction:

| Component | Volume (microliters) |
|---|---|
| Water | 14 |
| 10X RLRT Buffer | 2 |
| 10 mM each of dATP, dCTP, dGTP and dTTP | 2 |
| First-strand cDNA Synthesis Primer (2 micromolar) | 1 |
| MMLV Reverse Transcriptase (40 U/microliter) | 1 |

Example Sequence of a First-strand cDNA Synthesis Primer (SEQ ID NO: 8)
TAGACTTAGAAATTAATACGACTCACTATAGGCGCGCCACCGGTGd
(T)$_{18}$ The reaction mix was incubated at 37° C. for 30 min, resulting in synthesis of 5' and 3'-tagged first-strand cDNA.

Removal of RNA after Synthesis of First-strand cDNA

Following the first-strand cDNA synthesis reaction, the RNA in the RNA:cDNA hybrids and the unused RNA acceptor oligo are digested with RNase I and RNase H to obtain only first-strand cDNA. This is accomplished by adding 1 microliter of RNAse mix (containing 0.5 Units RNase 1 and 0.5 Units of HYBRIDASE™ Thermostable RNase H, EPICENTRE) to the first-strand cDNA synthesis reaction mixture and then incubating at 55° C. for 5 min.

Second-strand cDNA Synthesis

The first-strand cDNA, synthesized as described above, is used as a template for synthesis of second-strand cDNA:

| Component | Volume (microliters) |
|---|---|
| Water | 27 |
| Second-strand cDNA Synthesis Primer (2 micromolar) | 1 |
| FailSafe ™ 2X PCR PreMix E (EPICENTRE) | 30 |
| FailSafe ™ PCR Enzyme | 1 |

Example Sequence of a Second-strand cDNA Synthesis Primer (SEQ ID NO: 9)
TCATACACATACGATTTAGGTGACACTATAGAGCGGCCGCCTGCAGGAA
A The reaction mix is incubated at 72° C. for 10 min, resulting in synthesis of double-stranded cDNA that has tags on both ends of each strand of cDNA.

The reaction mix is then extracted once with Phenol:Chloroform (1:1 mix), once with Chloroform, and 100 microliters of DNA Fragment 2× Precipitation Solution (EPICENTRE) is added and chilled on ice for 10 min. The DNA is recovered by centrifugation and the pellet is washed once with 70% ethanol and dissolved in 25 microliters of 10 mM Tris-HCl (pH 8.0), 1 mM EDTA.

PCR Amplification

In some other embodiments, the first-strand cDNA is amplified by PCR (e.g., for cloning) by adding the same components as described above for the Second-strand cDNA Synthesis, except that, in addition to the Second-strand cDNA Synthesis Primer (which serves as PCR Primer 1), 1 microliter of the following primer (PCR Primer 2) is also added to the PCR reaction in place of 1 microliter of water to amplify the tagged first-strand cDNA:

Example Sequence of a PCR Primer 2

(SEQ ID NO: 10)
5' TAGACTTAGAAATTAATACGACTCACTATAGGCGCGCCACCG

The PCR reaction mix is cycled at the following temperatures:

Step I: 95° C./30 sec
Step II: (94° C./30 sec, 60° C./30 sec, 72° C./4 min) for 15 cycles The reaction mix is then extracted once with Phenol:Chloroform (1:1 mix), once with Chloroform, and 100 microliters of DNA Fragment 2× Precipitation Solution (EPICENTRE) is added and chilled on ice for 10 min. The DNA is recovered by centrifugation and the pellet is washed once with 70% ethanol and dissolved in 25 microliters of 10 mM Tris-HCl (pH 8.0), 1 mM EDTA.

RNA Synthesis Reactions

In some embodiments, the double-stranded cDNA or the PCR-amplified cDNA is used as a template for in vitro transcription of RNA. For example, the Second-strand cDNA Synthesis Primer in the above example exhibits a sequence for an SP6 RNA polymerase promoter. The double-stranded cDNA that contains this promoter is a template for synthesis of sense RNA. The RNA synthesis reaction can be performed (e.g., using an AMPLISCRIBE™ SP6 transcription kit, EPICENTRE) according to the protocols provided with the kit. In other embodiments a First-strand cDNA synthesis primer that exhibits a sequence for an RNA polymerase promoter in its 5' portion can be used for the First-strand cDNA synthesis reaction. For example, the First-strand cDNA Synthesis Primer in the above example, which exhibits a sequence for a T7 RNA polymerase promoter, or the oligo(dT) T7 promoter primer provided in a TARGETAMP™ RNA amplification kit can be used to synthesize first-strand cDNA of RNA that has a poly (A) tail. Then, following synthesis of double-stranded cDNA or PCR-amplified cDNA, the promoter in the resulting double-stranded cDNA can be used as a template for synthesis of antisense RNA (e.g., using an AMPLISCRIBE™ T7 transcription kit, EPICENTRE) or the in vitro transcription reagents in the TARGETAMP™ RNA amplification kit, according to the protocols provided with each kit. In some embodiments, RNA is labeled during or after in vitro transcription and used as target for microarray analysis.

Analysis of the 5' Ends of 5'-Ligation-Tagged RNA

In some other embodiments, the 3' end of the tagged first-strand cDNA (corresponding to the 5' end of the corresponding 5'-ligation-tagged RNA) is amplified by PCR. polymerase chain reaction (PCR) with PCR Primer 1 and different target-specific primers. For this purpose, an oligonucleotide primer complementary to the sequence of the tag that was added to the 3' end of the first-strand cDNA (PCR Primer 1) and a Target-specific Primer as a second PCR primer that is complementary to a known sequence of the first-strand cDNA (corresponding to the 5' end of the coding region for each of the different RNAs that are desired to be analyzed is used for the PCR as diagramed below:

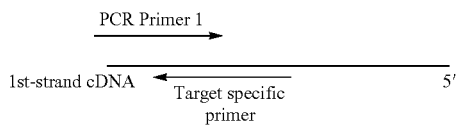

Use of 5'- and 3'-Tagged First-strand cDNA as Sequencing Templates

In some other embodiments, 5' and/or 3' tags comprising or consisting of sequencing tag domains are introduced into the 5'- and/or 3'-tagged first-strand cDNA during the First-strand cDNA Synthesis Reaction (as described above): (i) by use of a first-strand synthesis primer that exhibits a first sequencing tag domain in its 5'-portion, which first sequencing tag domain is incorporated into the 3'-end of the first-strand cDNA; and/or (ii) by use of an RNA Acceptor Oligonucleotide that comprises or consists of a second sequencing tag domain, which second sequencing tag domain is copied into the 3'-end of the first-strand cDNA (e.g., wherein the sequencing tag domains exhibit the sequences of sequencing adaptors for the respective sequencing platform, e.g., for a Roche 454, Illumina Solexa, Intelligent Biosystems, or other sequencing platform). In these embodiments, the 5'- and/or 3'-tagged first-strand cDNA molecules are used as sequencing templates. In some embodiments, the 5'- and/or 3'-tagged first-strand cDNA molecules are converted to double-stranded di-tagged cDNA (generally as described above) and the di-tagged double-stranded cDNA molecules are used as sequencing templates.

Summary

Tagged RNA, and first-strand or double-stranded cDNA can be prepared from uncapped primary RNA molecules using the methods described above for synthesis of 5'-monophosphorylated RNA from primary RNA molecules using RNA polyphosphatase or from primary RNA and capped RNA using TAP or decapping enzyme, polyadenylation of the RNA, 5' ligation tagging of the 5'-monophosphorylated RNA by ligation to an RNA acceptor oligonucleotide using RNA ligase, synthesizing first-strand cDNA using RNA-dependent DNA polymerase (reverse transcriptase) and a first-strand cDNA synthesis primer that anneals to the added poly (A) tail, removing the RNA using RNase I and RNase H, and synthesizing second-strand cDNA (and therefore, double-stranded cDNA) using DNA polymerase and a second-strand cDNA synthesis primer that anneals to the sequence of the portion of first-strand cDNA that is complementary to the 5' ligation tag that was added to the 5' end of the RNA molecules. If desired the double-stranded cDNA molecules synthesized as above can be cloned into a plasmid or other vector for preparation of cDNA libraries corresponding to full-length primary RNA molecules in the sample. Thus, the 5' ligation tagging method enables capture of biologically relevant cDNAs from transcripts that do not have a 5'-cap and therefore would not be captured by oligo-capping cDNA synthesis methods previously known in the art.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A kit for generating 5' ligation-tagged RNA from RNA in a sample, wherein the kit comprises an RNA 5' polyphosphatase (RPP) comprising the sequence of SEQ ID NO 2 and at least one other component selected from the group consisting of: an RNA 5' monophosphatase (RMP); an alkaline phosphatase (AP); a nucleic acid pyrophosphatase; a decapping enzyme; a capping enzyme; an RNA ligase; an RNA acceptor oligonucleotide; a poly(A) polymerase; a poly(U) polymerase; an RNA-dependent DNA polymerase (RT); a first-strand cDNA synthesis primer; an RNase H; a second-strand cDNA synthesis primer; an RNA polymerase (RNAP); 5' exoribonuclease (Xrn); a polynucleotide kinase (PNK); and an RNA molecule that has a 5' triphosphate or diphosphate group wherein the beta or gamma phosphate of said group is labeled.

2. The kit of claim 1, wherein the kit comprises the RNA 5' polyphosphatase, an RNA ligase and an RNA acceptor oligonucleotide.

3. The kit of claim 2, wherein the kit further comprises a first-strand cDNA synthesis primer.

4. The kit of claim 3, wherein the kit further comprises a second strand cDNA synthesis primer.

5. The kit of claim 2, wherein the kit further comprises a poly(A) polymerase.

6. The kit of claim 2, wherein the kit further comprises RNA.

7. The kit of claim 2, wherein the kit further comprises an RNA 5' monophosphatase.

8. The kit of claim 2, wherein the kit further comprises a nucleic acid pyrophosphatase.

9. The kit of claim 2, wherein the kit further comprises a decapping enzyme.

10. The kit of claim 2, wherein the kit further comprises a capping enzyme.

11. The kit of claim 2, wherein the kit further comprises an RNA polymerase.

12. The kit of claim 2, wherein the kit further comprises a polynucleotide kinase.

13. The kit of claim 2, wherein the kit further comprises an RNA molecule that has a 5' triphosphate or diphosphate group wherein the beta or gamma phosphate of said group is labeled.

* * * * *

SEQUENCE LISTING

```
<160> NUMBER OF SEQ ID NOS: 10

<210> SEQ ID NO 1
<211> LENGTH: 603
<212> TYPE: DNA
<213> ORGANISM: Escherichia coli

<400> SEQUENCE: 1
atgttagctt tttgccgctc ttcgttgaag tcaaaaaaat atatcatcat tttactggcg      60
ctcgctgcaa ttgccggact gggtactcat gccgcctgga gtagcaatgg tttgccacgt     120
atcgacaata aaacactggc cagactggca cagcagcacc cggttgtcgt tttgtttcgt     180
```

```
catgctgaac gttgcgaccg ttcaaccaat caatgcttgt cagataaaac aggtattacg    240
gttaaaggta cccaggatgc ccgtgaactg ggcaacgctt ttagtgctga atccctgat    300 ttcgatcttt attccagtaa taccgtccgg accattcagt cggctacctg gttttcagcg    360
ggtaaaaaat tgacggtaga taaacgactt cttcagtgcg gtaatgagat ttatagtgca    420
attaaggact tacaaagcaa agcgcctgat aaaaatatcg ttattttcac ccataatcat    480
tgcctgacat atattgctaa agataagcgt gacgcgacat ttaaacctga ttatctggat    540
ggtttagtca tgcatgtgga aaaaggcaaa gtttatctgg atggggaatt cgttaaccac    600
taa                                                                   603
```

```
<210> SEQ ID NO 2
<211> LENGTH: 200
<212> TYPE: PRT
<213> ORGANISM: Escherichia coli

<400> SEQUENCE: 2
```

```
Met Leu Ala Phe Cys Arg Ser Ser Leu Lys Ser Lys Lys Tyr Ile Ile
 1               5                  10                  15

Ile Leu Leu Ala Leu Ala Ala Ile Ala Gly Leu Gly Thr His Ala Ala
            20                  25                  30

Trp Ser Ser Asn Gly Leu Pro Arg Ile Asp Asn Lys Thr Leu Ala Arg
        35                  40                  45

Leu Ala Gln Gln His Pro Val Val Leu Phe Arg His Ala Glu Arg
    50                  55                  60

Cys Asp Arg Ser Thr Asn Gln Cys Leu Ser Asp Lys Thr Gly Ile Thr
65                  70                  75                  80

Val Lys Gly Thr Gln Asp Ala Arg Glu Leu Gly Asn Ala Phe Ser Ala
                85                  90                  95

Asp Ile Pro Asp Phe Asp Leu Tyr Ser Ser Asn Thr Val Arg Thr Ile
           100                 105                 110

Gln Ser Ala Thr Trp Phe Ser Ala Gly Lys Lys Leu Thr Val Asp Lys
       115                 120                 125

Arg Leu Leu Gln Cys Gly Asn Glu Ile Tyr Ser Ala Ile Lys Asp Leu
   130                 135                 140

Gln Ser Lys Ala Pro Asp Lys Asn Ile Val Ile Phe Thr His Asn His
145                 150                 155                 160

Cys Leu Thr Tyr Ile Ala Lys Asp Lys Arg Asp Ala Thr Phe Lys Pro
                165                 170                 175

Asp Tyr Leu Asp Gly Leu Val Met His Val Glu Lys Gly Lys Val Tyr
           180                 185                 190

Leu Asp Gly Glu Phe Val Asn His
       195                 200
```

```
<210> SEQ ID NO 3
<211> LENGTH: 22
<212> TYPE: RNA
<213> ORGANISM: Arabidopsis thaliana

<400> SEQUENCE: 3
uucgcuugca gagagaaauc ac                                              22

<210> SEQ ID NO 4
<211> LENGTH: 40
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (40)..(40)
<223> OTHER INFORMATION: n is a, c, g, or t

<400> SEQUENCE: 4
ctataggcgc gccaccggtg tttttttttt tttttttttvn                    40

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5
aatgcggccg cgcctccctc gcgccatcag                                30

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
tataggtgcc ggcgcgccac cggtg                                     25

<210> SEQ ID NO 7
<211> LENGTH: 20
<212> TYPE: RNA
<213> ORGANISM: Artificial Sequence
<220> FEATURE:
<223> OTHER INFORMATION: Synthetic

<400> SEQUENCE: 7
gagcggccgc cugcaggaaa                                           20

<210> SEQ ID NO 8
<211> LENGTH: 63
<212> TYPE: DNA
<213> ORGANISM: Artificial Sequence
<220> FEATURE:
<223> OTHER INFORMATION: Synthetic

<400> SEQUENCE: 8
tagacttaga aattaatacg actcactata ggcgcgccac cggtgttttt tttttttttt    60
ttt                                                                  63

<210> SEQ ID NO 9
<211> LENGTH: 50
<212> TYPE: DNA
<213> ORGANISM: Artificial Sequence
<220> FEATURE:
<223> OTHER INFORMATION: Synthetic

<400> SEQUENCE: 9
tcatacacat acgatttagg tgacactata gagcggccgc ctgcaggaaa               50

<210> SEQ ID NO 10
<211> LENGTH: 42
<212> TYPE: DNA
<213> ORGANISM: Artificial Sequence
```

```
<220> FEATURE:
<223> OTHER INFORMATION: Synthetic

<400> SEQUENCE: 10
tagacttaga aattaatacg actcactata ggcgcgccac cg         42
```